US006322970B1

(12) United States Patent
Little et al.

(10) Patent No.: US 6,322,970 B1
(45) Date of Patent: *Nov. 27, 2001

(54) MASS SPECTROMETRIC DETECTION OF POLYPEPTIDES

(75) Inventors: Daniel Little, Boston, MA (US); Hubert Köster, La Jolla, CA (US); G. Scott Higgins, Paisley; David Lough, Berwickshire, both of (GB)

(73) Assignee: Sequenom, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/146,054

(22) Filed: Sep. 2, 1998

Related U.S. Application Data

(63) Continuation-in-part of application No. 08/922,201, filed on Sep. 2, 1997.

(51) Int. Cl.[7] ................... C12Q 1/68; C12Q 1/00; C12P 21/00
(52) U.S. Cl. ................... 435/6; 435/4; 435/69.1
(58) Field of Search ................... 435/4, 6, 69.1; 436/89

(56) References Cited

U.S. PATENT DOCUMENTS

| | | | |
|---|---|---|---|
| 4,214,159 | 7/1980 | Hillenkamp et al. | 250/288 |
| 4,356,270 | 10/1982 | Itakura | 435/317 |
| 4,442,354 | 4/1984 | Hurst et al. | 250/281 |
| 4,681,394 | 7/1987 | Saiki et al. | 435/6 |
| 4,683,195 | 7/1987 | Mullis et al. | 435/6 |
| 4,725,677 | 2/1988 | Köster et al. | 536/27 |
| 4,766,072 | 8/1988 | Jendrisak et al. | 435/91 |
| 4,778,993 | 10/1988 | Waugh | 250/287 |
| 4,920,264 | 4/1990 | Becker | 250/282 |
| 4,983,521 | 1/1991 | Lingappa et al. | 435/172.3 |
| 5,045,694 | 9/1991 | Beavis et al. | 250/287 |
| 5,062,935 | 11/1991 | Schlag et al. | 204/157.41 |
| 5,118,605 | 6/1992 | Urdea | 435/6 |
| 5,118,937 | 6/1992 | Hillenkamp et al. | 250/282 |
| 5,135,870 | 8/1992 | Williams et al. | 436/173 |
| 5,198,531 | 3/1993 | Webber et al. | 525/332.2 |
| 5,202,561 | 4/1993 | Giessmann et al. | 250/281 |
| 5,210,412 | 5/1993 | Levis et al. | 250/288 |
| 5,324,637 | 6/1994 | Thompson et al. | |
| 5,373,156 | 12/1994 | Franzen | 250/288 |
| 5,376,788 | 12/1994 | Standing et al. | 250/287 |
| 5,380,833 | 1/1995 | Urdea et al. | 536/22.1 |
| 5,381,008 | 1/1995 | Tanner et al. | 250/288 |
| 5,382,793 | 1/1995 | Weinberger et al. | 250/288 |
| 5,410,068 | 4/1995 | Coull et al. | 548/545 |
| 5,492,817 | 2/1996 | Thompson et al. | 435/68.1 |
| 5,503,980 | 4/1996 | Cantor | 435/6 |
| 5,510,613 | 4/1996 | Reilly et al. | 250/287 |
| 5,538,897 | * 7/1996 | Yates et al. | 436/89 |
| 5,545,539 | 8/1996 | Miller | 435/91.2 |
| 5,547,835 | 8/1996 | Köster | 435/6 |
| 5,580,733 | 12/1996 | Levis et al. | 435/6 |
| 5,604,099 | 2/1997 | Erlich et al. | 435/6 |
| 5,605,798 | 2/1997 | Köster | 435/6 |
| 5,612,474 | 3/1997 | Patel | 536/27.14 |
| 5,622,824 | 4/1997 | Köster | 435/6 |
| 5,622,829 | 4/1997 | King et al. | 435/6 |
| 5,625,184 | 4/1997 | Vestal et al. | 250/287 |
| 5,627,369 | 5/1997 | Vestal et al. | 250/287 |
| 5,628,184 | 5/1997 | Santos | 60/39.281 |
| 5,631,134 | 5/1997 | Cantor | 435/6 |
| 5,641,959 | 6/1997 | Holle et al. | 250/287 |
| 5,643,722 | 7/1997 | Rothschild et al. | 435/6 |
| 5,643,798 | 7/1997 | Beavis et al. | 436/94 |
| 5,654,150 | * 8/1997 | King et al. | 435/6 |
| 5,654,545 | 8/1997 | Holle et al. | 250/287 |
| 5,663,242 | 9/1997 | Ghosh et al. | 525/329.4 |
| 5,670,322 | 9/1997 | Eggers et al. | 435/6 |
| 5,670,381 | 9/1997 | Jou et al. | 436/518 |
| 5,677,195 | 10/1997 | Winkler et al. | 435/518 |
| 5,691,141 | 11/1997 | Köster | 435/6 |
| 5,700,642 | 12/1997 | Monforte et al. | 435/6 |
| 5,742,049 | 4/1998 | Holle et al. | 250/282 |
| 5,760,393 | 6/1998 | Vestal et al. | 250/282 |
| 5,777,324 | 7/1998 | Hillenkamp | 250/288 |
| 5,777,325 | 7/1998 | Weinberger et al. | 250/287 |
| 5,792,664 | 8/1998 | Chalt et al. | 436/89 |
| 5,795,714 | 8/1998 | Cantor et al. | 435/6 |
| 5,830,655 | 11/1998 | Monforte et al. | 435/6 |
| 5,864,137 | 1/1999 | Becker et al. | 250/287 |
| 5,869,242 | 2/1999 | Kamb | 436/6 |

FOREIGN PATENT DOCUMENTS

| | | |
|---|---|---|
| 0269250 | 6/1988 | (EP) . |
| 0655501 | 5/1995 | (EP) . |
| 2168478 | 6/1986 | (GB) . |
| 9014148 | 11/1990 | (WO) . |
| 9210092 | 6/1992 | (WO) . |
| 9213629 | 8/1992 | (WO) . |
| 9324834 | 12/1993 | (WO) . |
| 9400562 | 1/1994 | (WO) . |
| 9411530 | 5/1994 | (WO) . |

(List continued on next page.)

OTHER PUBLICATIONS

Siuzdak et al. PNAS 91:11290–11297, 1994.*
Chait et al. Science 257:1885–1894, 1992.*
Ji et al. Electrophorsis 15:391–405, 1994.*

(List continued on next page.)

Primary Examiner—Eggerton A. Campbell
(74) Attorney, Agent, or Firm—Stephanie L. Seidman; Heller Ehrman White & McAuliffe LLP

(57) ABSTRACT

A process for determining the identity of a target polypeptide using mass spectroscopy is provided. Depending on the target polypeptide to be identified, a process as disclosed can be used, for example, to diagnose a genetic disease or chromosomal abnormality, a predisposition to a disease or condition, or infection by a pathogenic organism; or for determining identity or heredity. Kits for performing the disclosed processes also are provided.

95 Claims, 3 Drawing Sheets

FOREIGN PATENT DOCUMENTS

| | | |
|---|---|---|
| 9416101 | 7/1994 | (WO) . |
| 9421822 | 9/1994 | (WO) . |
| 9428418 | 12/1994 | (WO) . |
| 9507361 | 3/1995 | (WO) . |
| 9525737 | 9/1995 | (WO) . |
| 0683234 | 11/1995 | (WO) . |
| 9531429 | 11/1995 | (WO) . |
| 9629431 | 9/1996 | (WO) . |
| 9632504 | 10/1996 | (WO) . |
| 9633731 | 11/1996 | (WO) . |
| 9636732 | 11/1996 | (WO) . |
| 9636986 | 11/1996 | (WO) . |
| 9636987 | 11/1996 | (WO) . |
| 9708306 | 3/1997 | (WO) . |
| 9716699 | 5/1997 | (WO) . |
| 9719110 | 5/1997 | (WO) . |
| 9737041 | 10/1997 | (WO) . |
| 9742348 | 11/1997 | (WO) . |
| 9743617 | 11/1997 | (WO) . |
| 9811249 | 3/1998 | (WO) . |
| 9820019 | 5/1998 | (WO) . |
| 9820020 | 5/1998 | (WO) . |
| 9820166 | 5/1998 | (WO) . |
| 9832876 | 7/1998 | (WO) . |

OTHER PUBLICATIONS

Andersen, et al., Electrospray ionization and matrix assisted laser desorption/ionization mass spectrometry: Powerful analytical tools in recombinant protein chemistry, *Nature Biotech.* 14:449–457 (1996).

Andersen, et al., Electrospray ionization and matrix assisted laser desorption/ionization mass spectrometry: Powerful analytical tools in recombinant protein chemistry, *Nature Biotech.* 14:449–457 (1996).

Anderson, et al., Preparation of a cell–free protein–synthesizing system from wheat germ, *Meth. Enzymology* 101:635–644 (1983).

Anker et al., Tetranucleotide repeat polymorphism at the human thryoid perxodase (hTPO)locus, *Human Molec. Genetics.* 1:137(1992).

Ardrey, Electrospray mass spectrometry, *Spectroscopy Europe* 4:10–18 (1992).

Arlinghaus et al., "Applications of resonance ionization spectroscopy for semiconductor, environmental and biomedical analysis, and for DNA sequencing", *SPIE*, vol. 1435, *Opt. Methods Ultrasensitive Detect. Anal. Tech. Appl.* pp. 26–35 (1991).

Barany, Genetic disease detection and DNA amplification using cloned thermostable ligase, *Proc. Natl. Acad. Sci. USA* 88:189–193 (1991).

Batra, et al., Insertion of constant region domains of human $IgG_1$ into CD4–PEG40 increases its plasma half–life, *Molec, Immunol.* 30:379–386 (1993).

Beck et al., Applications of dioxetane chemiluminescent probes to molecular biology, *Anal. Chem.* 62:2258–2270 (1990).

Beck et al., Chemiluminescent detection of DNA: application for DNA sequencing and hybridization, *Nucl Acids Res* 17:5115–5123 (1989).

Beckmann and Weber, "Survey of human and rat microsatellites", *Genomics* 12:627–631 (1992).

Berkenkamp et al., Infrared MALDI mass spectrometry of large nucleic acids, *Science* 281:260–2 (1998).

Bodansky et al., (eds.) *Peptide Synthesis,* John Wiley & Sons, New York (1976).

Borrebaeck (ed.), *Antibody Engineering,* Oxford University Press, New York (1995).

Braun et al., Detecting CFTR gene mutations by using primer oligo base extension and mass spectrometry, *Clinical Chemistry* 43:1151–1158 (1997).

Braun et al., Improved Analysis of Microsatellites Using Mass Spectrometry, *Genomics* 46:18–23 (1997).

Brennan and Matthews, Hb Auckland [α87(F8)His—Asn]: A new mutation of the proximal histidine identified by electrospray mass spectrometry, *Hemoglobin* 21:393–403 (1997).

Ehring et al., Photochemical versus thermal mechanislms in matrix–assisted laser desorption/ionization probed by back side desorption, *Rapid Comm in Mass Spect.* 10:821–824 (1996).

Ellison and Hochstrasser, Epitope–tagged ubiquitin, *J. Biol. Chem.* 266:21150–21157 (1991).

Erickson and Blobel, "Cell–free translation of messenger RNA in a wheat germ system," *Meth. Enzymol.* 96:38–50 (1983).

Falick, et al., Tandem mass spectrometry in the clinical analysis of variant hemoglobins, *Rapid Comm. Mass Spec.* 4:396–400 (1990).

Fattom, et al., Comparative immunogenicity of conjugates composed of the *Staphhlococcus aureu* type 8 capsular polysaccharide bound to carrieer proteins by adipic acid dihyudrazide or N–succinimidyl–3–(2–pyridyldithio)propionate, *Infection Immunity* 60:574–589 (1992).

Fey, et al., Proteome analysis of *Saccharomyces cervisiae:* A methodological outline. *Electrophoresis* 18:1361–1362 (1997).

Frank et al., DNA chain length markers and the influence of base composition on electrophoretic mobility of oligodeoxyribonucleotides in polyacrylamide–gels, *Nucl Acids Res* 6:2069–2087.

Freshney, *Culture of Animal Cell,* 2nd Ed., Alan R. Liss, Inc., New York (1987).

Fu et al., A DNA sequencing strategy that requires only five bases of known terminal sequenec for priming, *Proc. Natl. Acad. Sci. USA* 92:10162–10166 (1995).

Fu et al., A DNA sequencing strategy which requires only five bases of known terminal sequence for priming, Paper presented, Genome Mapping and Sequencing, Cold Spring Harbor Laboratory.

Fu et al., Efficient preparation of short DNA sequence ladders potentially suitable for MALDI–TOF DNA sequencing, *Genetic Analysis* 12:137–142 (1996).

Fu et al., Sequencing double–stranded DNA by strand displacement, *Nucl Acids Res* 25:677–679 (1997).

Fu et al., Sequencing exons 5 to 8 of the p53 gene by MALDI–TOF mass spectrometry, *Nat Biotechnol* 16:381–4 (1998).

Fu, et al., Variation of the CGG repeat at the Fragile X site results in genetic instability: Resolution of the Sherman Paradox, *Cell* 67:1047–1058 (1991).

Ganem et al., Detection of oligonucleotide duplex forms by ion–spray mass spectrometry, *Tetrahedron Letters* 34:1445–1448, (1993).

Gene Transfer Vectors for Mammalian Cells, Cold Spring Harbor Laborartory, Cold Spring Harbor, New York (1987).

Gildea et al., A versatile acid–labile linker for modification of synthetic biomolecules, *Tetrahedron Lett.* 31:7095–7098 (1990).

Greene and Wuts, *Protective Groups in Organic Synthesis*, 2nd Ed., John Wiley & Sons, Inc., New York (1991).

Gross et al., Investigations of the metastable decay of DNA under ultraviolet matrix–assisted laser desorption/ionization conditions with post–source–decay analysis and hydrogen/deuterium exchange, *J Amer Soc for Mass Spect 9*:866–878 (1998).

Gruić–Sovulj I. et al., Matrix–assisted laser desorption/ionisation mass spectrometry of transfer ribonucleic acids isolated from yeast, *Nucleic Acids Res.* 25(9):1859–61 (1997).

Gust et al., Taxonomic classification of Hepatitis A virus, *Intervirology 20*:1–7 (1983).

Guyader et al., Genome organization and transactivation of the human immunodeficiency virus type 2, *Nature 326*:662–669 (1987).

Haglund et al., Matrix–assisted laser–desorption mass spectrometry of DNA using an infrared free–electron laser, *SPIE 1854*:117–128.

Higuchi, et al., Kinetic PCR analysis: Real–time monitoring of DNA amplification reactions, *Bio/Technology 11*:1026–1030 (1993).

Hillenkamp and Ehring, Laser desorption mass spectrometry Part 1: Basic mechanisms and techniques, *Mass Spectrometry in the Biological Sciences: A tutorial*, pp. 165–179 (1992).

Hillenkamp, et al., Matrix assisted UV–laser desorption/ionization: A new approtach to mass spectrometry of large biomolecules, In *Biological Mass Spectrometry* (Burlingame and McCloskey, eds.), Elsevier, Amsterdam (1989).

Hirst, et al., Genotype prediction in the fragile X syndrome, *J. Med. Genet. 28*:824–829 (1991).

Hogan, et al., *Manipulating the Mouse Embryo*, Cold Spring Harbor Laboratory, Cold Spring Harbor, New York (1986).

Hsiung et al., A new simpler photoaffinity analogue of peptidyl rRNA, *Nucl Acids Res 1*:1753–1762 (1974).

Huse, et al., Generation of a large combinatorial library of the immunoglobulin repertoire in phage lambda, *Science 246*:1275–1281 (1989).

Huth–Fehre et al., Matrix–assisted laser desorption mass spectrometry of oligodeoxythymidylic acids, *Rapid Comm in Mass Spect. 6*:209–213 (1992).

Jacobson, et al., Applications of mass spectrometry to DNA sequencing, *GATA 8*:223–229 (1991).

Jellinek, et al., Potent 2'–amino–2'–deoxypyrimidine RNA inhibitors of basic fibroblast growth factor, *Biochemistry 54*:11363–11372 (1995).

Ji, et al., Two–dimensional electrophoretic analysis of proteins expressed by normal and cancerous human crypts: Application of mass spectrometry to peptide–mass fingerprinting. *Electrophoresis 15*:391–405 (1994).

Juhasz, et al., Applications of delayed extraction matrix–assisted laser desorption inoization time–of–flight mass spectrometry to oligonucleotide anaylsis, *Anal. Chem. 68*:941–946 (1996).

Jurinke et al., Analysis of ligase chain reaction products via matrix–assisted laser desorption/ionization time–of–flight––mass spectrometry, *Analy Biochem 237*:174–181 (1996).

Jurinke et al., Application of nested PCR and mass spectrometry for DNA–based virus detection: HBV–DNA detected in the majority of isolated anti–HBc positive sera, *Genetic Analysis 14*:97–102 (1998).

Jurinke et al., Detection of hepatits B virus DNA in serum samples via nested PCR and MALDI–TOF mass spectrometry, *Genetic Analysis 13*:67–71 (1996).

Jurinke et al., Recovery of nucleic acids from immobilized biotin–streptavidin complexes using ammonium hydroxide and applications in MALDI–TOF mass spectrometry , *Anal. Chem. 69*:904–910 (1997).

Kirpekar et al., DNA sequence analysis by MALDI mass spectrometry, *Nucleic Acids Res. 26*:2554–9 (1998).

Köster et al., A strategy for rapid and efficient DNA sequencing by mass spectrometry, *Nature Biotech 14*:1123–1128 (1996).

Köster et al., N–ACYL proecting groups for deoxynucleosides, A quantitive and comparative study, *Tetrahedron 37*:363–369 (1981).

Köster et al., Oligonucleotide synthesis and multiplex DNA sequencing using chemiluminescent detection, *Nucl Acids Res 24*:318–321 (1991).

Köster et al., Polymer support oligonucleotide synthesis—XV$^{1,2}$, *Tetrahedron 40*:102–112 (1984).

Köster et al., Some improvements in the synthesis of DNA of biological interest, *Nucl Acids Res 7*:39–59 (1980).

Köster et al., Well–defined insoluble primers for the enzymatic synthesis of oligo– and polynucleotides, *Hoppe–Seyler's Z. Physiol. Chem. 359*:11579–1589 (1978).

Kremer, et al., Mapping of DNA instability at the Fragile X to a trinucleotide repeat sequence p(CCG)n, *Science 252*:1711–1714 (1991).

Kussmann, et al., Matrix–assisted laser desorption/ionization mass spectrometry sample preparation techniques designed for various peptide and protein analytes, *J. Mass Spec. 32*:593–601 (1997).

La Spada, et al., Androgen receptor gene mutation in X–linked spinal and bulbar muscular atrophy, *Nature 352*:77–79 (1991).

Lawrance et al., Megabase–scale mapping of the HLA gene complex by pulsed field gel electrophoresis, *Science 235*:1387–1389 (1987).

Leznoff, The use of insoluble polymer supports in general organic synthesis, *Accts. Chem. Res. 11*:327–333(1978).

Li, et al., Analysis of single mammalian cell lysates by mass spectrometry, *J. Am. Chem. Soc.* 118:11662–11663 (1996).

Li et al., High–Resolution MALDI Fourier Transform Mass Spectrometry of Oligonucleotides, *Anal Chem 68*:2090–2096 (1996).

Lin, et al., Modified RNA sequence pools for in vitro selection, *Nucleic Acids Res. 22*:5229–5234 (1994).

Little et al., Detection of RET proto–oncogene codon 634 mutations using mass spectrometry, *J. Mol Med. 75*:745–750 (1997).

Little et al., Direct detection of synthetic and biologically generated double–stranded DNA by MALDI–TOF MS, *J. Mass Spec 17*:1–8 (1997).

Little et al., Identification of apolipoprotein E polymorphisms using temperature cycled primer oligo base extension and mass spectrometry, *Short Communiation*.

Little et al., MALDI on a chip: analysis of arrays of low–femtomole to subfemtomole quantities of synthetic oligonucleotides and DNA diagnostic products dispensed by a piezoelectric pipet, *Anal Chem 69*:4540–4546 (1997).

Little et al., Mass spectrometry from miniaturized arrays for full comparative DNA analysis, *Nature Med 3*:1413–1416 (1997).

Little et al., Verification of 50– to 100–mer DNA and RNA sequences with high–resolution mass spectrometry, *Proc. Natl. Acad. USA Sci.* 92:2318–2322 (1995).

Mahadevan, et al., Myotonic dystrophy mutation: An unstable CTG repeat in the 3' untranslated region of the gene, *Science* 255:1253–1255 (1992 ).

Mayer and Walker, *Immunochemical Methods in Cell and Molecular Biology,* Academic Press, London (1987).

McCloskey, (ed.), Mass Spectrometry, *Meth. Enz.* 193 (1990).

McCray and Trentham, Properties and uses of photoreactive caged compounds, *Ann. Rev. Biophys. Biophys. Chem.* 18:239–270 (1989).

McLafferty, High–resolution tandem FT mass spectrometry above 10 kDa. *Accounts Chem. Res.* 27:379–386 (1994).

Miyazaki, et al., The first Japanese case of Hb Santa Ana, an unstable abnormal hemoglobin, identified rapidly by electrospray ionization mass spectrometry. *Internal Medicine* 36:365–370 (1997).

Monforte and Becker, High–throughput DNA analysis by time–of–flight mass spectrometry, *Nature Medicine* 3:360–362 (1997).

Mosca et al., Identified by mass spectormetry and DNA analysis, *Hemoglobin* 17(3):261–268 (1993).

Murray, "DNA sequencing by mass spectrometry", *J. Mass. Spect.* 31:1203–1215 (1996).

Narang, et al., Improved phospotriester method for the synthesis of fragments, *Meth. Enzymol.* 68:90–98 (1979).

Nora and Fraser, Medical Genetics: Principles and Practice, Lea & Febiger, Philadelphia (1994).

Nordhoff et al., Ion stability of nucleic acids in infrared matrix–assisted laser desorption/ionization mass spectrometry, *Nuc Acids Res.* 21:3347–3357 (1993).

Nordorff et al., Matrix–assisted laser desorption/ionization mass spectrometry of nucleic acids with wavelength in the ultraviolet and infrared, *Rapid Comm. Mass Spect* 6:771–776 (1992).

O'Donnell et al., High–density, covalent attachment of DNA to siliocn wafers for analysis by MALDI–TOF mass spectrometry, *Analytical Chemistry* 69:2438–2443 (1997).

O'Donnell et al., MassArray as an enabling technology for the industrial–scale analysis of DNA, *Genetic Engineering News* 17 (1997).

O'Donnell–Maloney et al., Microfabrication and array technologies for DNA sequencing and diagnostics, *Genteic Analysis: Biomolecular Engineering* 13:151–157 (1996).

Overberg et al., Laser Desorption Mass Spectrometry. Part II Performance and Applications of Matrix–Assisted Laser Desorption/Ionization of Large Biomolecules, *Mass Spectrometry in the Biological Science:* A Tutorial 181–197 (1992).

Pagratis, et al., Potent 2'–amino–. land 2'–fluoro–2'–deoxyribonucleotide RNA inhibitors of keratinocyte growth factor, *Nature Biothech.* 15:68–73 (1997).

Pieles et al., Matrix–assisted laser desorption ionization time–of–flight mass spectrometry: a powerful tool for the mass and sequence analysis of natural and modified oligonucleotides, *Nucleic Acids Res.* 21:3191–3196 (1993).

Ploos van Amstel and Reitsma, Tetranucleotide repeat polymorphism in the vWF gene, *Nucleic Acids Res.* 18:4957 (1990).

Polymeropoulos, et al., Dinucleotide repeat polymorphism at the human CTLA4 gene, *Nucleic Acids Res.* 19:4018 (1991).

Polymeropoulos, et al., Tetranucleotide repeat polymorphism at the human c–fes/fps proto–oncongene (FES), *Nucleic Acids Res.* 19;4018 (1991).

Polymeropoulos, et al., Trinucleotide repeat polymorphism at the human pancreatic phospholipase A–2 gene (PLA2), *Nucleic Acids Res.* 18:7468 (1990).

Pomerantz et al., Determination of oligonucleotide composition from mass spectrometrically measured molecular weight, l*Am. Soc. Mass Spectrom.* 4:204–09 (1993).

Prome et al., Use of combined mass spectrometry methods for the characterization of a new variant of human hemogloblin: The double mutant hemoglobin villeparisis beta77(EF1), *J. Americ. Soc. for Mass Spectr.* 7(2):163–167 (1996).

Raftery, et al., Characterization of a mutant recombinant S100 protein using electrospray ionization mass spectrometry. *Rapid Comm. Mass Spec.* 11:405–409 (1997).

Ratner, et al., "Complete nucleotide sequence of the AIDS virus, HTLV–III", *Nature* 313:277–284.

Rink, "Solid–phase synthesis of protected peptide fragments using a trialkoxy–diphenyl–methlester resin", *Tetrahedron Lett.* 28:3787–3790 (1987).

Roberts, et al., "Efficient translation of tobacco mosaic virus RNA and rabbit globin 9S RNA in a cell–free system from commercial wheat germ", *Proc. Nat. Acad. Sci, USA* 70:2330–2334 (1973).

Rolfs, et al., PCR: Clinical Diagnostics and Research, Springer–Verlag, Berlin (1992).

Ruppert et al., A filtration method for plasmid isolation using microtiter filter plates, *Anal. Biochem.* 230:130–134 (1995).

Ruppert et al., A rapid and high throughput method for plasmid isolations, Presented: Automation in Mapping and DNa Sequencing Conference, Aug. 31–Sep. 2 1994.

Ruppert et al., Preparation of plasmid DNA as sequencing templates in a microtiter plate format, Paper presented, Cold Spring Harbor Laboratory.

Schram, "Mass spectrometry of nucleic acid components", *Biomed Appl of Mass Spect* 34:203–287.

Seong, et al., "*Escherichia coli* formylmethionine tRNA: mutations in $^{GGG}ccc$ sequence conserved in anticodon stem of initiator tRNS affect initiation of protein synthesis and confirmation of anticodon loop", *Proc. Natl. Acad. Sci. USA* 84:334–338 (1987).

Sequenom Advances the Industrial Genomics Revolution with the Launch of Its DNA MassArray™ Automated Process Line, Press Release: Sep. 28, 1998, http://www.sequenom.com/pressrelease.htm.

Sequenom Reports DNA MassArray™Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Sequenom Reports On Use of Its DNA MassArray™Technology to Analyze Genes Associated with Alzheimer's Disease adn Arteriosclerosis: Technology Hss Applications in Drug Development, Press Release: Sep. 22, 1997, http://www.sequenom.com/pressrelease.htm.

Sequenom Signs Agreement Wtih Bruker–Fanzen Analytik to Develop Mass Spectrometer for DNA Massarray Analysis, Press Release: Jan. 12, 1998, http://www.sequenom.com/pressrelease.htm.

Sequenom Uses DNA MassArray™to Sequence Section of Human Cancer–Related p53 Gene, Press Release: Mar. 27, 1998, http://www.sequenom.com /pressrelease.htm.

Shaler et al., Effect of Impurities on the matrix–assisted laser desorption mass spectra of single–stranded oligondeoxynucleotides, *Anal. Chem.* 68:576–579 (1996).

Siegert et al., Matrix–assisted laser desorption/ionization time–of–flight mass spectrometry for the detection of polymerase hain reaction products containing 7–deasapurine moieties, *Anal. Biochem.* 243:55–65 (1996).

Sinha et al., β–cyanoethyl N, N–dialkylamino/N–morpholinomonochloro phosphoamidites, new phosphitylating agents facilitating ease of deprotection and work–up of synlthesized oligonucleotides, *Tetrahedron Lett.* 24:5843–5846m (1983).

Siudzak, The emergence of mass spectrometry in biochemical research, *Proc. Natl. Acad. Sci. USA* 91:11290–112947 (1994).

Smith et al., Capillary zone electrophoresis–mass spectrometry using an electrospray ionization interface, *Anal. Chem.* 60:436–441 (1988).

Smith, et al., New developments in biochemical mass spectrometry: Electrospray Ionization, *Anal. Chem.* 62:882–899 (1990).

Spirin, et al., "A continuous cell–free translation system capable of producing polypeptides in high yield", *Science* 242:1162–1164 (1988).

Sproat et al., The synthesis of protected 5'–amino–2', 5'–dideoxyribonucleoside–3'–O–phosphoramidites; applications of 5'–amino–oligodeoxyribonucleotides, *Nucleic Acids Res.* 15:6181–6196 (1987).

Tam, et al., Biological availability and nuclease resistance extend the in vitro activity of a phosphorothioate–3'hydroxypropylamine oligonucleotide, *Nucleic Acids Res.* 22:977–986 (1994).

Tang, et al., Improving mass resolution in MALDI/TOF analysis of DNA.

Tang et al., Matrix–assisted laser desorption/ionization mass spectrometry of immobilized duplex DNA probes, *Nucleic Acids Research* 23:3126–3131 (1995).

Thompson and Thompson (eds.), *Genetics in Medicine*, 4th Ed., W.B. Saunder Co., Philadelphia (1986).

Valaskovic, et al., Attomole protein characterization by capillary electrophoresis–mass spectrometry, *Science* 273:1199–1202 (1996).

Valaskovic, et al., Attomole–sensitivity electrospray source for large–molecule mass spectrometry, *Anal. Chem.* 67:3802–3805 (1995).

Vestal, et al., Delayed extraction matrix–assisted laser desorption time–of–flight mass spectrometry, *Rapid. Comm. Mass Spectrom.* 9:1044–1050 (1995).

von Eckardstein, et al., Structural analysis of human apoliporotein A–I variants. *J. Biol. Chem.* 265:8610–8617 (1990).

Vorm, et al., Improved resolution and very high sensitivity in MALDI TOF of matrix surfaces made by fast evaporation, *Anal. Chem.* 66:3281–3287 (1994).

Wain–Hobson, et al., "Nucleotide sequence of the AIDS virus, LAV", *Cell* 40:9–17 (1985).

Walker, et al., Multiplex strand displacement amplification (SDA) and detection of DNA sequences from *Mycobacterium tuberculosis* and other mycobacteria, *Nucleic Acids Res.* 22:2670–2677 (1994).

Ward, et al., Binding activities of a repertoire of single immunoglobulin variable domains secreted from *Escherichia coli*, *Nature* 341:544–546 (1989).

Weber, et al., Abundant class of human DNA polymorphisms which can be typed using the polymerase chain reaction, *Am. J. Hum. Genet.* 44:388–396 (1989).

Weir, (ed.), *Handbook of Experimental Immunology*, vol. 1–4, Blackwell Scientific Publications, Oxford (1986).

Welhöner, et al., Uptake and concentration of bioactive macromolecules by K562 cells via the transferrin cycle utilizing an acid–labile transferrin conjugate, J. Biol. Chem. 266:4309–4314 (1991).

Wiedmann, et al., Ligase chain reaction (LCR)—Overview and applications, *PCR Methods and Applications*, pp. S51–S64, Cold Spring Harbor Laboratory, Cold Spring Harbor, New York (1994).

Winter and Harris, Humanized antibodies, *Immunol. Today* 14:243–246 (1993).

Woodward (ed.), Immobilized cells and enzymes: A practical approach, IRL Press, Oxofrd (1985).

Wu (ed.), Recombinant DNA, part E, *Meth. Enz.* 154 (1987).

Wu (ed.), Recombinant DNA, part F, *Meth. Enz.* 155 (1987).

Wu et al., Matrix–assisted Laser Desorption Time–of–flight Mass Spectrometry of Oligonucleotides Using 3–Hydroxypicolinic Acid as an Ultraviolet–sensitive Matrix, *Rapid Comm Mass Spec* 7:142–146 (1993).

Wu et al., Time–of–Flight Mass Spectrometry of Underivatized Single–Stranded DNA Oligomers by Matrix–Assisted Laser Desorption, *Anal. Chem.* 66:1637–1645 (1994).

Yamashita and Fenn, Electrospray ion source. Another variation on the free–jet theme, *J. Phys. Chem.* 88:4451–4459 (1984).

Yates, III, Mass spectrometry and the age of the proteome, *J. Mass Spec.* 33:1–19 (1998).

Zubay, In vitro synthesis of protein in microbial systems, *Ann. Rev. Genetics* 7267–287 (1973).

Zuliani and Hobbs, Tetranucleotide repeat polymorphism is the LPL gene, *Nucleic Acids Res.* 18:4958(1990).

Gait, M. J. ed., *Oligonucleotide Synthesis* (1984).

Glover, D. M. ed., *DNA Cloning*, vol. 2 (1985).

Glover D. M. ed., *DNA Cloning*, vol. 1 (1985).

Hames and Higgins eds., *Nucleic Acid Hybridisation* (1984).

Hames and Higgins eds., *Transcription and Translation* (1984).

Jefferys et al., "Hypervariable 'minisatellite' regions in human DNA", *Nature* 314:67–63 (1985).

Litt and Luty, "A hypervariable microsatellite revealed by in vitro amplification of a dinucleotide repeat within the cardiac muscle actin gene", *Am. J. Hum. Genet.* 44:397–401 (1989).

Miller and Calos eds., *Gene Transfer Vectors For Mammalian Cells* (1987).

Nakamura et al., "Variable number of tandem repeat (VNTR) markers for human gene mapping", *Science* 235:1616–1622 (1987).

Nishimura and Murray, "A tetranucleotide repeat for the F13B locus", *Nucleic Acids Res.* 20:1167 (1982).

Perbal B., *A Practical Guide to Molecular Cloning* (1984).

Polymeropoulos et al., "Tetranucleotide repeat polymorphism at the human coagulation factor XIII A subunit gene (F13A1)", *Nucleic Acids Res.* 19:4306 (1991).

Polymeropoulos et al., "Tetranucleotide repeat polymorphism at the human aromatase cytochrome P–450 gene (CYP19)", *Nucleic Acids Res.* 19:195 (1991).

Polymeropoulos, et al., Dinucleotide repeat polymorphism at the int–2 proto–oncogene locus (INT2), *Nucleic Acids Res.* 18:7468 (1990).

Tautz D., "Hypervariability of simple sequences as a general source for polymorphic DNA markers", *Nucleic Acids Res.* 17:6463–6471 (1989).

Belanger et al., Molecular mass and carbohydrate structure of prostate specific antigen: studies for establishment of an international PSA standard, *Prostate* 27(4):187–197 (1995).

Haag et al., Rapid indentification and speciation of Haemophilus bacteria by matrix–assisted laser desorption/ionizaton time–of–flight mass spectrometry, *J. of Mass Spectrometry* 33(8):750–756 (1998).

Krishnamurthy and Ross, Rapid identification of bacteria by direct matrix assisted laser desorption/ionization mass spectrometric analysis of whole cells, *Rapid Comm in Mass Spectrometry* 10(15):1992–1996 (1996).

Krishnamurthy et al., Biomolecules and mass spectroscopy, *J. of Natural Toxins* 6(2):121–162 (1997).

Tas et al., Characterization of virus infected cell cultures by pyrolysis/direct chemical ionization mass spectrometry, *Biomed and Environ Mass Spect* 18(9):757–760 (1989).

Welham et al., The rapid identification of intact microorganisms by matrix–assisted laser desorption/ionization time–of–flight mass spectrometry, *Pharmacy and Pharamacology Comm.* 4(2):81–87 (1998).

* cited by examiner

5'd (GAC TTT ACT TGT ACG TGC *ATA ATA CGA CTC ACT ATA GGG AGA* CTG AAC ATG GGC AGT CTG AGC CAG CAG ACG CAG CAC AAG GCT GAG CAG CAG CAG CAG AGT CAG CAG CAG CAG CAG CAG CAT CAG *CAG CAG CAG* CAG CAG CAG *CAG CAG CAG* CAC CTC ACG AGG GCT CCG GGC CTC ATC ACC CCG GGT CCC CCC CAG CAG CCC AGC AGA ACC AGT ACG TCC ACA TTT CAA GTT CAT CAT CAT CAT CAT CAT TGA GAA TCA) -3' (SEQ ID NO. 8)

B

MGSLSQTPGH KAEQQQQQQ QQQQHQHQQ QQQQQQQHL
SRAPGLITPG PPGQPSRTST STGQVHHHHH H (SEQ ID NO. 9)

SEQUENCE LISTING

<160> NUMBER OF SEQ ID NOS: 9

<210> SEQ ID NO 1
<211> LENGTH: 24
<212> TYPE: DNA
<213> ORGANISM: Bacteriophage SP6
<220> FEATURE:
<221> NAME/KEY: promoter
<222> LOCATION: (1)..(24)
<223> OTHER INFORMATION: SP6 promoter sequence (single-stranded)

<400> SEQUENCE: 1
catacgattt aggtgacact atag                                          24

<210> SEQ ID NO 2
<211> LENGTH: 18
<212> TYPE: DNA
<213> ORGANISM: Bacteriophage SP6
<220> FEATURE:
<221> NAME/KEY: promoter
<222> LOCATION: (1)..(18)
<223> OTHER INFORMATION: SP6 promoter sequence (single-stranded)

<400> SEQUENCE: 2
atttaggtga cactatag                                                 18

<210> SEQ ID NO 3
<211> LENGTH: 20
<212> TYPE: DNA
<213> ORGANISM: Bacteriophage T3
<220> FEATURE:
<221> NAME/KEY: promoter
<222> LOCATION: (1)..(20)
<223> OTHER INFORMATION: T3 promoter sequence (single-stranded)

<400> SEQUENCE: 3
attaaccctc actaaaggga                                               20

<210> SEQ ID NO 4
<211> LENGTH: 20
<212> TYPE: DNA
<213> ORGANISM: Bacteriophage T7
<220> FEATURE:
<221> NAME/KEY: promoter
<222> LOCATION: (1)..(20)
<223> OTHER INFORMATION: T7 promoter sequence (single-stranded)

<400> SEQUENCE: 4
taatacgact cactataggg                                               20

<210> SEQ ID NO 5
<211> LENGTH: 8
<212> TYPE: DNA
<213> ORGANISM: Prokaryote
<220> FEATURE:
<221> NAME/KEY: misc_feature
<222> LOCATION: (1)..(8)
<223> OTHER INFORMATION: Primer sequence containing the Shine-Dalgarno (prokaryotic ribosome binding) sequence

<400> SEQUENCE: 5 taaggagg                                                          8

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Primer
      containing T7 promoter sequence
<220> FEATURE:
<221> NAME/KEY: promoter
<222> LOCATION: (19)..(42)
<223> OTHER INFORMATION: T7 promoter sequence located within primer as
      indicated

<400> SEQUENCE: 6
gactttactt gtacgtgcat aatacgactc actataggga gactgaccat gggcagtctg    60
agcca                                                                65

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Primer
      encoding His-6 "tag" peptide
<220> FEATURE:
<221> NAME/KEY: repeat_region
<222> LOCATION: (10)..(27)
<223> OTHER INFORMATION: Sequence encoding His-6 "tag" feature located
      within primer as indicated

<400> SEQUENCE: 7
tgattctcaa tgatgatgat gatgatgaac ttgaaatgtg gacgtac                 47

<210> SEQ ID NO 8
<211> LENGTH: 270
<212> TYPE: DNA
<213> ORGANISM: Homo sapiens
<220> FEATURE:
<221> NAME/KEY: repeat_region
<222> LOCATION: (88)..(162)
<223> OTHER INFORMATION: "CAG" repeat region associated with spinal
      cerebellar ataxia 1 (SCA-1)
<220> FEATURE:
<221> NAME/KEY: repeat_region
<222> LOCATION: (244)..(261)
<223> OTHER INFORMATION: His-6 "tag" region

<400> SEQUENCE: 8
gactttactt gtacgtgcat aatacgactc actataggga gactgaac                48 atg ggc agt ctg agc cag acg ccg gga cac aag gct gag cag cag cag    96
Met Gly Ser Leu Ser Gln Thr Pro Gly His Lys Ala Glu Gln Gln Gln
1               5                   10                  15 cag cag cag cag cag cag cag cag cag cat cag cat cag cag cag cag   144
Gln Gln Gln Gln Gln Gln Gln Gln Gln His Gln His Gln Gln Gln Gln
            20                  25                  30 cag cag cag cag cag cag cac ctc acg agg gct ccg ggc ctc atc acc   192
Gln Gln Gln Gln Gln Gln His Leu Ser Arg Ala Pro Gly Leu Ile Thr
        35                  40                  45 ccg ggt ccc ccc cac cag ccc agc aga acc agt acg tcc aca ttt caa   240
Pro Gly Pro Pro His Gln Pro Ser Arg Thr Ser Thr Ser Thr Gly Gln
    50                  55                  60

```
gtt cat cat cat cat cat cat tgagaatca                                    270
Val His His His His His His
 65              70
```

<210> SEQ ID NO 9
<211> LENGTH: 71
<212> TYPE: PRT
<213> ORGANISM: Homo sapiens
<220> FEATURE:
<221> NAME/KEY: REPEAT
<222> LOCATION: (14)..(38)
<223> OTHER INFORMATION: "Gln" repeat region associated with spinal
      cerebellar ataxia 1 (SCA-1)
<220> FEATURE:
<221> NAME/KEY: REPEAT
<222> LOCATION: (66)..(71)
<223> OTHER INFORMATION: His-6 "tag"

<400> SEQUENCE: 9

```
Met Gly Ser Leu Ser Gln Thr Pro Gly His Lys Ala Glu Gln Gln Gln
 1               5                  10                  15

Gln Gln Gln Gln Gln Gln Gln Gln Gln His Gln His Gln Gln Gln Gln
            20                  25                  30

Gln Gln Gln Gln Gln Gln His Leu Ser Arg Ala Pro Gly Leu Ile Thr
        35                  40                  45

Pro Gly Pro Pro Gly Gln Pro Ser Arg Thr Ser Thr Ser Thr Gly Gln
     50                  55                  60

Val His His His His His His
 65              70
```

MASS SPECTROMETRIC DETECTION OF POLYPEPTIDES

This application is a continuation-in-part of U.S. application Ser. No. 08/922,201, filed Sep. 2, 1997, to Daniel P. Little, Scott Higgins and Hubert Köster, entitled "DIAGNOSTICS BASED ON MASS SPECTROMETRIC DETECTION OF TRANSLATED TARGET POLYPEPTIDES." The subject matter of this application is herein incorporated by reference in its entirety.

FIELD OF THE INVENTION

The disclosed processes and kits relate generally to the field of proteomics and molecular medicine, and more specifically to processes using mass spectrometry to determine the identity of a target polypeptide.

BACKGROUND

In recent years, the molecular biology of a number of human genetic diseases has been elucidated by the application of recombinant DNA technology. More than 3000 diseases are known to be of genetic origin (Cooper and Krawczak, "Human Genome Mutations" (BIOS Publ. 1993)), including, for example, hemophilias, thalassemias, Duchenne muscular dystrophy, Huntington's disease, Alzheimer's disease and cystic fibrosis, as well as various cancers such as breast cancer. In addition to mutated genes that result in genetic disease, certain birth defects are the result of chromosomal abnormalities, including, for example, trisomy 21 (Down's syndrome), trisomy 13 (Patau syndrome), trisomy 18 (Edward's syndrome), monosomy X (Turner's syndrome) and other sex chromosome aneuploidies such as Klinefelter's syndrome (XXY).

Other genetic diseases are caused by an abnormal number of trinucleotide repeats in a gene. These diseases include Huntington's disease, prostate cancer, spinal cerebellar ataxia 1 (SCA-1), Fragile X syndrome (Kremer et al., *Science* 252:1711–14 (1991); Fu et al., *Cell* 67:1047–58 (1991); Hirst et al., *J. Med. Genet.* 28:824–29 (1991)); myotonic dystrophy type I (Mahadevan et al., *Science* 255:1253–55 (1992); Brook et al, *Cell* 68:799–808 (1992)), Kennedy's disease (also termed spinal and bulbar muscular atrophy (La Spada et al., *Nature* 352:77–79 (1991)), Machado-Joseph disease, and dentatorubral and pallidolyusian atrophy. The aberrant number of triplet repeats can be located in any region of a gene, including a coding region, a non-coding region of an exon, an intron, or a regulatory element such as a promoter. In certain of these diseases, for example, prostate cancer, the number of triplet repeats is positively correlated with prognosis of the disease.

Evidence indicates that amplification of a trinucleotide repeat is involved in the molecular pathology in each of the disorders listed above. Although some of these trinucleotide repeats appear to be in non-coding DNA, they clearly are involved with perturbations of genomic regions that ultimately affect gene expression. Perturbations of various dinucleotide and trinucleotide repeats resulting from somatic mutation in tumor cells also can affect gene expression or gene regulation.

Additional evidence indicates that certain DNA sequences predispose an individual to a number of other diseases, including diabetes, arteriosclerosis, obesity, various autoimmune diseases and cancers such as colorectal, breast, ovarian and lung cancer. Knowledge of the genetic lesion causing or contributing to a genetic disease allows one to predict whether a person has or is at risk of developing the disease or condition and also, at least in some cases, to determine the prognosis of the disease.

Numerous genes have polymorphic regions. Since individuals have any one of several allelic variants of a polymorphic region, each can be identified based on the type of allelic variants of polymorphic regions of genes. Such identification can be used, for example, for forensic purposes. In other situations, it is crucial to know the identity of allelic variants in an individual. For example, allelic differences in certain genes such as the major histocompatibility complex (MHC) genes are involved in graft rejection or graft versus host disease in bone marrow transplantation. Accordingly, it is highly desirable to develop rapid, sensitive, and accurate methods for determining the identity of allelic variants of polymorphic regions of genes or genetic lesions.

Several methods are used for identifying of allelic variants or genetic lesions. For example, the identity of an allelic variant or the presence of a genetic lesion can be determined by comparing the mobility of an amplified nucleic acid fragment with a known standard by gel electrophoresis, or by hybridization with a probe that is complementary to the sequence to be identified. Identification, however, only can be accomplished if the nucleic acid fragment is labeled with a sensitive reporter function, for example, a radioactive ($^{32}$P, $^{35}$S), fluorescent or chemiluminescent reporter. Radioactive labels can be hazardous and the signals they produce can decay substantially over time. Non-radioactive labels such as fluorescent labels can suffer from a lack of sensitivity and fading of the signal when high intensity lasers are used. Additionally, labeling, electrophoresis and subsequent detection are laborious, time-consuming and error-prone procedures. Electrophoresis is particularly error-prone, since the size or the molecular weight of the nucleic acid cannot be correlated directly to its mobility in the gel matrix because sequence specific effects, secondary structures and interactions with the gel matrix cause artifacts in its migration through the gel.

Mass spectrometry has been used for the sequence analysis of nucleic acids (see, for example, Schram, *Mass Spectrometry of Nucleic Acid Components, Biomedical Applications of Mass Spectrometry* 34:203–287 (1 990); Crain, *Mass Spectrom. Rev.* 9:505–554 (1990); Murray, *J. Mass Spectrom. Rev.* 31:1203 (1996); Nordhoff et al., *J. Mass Spectrom.* 15:67 (1997)). In general, mass spectrometry provides a means of "weighing" individual molecules by ionizing the molecules in vacuo and making them "fly" by volatilization. Under the influence of electric and/or magnetic fields, the ions follow trajectories depending on their individual mass (m) and charge (z). For molecules with low molecular weight, mass spectrometry is part of the routine physical-organic repertoire for analysis and characterization of organic molecules by the determination of the mass of the parent molecular ion. In addition, by arranging collisions of this parent molecular ion with other particles such as argon atoms, the molecular ion is fragmented, forming secondary ions by collisionally activated dissociation (CAD); the fragmentation pattern/pathway very often allows the derivation of detailed structural information. Many applications of mass spectrometric methods are known in the art, particularly in the biosciences (see *Meth. Enzymol.*, Vol. 193, "Mass Spectrometry" (McCloskey, ed.; Academic Press, NY 1990; McLaffery et al., *Acc. Chem. Res.* 27:297–386 (1994); Chait and Kent, *Science* 257:1885–1894 (1992); Siuzdak, *Proc. Natl. Acad. Sci., USA* 91:11290–11297 (1994)), including methods for producing and analyzing biopolymer ladders (see, International PCT application No. WO 96/36732; U.S. Pat. No. 5,792,664). Despite the effort to apply mass spectrometry methods to the analysis of nucleic acid molecules, however, there are limitations, including physical and chemical properties of nucleic acids. Nucleic acids are very polar biopolymers that are difficult to volatilize.

Accordingly, a need exists for methods to determine the identity of a nucleic acid molecules, particularly genetic lesions in a nucleic acid molecule, using alternative methodologies. Therefore it is an object herein to provide processes and compositions that satisfy this need and provide additional advantages.

SUMMARY OF THE INVENTION

Processes and kits for determining the identity of a target polypeptide by mass spectrometry are provided. The processes include the steps of determining the molecular mass of a target polypeptide or a fragment or fragments thereof by mass spectrometry, and then comparing the mass to a standard, whereby the identity of the polypeptide can be ascertained. Identity includes, but is not limited to, identifying the sequence of the polypeptide, identifying a change in a sequence compared to a known polypeptide, and other means by which polypeptides and mutations thereof can be identified. Selection of the standard will be determined as a function of the information desired.

One process for determining the identity of a target polypeptide includes the steps of a) obtaining a target polypeptide; b) determining the molecular mass of the target polypeptide by mass spectrometry, and c) by comparing the molecular mass of the target polypeptide with the molecular mass of a corresponding known polypeptide. By comparing the molecular mass of the target with a known polypeptide having a known structure, the identity of the target polypeptide can be ascertained. As disclosed herein, the polypeptide is obtained by methods including transcribing a nucleic acid encoding the target polypeptide into RNA and translating the RNA into the target polypeptide. If desired, transcription of the nucleic acid or translation of the RNA, or both, can be performed in vitro.

A process as disclosed herein also can include a step of amplifying a nucleic acid encoding the target polypeptide prior to step a), for example, by performing the polymerase chain reaction (PCR) using a forward primer and a reverse primer. The forward primer or the reverse primer can contain an RNA polymerase promoter such as an SP6 promoter, T3 promoter, or T7 promoter. In addition, a primer can contain a nucleotide sequence for a transcription start site. A primer also can encode a translation START (ATG) codon. Accordingly, a target polypeptide can be translated from a nucleic acid that is not naturally transcribed or translated in vivo, for example, by incorporating a START codon in the nucleic acid to be translated, thereby providing a translation reading frame. Furthermore, a primer can contain a nucleotide sequence, or complement thereof, encoding a second peptide or polypeptide, for example, a tag peptide such as a myc epitope tag, a *Haemophilus influenza* hemagglutinin peptide tag, a polyhistidine sequence, a polylysine sequence or a polyarginine sequence. A process as disclosed herein can be performed in vivo, for example, in a host cell such as a bacterial host cell transformed with a nucleic acid encoding a target polypeptide or a eukaryotic host cell such as a mammalian cell transfected with a nucleic acid encoding a target polypeptide.

A process as disclosed is performed using a mass spectrometric analysis, including for example, matrix assisted laser desorption ionization (MALDI), continuous or pulsed electrospray ionization, ionspray, thermospray, or massive cluster impact mass spectrometry and a detection format such as linear time-of-flight (TOF), reflectron time-of-flight, single quadruple, multiple quadruple, single magnetic sector, multiple magnetic sector, Fourier transform ion cyclotron resonance, ion trap, and combinations thereof such as MALDI-TOF spectrometry. An advantage of using a process as provided is that no radioactive label is required. Another advantage is that relatively short polypeptides can be synthesized from a target nucleic acid, thus providing an accurate measurement of molecular weight by mass spectrometry, as compared to analysis of the nucleic acid itself.

An RNA molecule encoding a target polypeptide can be translated in a cell-free extract, which can be a eukaryotic cell-free extract such as a reticulocyte lysate, a wheat germ extract, or a combination thereof; or a prokaryotic cell-free extract, for example, a bacterial cell extract such as an *E. coli* S30 extract. If desired, translation and transcription of a target nucleic acid can be performed in the same cell-free extract, for example, a reticulocyte lysate or a prokaryotic cell extract.

A target polypeptide generally is isolated prior to being detected by mass spectrometric analysis. For example, the polypeptide can be isolated from a cell or tissue obtained from a subject such as a human. The target polypeptide can be isolated using a reagent that interacts specifically with the target polypeptide, for example, an antibody that interacts specifically with the target polypeptide, or the target polypeptide can be fused to a tag peptide and isolated using a reagent that interacts specifically with the tag peptide, for example, an antibody specific for the tag peptide. A reagent also can be another molecule that interacts specifically with the tag peptide, for example, metal ions such as nickel or cobalt ions, which interact specifically with a hexahistidine (His-6) tag peptide.

A target polypeptide can be immobilized to a solid support, such as a bead or a microchip, which can be a flat surface or a surface with structures made of essentially any material commonly used for fashioning such a device. A microchip is useful, for example, for attaching moieties in an addressable array. Immobilization of a target polypeptide provides a means to isolate the polypeptide, as well as a means to manipulate the isolated target polypeptide prior to mass spectrometry.

Methods are provided for sequencing an immobilized target polypeptide, including sequencing from the carboxyl terminus or from the amino terminus. Furthermore, methods of determining the identity of each of the target polypeptides in a plurality of target polypeptides by multiplexing are provided.

In particular embodiments, post translational capture and immobilization of a target polypeptide via a cleavable linker are provided in order to orthogonally sequence a polypeptide. These methods can include: 1) obtaining the target polypeptide; 2) immobilizing the target polypeptide to a solid surface; 3) treating the immobilized target polypeptide with an enzyme or chemical in a time dependent manner to generate a series of deleted fragments; 4) the cleaved polypeptide fragments are conditioned; 5) cleaving the linker and thereby releasing the immobilized fragments; 6) determining the mass of the release fragments; and 7) aligning the masses of each of the polypeptide fragments to determine the amino acid sequence. Variants of these methods in which one or more steps are combined or eliminated are also contemplated.

In one embodiment, the second step includes immobilizing the amino terminal portion of the polypeptide to a solid support via a photocleavable linker. In a more preferred embodiment, the solid support is activated as described in FIG. 2 and allowed to react with the amino group of a target polypeptide.

In another embodiment, the second step includes comprises immobilizing the carboxy terminal portion of the polypeptide to a solid support via a photocleavable linker. In a more preferred embodiment, a photocleavable linker is a linker that can be cleaved from the solid support with light. In a more preferred embodiment, the solid support is activated as described in FIG. 3 and allowed to react with the carboxy group of a target polypeptide.

In another embodiment, the second step includes immobilizing either the carboxy or amino termini of group of different polypeptides to a solid support in an array format via a photocleavable linker. In a more preferred embodiment, discrete areas of a silicon surface are activated with the chemistry describe din FIG. 2 and an array composed of from 2 to 999 positions.

In another embodiment, the second step includes immobilizing the amino terminal portion of the polypeptide to a solid support via a cleavable linker. In a more preferred embodiment, a cleavable linker is a silyl linker that can be cleaved from the solid support. In a more preferred embodiment, the solid support is activated as described in FIG. 2 and allowed to react with the amino group of a target polypeptide.

In another embodiment, the second step includes immobilizing the carboxy terminal portion of the polypeptide to a solid support via a cleavable linker. In a more preferred embodiment, a cleavable linker is a silyl linker that can be cleaved from the solid support. In a more preferred embodiment, the solid support is activated as described in FIG. 3 and allowed to react with the carboxy group of a target polypeptide.

In another embodiment, the second step includes immobilizing either the carboxy or the amino termini of group of different polypeptides to a solid support in an array format via a cleavable linker. In a more preferred embodiment, discrete areas of a silicon surface are activated with the chemistry described in FIG. 2, thereby forming an array, preferably composed of from 2 to 999 positions.

In another embodiment, the third step includes immobilizating the amino terminal end of the target polypeptide(s) to the solid support and treating with an exopeptidase. In a preferred embodiment, exopeptidase digestion is carried out in a time dependent manner to generate a nested group of immobilized polypeptide fragments of varying lengths. In a more preferred embodiment, exopeptidase is selected from a group of one or more mono-peptidases and polypeptidases including carboxypeptidase Y, carboxpeptidase P, carboxypeptidase A, carboxypeptidase G and carboxypeptidase B.

In another embodiment, the exopeptidase is selected from a group of one or more mono-peptidases and polypeptidases including aminopeptidases including alanine aminopeptidase, leucine aminopeptidase, pyroglutamate peptidase, dipeptidyl peptidase, microsomal peptidase and other enzymes which progressive digest the animo terminal end of a polypeptidase.

In another embodiment, the third step comprises a step where exopeptidase digestion is carried out under reaction conditions that remove any secondary or tertiary structure, leaving the terminal residues of the polypeptide inaccessible to exopeptidases. In a preferred embodiment, the reaction conditions expose the terminus of a target polypeptide(s) to temperatures over about 70 ° C. and below about 100 ° C. In a more preferred embodiment, the exopeptidase is a thermostable carboxypeptidase or aminopeptidase. In another preferred embodiment, the reaction conditions expose the terminus of a target polypeptide(s) to high ionic strength conditions. In a more preferred embodiment, the exopeptidase is a salt tolerant carboxypeptidase or aminopeptidase.

In another embodiment, the second step includes conditioning of polypeptide after enzymatic treatment or purification. In a more preferred embodiment, methods of conditioning include methods that prepare the polypeptide or polypeptide fragments in a manner that generally improves mass spectrometric analysis. In a more preferred embodiment, conditioning may include cation exchange.

Kits containing components useful for determining the identity of a target polypeptide based on a process as disclosed herein also are provided. Such a kit can contain, reagents for in vitro transcription and/or translation of the amplified nucleic acid to obtain the target polypeptide; optionally, a reagent for isolating the target polypeptide; and instructions for use in determining the identity of a target polypeptide by mass spectrometric analysis. The kits may also include, for example, forward or reverse primers capable of hybridizing to a nucleic acid encoding the target polypeptide and amplifying the nucleic acid. Such kits also can contain an organic or inorganic solvent, for example, a salt of ammonium, or a reagent system for volatilizing and ionizing the target polypeptide prior to mass spectrometric analysis. In addition, a kit can contain a control nucleic acid or polypeptide of known identity. A kit also can provide, for example, a solid support for immobilizing a target polypeptide, including, if desired, reagents for performing such immobilization. A kit further can contain reagents useful for manipulating a target polypeptide, for example, reagents for conditioning the target polypeptide prior to mass spectrometry or reagents for sequencing the polypeptide. A kit as disclosed herein is useful for performing the various disclosed processes and can be designed, for example, for use in determining the number of nucleotide repeats of a target nucleic acid or whether a target nucleic acid contains a different number of nucleotide repeats relative to a reference nucleic acid.

A target polypeptide can be encoded by an allelic variant of a polymorphic region of a gene of a subject, or can be encoded by an allelic variant of a polymorphic region that is located in a chromosomal region that is not in a gene. A process as disclosed herein can include a step of determining whether the allelic variant is identical to an allelic variant of a polymorphic region that is associated with a disease or condition, thereby indicating whether a subject has or is at risk of developing the disease or condition associated with the specific allelic variant of the polymorphic region of the gene. The disease or condition can be associated, for example, with an abnormal number of nucleotide repeats, for example, dinucleotide, trinucleotide, tetranucleotide or pentanucleotide repeats. Since trinucleotide repeats, for example, can be very long, determination of the number of trinucleotide repeats by analyzing the DNA directly would not be straightforward. Since a process for determining the identity of a target polypeptide as disclosed herein is based on the analysis of a polypeptide, particularly a polypeptide encoded essentially by trinucleotide repeats, determination of the number of trinucleotide repeats will be more accurate using the disclosed processes and kits. A disease or condition that can be identified using a disclosed process or kit includes, for example, Huntington's disease, prostate cancer, Fragile X syndrome type A, myotonic dystrophy type I Kennedy's disease, Machado-Joseph disease, dentatorubral and pallidolyusian atrophy, and spino bulbar muscular atrophy; as well as aging, which can be identified by examining the number of nucleotide repeats in telomere nucleic acid from a subject. The disease or condition also can be associated with a gene such as genes encoding BRCA1, BRCA2, APC; a gene encoding dystrophin, β-globin, Factor IX, Factor VIIc, ornithine-d-amino-transferase, hypoxanthine guanine phosphoribosyl transferase, or the cystic fibrosis transmembrane receptor (CFTR); or a proto-oncogene.

A process or a kit as disclosed herein can be used to genotype a subject by determining the identity of one or more allelic variants of one or more polymorphic regions in one or more genes or chromosomes of the subject. For example, the one or more genes can be associated with graft rejection and the process can be used to determine compatibility between a donor and a recipient of a graft. Such genes can be MHC genes, for example. Genotyping a subject using a process as provided herein can be used for forensic or identity testing purposes and the polymorphic regions can be present in mitochondrial genes or can be short tandem repeats.

A disclosed process or kit also can be used to determine whether a subject carries a pathogenic organism such as a virus, bacterium, fungus or protist. A process for determining the isotype of a pathogenic organism also is provided. Thus, depending on the sequence to be detected, the processes and kits disclosed herein can be used, for example, to diagnose a genetic disease or chromosomal abnormality; a predisposition to or an early indication of a gene influenced disease or condition, for example, obesity, atherosclerosis, diabetes or cancer; or an infection by a pathogenic organism, for example, a virus, bacterium, parasite or fungus; or to provide information relating to identity, heredity or compatibility using, for example, mini-satellite or micro-satellite sequences or HLA phenotyping.

A process as disclosed herein provides a means for determining the amino acid sequence of a polypeptide of interest. Such a process can be performed, for example, by using mass spectrometry to determine the identity of an amino acid residue released from the amino terminus or the carboxyl terminus of a polypeptide of interest. Such a process also can be performed, for example, by producing a nested set of carboxyl terminal or amino terminal deletion fragments of a polypeptide of interest, or peptide fragment thereof, and subjecting the nested set of deletion fragments to mass spectrometry, thereby determining the amino acid sequence of the polypeptide.

A process of determining the amino acid sequence of a polypeptide of interest can be performed, for example, using a polypeptide that is immobilized, reversibly, if desired, to a solid support. In addition, such a process can be performed on a plurality of such polypeptides, which can be, for example, a plurality of target polypeptides immobilized in an addressable array on a solid support such as a microchip, which can contain, for example, at least 2 positions, and as many as 999 positions, or 1096 positions, or 9999 positions, or more. In general, a target polypeptide, or the amino acids released therefrom, are conditioned prior to mass spectrometry, thereby increasing resolution of the mass spectrum. For example, a target polypeptide can be conditioned by mass modification. In addition, the amino acid sequences of a plurality of mass modified target polypeptide can be determined by mass spectrometry using a multiplexing format.

BRIEF DESCRIPTION OF THE DRAWINGS

FIG. 1A shows the nucleotide sequence of a nucleic acid (SEQ ID NO: 8) that can be obtained by PCR amplification of DNA containing a non-variable stretch of 12 CAG repeats (shown without italics) and a variable repeat of 10 CAG repeat units (represented in italics) with primers (underlined) having the sequence (forward primer) or the complement of the sequence (reverse primer). The T7 promoter sequence and the sequence encoding a hexahistidine (His-6) peptide are represented in bold.

FIG. 1B shows the sequence (SEQ ID NO: 9) of the 71 amino acid polypeptide encoded by the nucleic acid sequence shown in FIG. 1A. The stretch of 10 variable glutamine (Q) residues encoded by the trinucleotide repeats is represented in italics. The His-6 peptide is represented in bold.

FIG. 3 provides reaction conditions for conjugating a polypeptide by its carboxyl terminus to a solid support using 1-ethyl-3-(3-dimethylamino-propyl) carbodiimide hydrochloride (EDC)/N-hydroxy succinimidyl (NHS).

DETAILED DESCRIPTION OF THE INVENTION

Definitions

Figure 2:
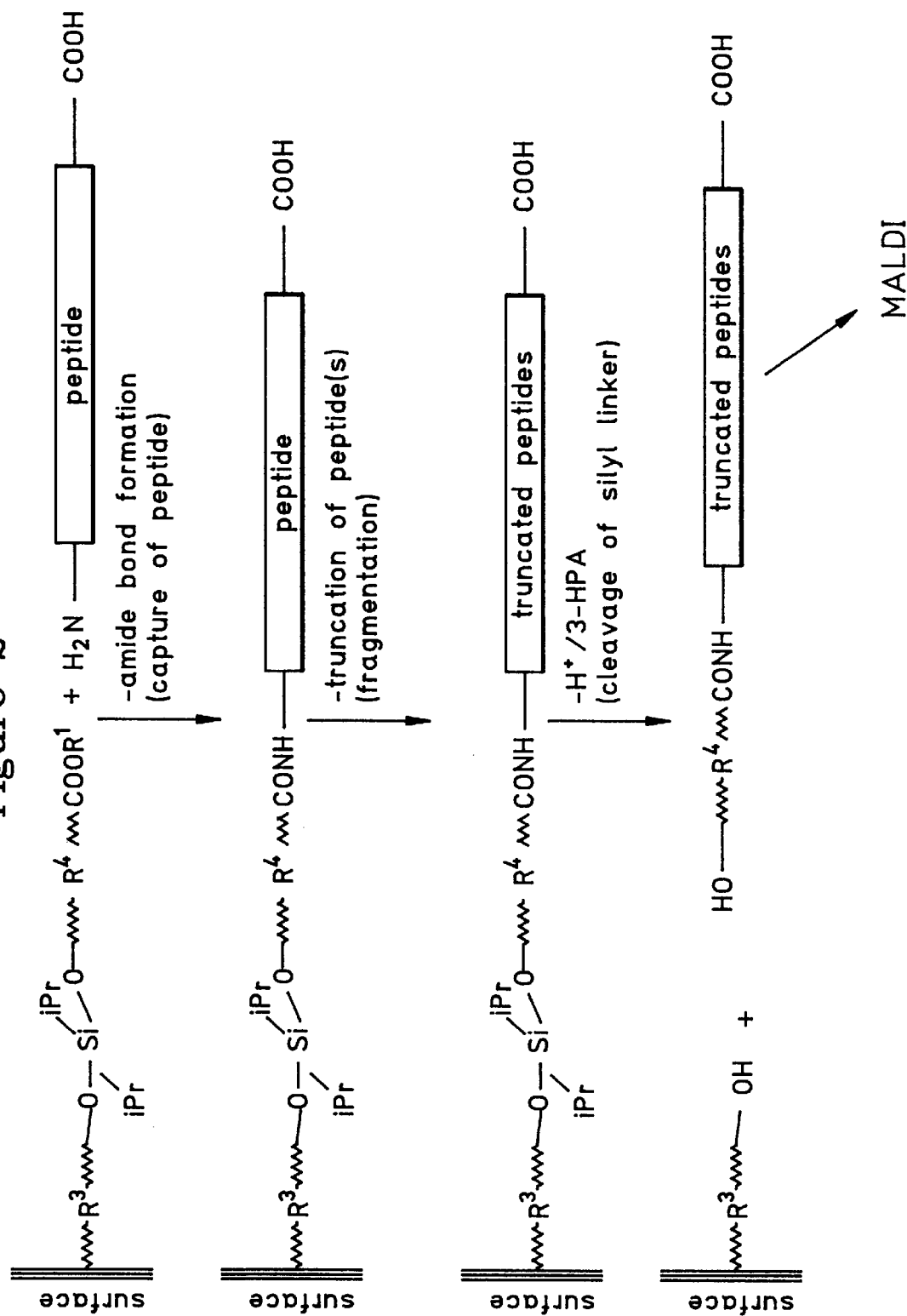
FIG. 2 sets forth an exemplary scheme for orthogonal capture, cleavage and MALDI analysis of a polypeptide. The peptide is conjugated to a solid surface, which can be a microchip, through the use of an acid cleavable diisopropylysilyl linker. The peptide is conjugated to the linker at its amino terminus through the formation of an amide bond. The immobilized polypeptide can be truncated, for example, using a carboxypeptidase, or can be cleaved using an endopeptidase such as trypsin, then is cleaved from the solid support by exposure to acidic conditions such as the 3-HPA (3-hydroxypicolinic acid) matrix solution. The cleaved polypeptide then is subjected to mass spectrometry, for example, MALDI.

Unless defined otherwise, all technical and scientific terms used herein have the same meaning as is commonly understood by one of skill in the art to which this invention belongs. All patents, applications and publications referred to herein are incorporated by reference. For convenience, the meaning of certain terms and phrases used in the specification and claims are provided.

As used herein, the term "allele" refers to an alternative form of a nucleotide sequence in a chromosome. Reference to an "allele" includes a nucleotide sequence in a gene or a portion thereof, as well as a nucleotide sequence that is not a gene sequence. Alleles occupy the same locus or position on homologous chromosomes. A subject having two identical alleles of a gene is considered "homozygous" for the allele, whereas a subject having two different alleles is considered "heterozygous." Alleles of a specific nucleotide sequence, for example, of a gene can differ from each other in a single nucleotide, or several nucleotides, where the difference can be due to a substitution, deletion, or insertion of one or more nucleotides. A form of a gene containing a mutation is an example of an allele. In comparison, a wild-type allele is an allele that, when present in two copies in a subject, results in a wild-type phenotype. There can be several different wild-type alleles of a specific gene, since certain nucleotide changes in a gene may not affect the phenotype of a subject having two copies of the gene with the nucleotide changes.

The term "allelic variant" refers to a portion of an allele containing a polymorphic region in the chromosomal nucleic acid. The term "allelic variant of a polymorphic region of a gene" refers to a region of a gene having one of several nucleotide sequences found in that region of the gene in different individuals. The term "determining the identity of an allelic variant of a polymorphic region" refers to the determination of the nucleotide sequence or encoded amino acid sequence of a polymorphic region, thereby determining to which of the possible allelic variants of a polymorphic region that particular allelic variant corresponds.

The term "polymorphism" refers to the coexistence, in a population, of more than one form of an allele. A polymorphism can occur in a region of a chromosome not associated with a gene or can occur, for example, as an allelic variant or a portion thereof of a gene. A portion of a gene that exists in at least two different forms, for example, two different nucleotide sequences, is referred to as a "polymorphic region of a gene." A polymorphic region of a gene can be localized to a single nucleotide, the identity of which differs in different alleles, or can be several nucleotides long.

As used herein, the term "biological sample" refers to any material obtained from a living source, for example, an animal such as a human or other mammal, a plant, a bacterium, a fungus, a protist or a virus. The biological sample can be in any form, including a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells.

The term "polypeptide," as used herein, means at least two amino acids, or amino acid derivatives, including mass modified amino acids, that are linked by a peptide bond, which can be a modified peptide bond. A polypeptide can be translated from a nucleotide sequence that is at least a portion of a coding sequence, or from a nucleotide sequence that is not naturally translated due, for example, to its being in a reading frame other than the coding frame or to its being an intron sequence, a 3' or 5' untranslated sequence, or a regulatory sequence such as a promoter. A polypeptide also can be chemically synthesized and can be modified by chemical or enzymatic methods following translation or chemical synthesis. The terms "protein," "polypeptide" and "peptide" are used interchangeably herein when referring to a translated nucleic acid, for example, a gene product.

As used herein, the phrase "determining the identity of a target polypeptide" refers to determining at least one characteristic of the polypeptide, for example, the molecular mass or charge, or the identity of at least one amino acid, or identifying a particular pattern of peptide fragments of the target polypeptide. Determining the identity of a target polypeptide can be performed, for example, by using mass spectrometry to determine the amino acid sequence of at least a portion of the polypeptide, or to determine the patter of peptide fragments of the target polypeptide produced, for example, by treatment of the polypeptide with one or more endopeptidases.

In determining the identity of a target polypeptide, the number of nucleotide repeats encoding the target polypeptide can be quantified. As used herein, the term "quantify," when used in reference to nucleotide repeats encoding a target polypeptide, means a determination of the exact number of nucleotide repeats present in the nucleotide sequence encoding the target polypeptide. As disclosed herein, the number of nucleotide repeats, for example, trinucleotide repeats, can be quantified by using mass spectrometry to determine the number of amino acids, which are encoded by the repeat, that are present in the target polypeptide. It is recognized, however, that the number of nucleotide repeats encoding a target polypeptide need not be quantified to determine the identity of a target polypeptide, since a measure of the relative number of amino acids encoded by a region of nucleotide repeats also can be used to determine the identity of the target polypeptide by comparing the mass spectrum of the target polypeptide with that of a corresponding known polypeptide.

As used herein, the term "nucleotide repeats" refers to any nucleotide sequence containing tandemly repeated nucleotides. Such tandemly repeated nucleotides can be, for example, tandemly repeated dinucleotide, trinucleotide, tetranucleotide or pentanucleotide sequences, or any tandem array of repeated units.

As used herein, a reference polypeptide is a polypeptide to which the target polypeptide is compared in order to identify the polypeptide in methods that do not involve sequencing the polypeptide. Reference polypeptides typically are known polypeptides.

As used herein, the term "conditioned" or "conditioning," when used in reference to a polypeptide, particularly a target polypeptide, means that the polypeptide is modified so as to decrease the laser energy required to volatilize the polypeptide, to minimize the likelihood of fragmentation of the polypeptide, or to increase the resolution of a mass spectrum of the polypeptide or of the component amino acids. Resolution of a mass spectrum of a target polypeptide can be increased by conditioning the polypeptide prior to performing mass spectrometry. Conditioning can be performed at any stage prior to mass spectrometry and, in particular, can be performed while the polypeptide is immobilized. A polypeptide can be conditioned, for example, by treating the polypeptide with a cation exchange material or an anion exchange material, which can reduce the charge heterogeneity of the polypeptide, thereby for eliminating peak broadening due to heterogeneity in the number of cations (or anions) bound to the various polypeptides in a population. Contacting a polypeptide with an alkylating agent such as alkyliodide, iodoacetamide, iodoethanol, or 2,3-epoxy-1-propanol, the formation of disulfide bonds, for example, in a polypeptide can be prevented. Likewise, charged amino acid side chains can be converted to uncharged derivatives employing trialkylsilyl chlorides.

Conditioning of proteins is generally unnecessary because proteins are relatively stable under acidic, high energy conditions so that proteins do not require conditioning for mass spectrometric analyses. There are means of improving resolution, however, particularly for shorter peptides, such as by incorporating modified amino acids that are more basic than the corresponding unmodified residues. Such modification in general increases the stability of the polypeptide during mass spectrometric analysis. Also, cation exchange chromatography, as well as general washing and purification procedures which remove proteins and other reaction mixture components away from the target polypeptide, can be used to clean up the peptide after in vitro translation and thereby increase the resolution of the spectrum resulting from mass spectrometric analysis of the target polypeptide.

As used herein, delayed extraction, refers to methods in which conditions are selected to permit a longer optimum extraction delay and hence a longer residence time, which results in increased resolution (see, e.g., Juhasz et al. (1996) *Analysis, Anal. Chem.* 68:941–946; and Vestal et al. (1995) *Rapid Communications in Mass Spectrometry* 9:1044–1050; see also, e.q., U.S. Pat. Nos. 5,777,325, 5,742,049, 5,654, 545, 5,641,959, 5,654,545 and 5,760,393 for descriptions of MALDI and delayed extraction protocols). In particular, delayed ion extraction is a technique whereby a time delay is introduced between the formation of the ions and the application of the accelerating field. During the time lag, the ions move to new positions according to their initial velocities. By properly choosing the delay time and the electric fields in the acceleration region, the time of flight of the ions can be adjusted so as to render the flight time independent of the initial velocity to the first order. For example, a particular method involves exposure of the target polypeptide sample to an electric field before and during the ionization process, which results in a reduction of background signal due to the matrix, induces fast fragmentation and controls the transfer of energy prior to ion extraction.

As used herein, the term "multiplexing" refers to simultaneously determining the identity of at least two target polypeptides by mass spectrometry. For example, where a population of different target polypeptides are present in an array on a microchip or are present on another type of solid support, multiplexing can be used to determine the identity of a plurality of target polypeptides. Multiplexing can be performed, for example, by differentially mass modifying each different polypeptide of interest, then using mass spectrometry to determine the identity of each different polypeptide. Multiplexing provides the advantage that a plurality of target polypeptides can be identified in as few as a single mass spectrum, as compared to having to perform a separate mass spectrometry analysis for each individual target polypeptide.

As used herein, the term "plurality," when used in reference to a polynucleotide or to a polypeptide, means two or more polynucleotides or polypeptides, each of which has a different nucleotide or amino acid sequence, respectively. Such a difference can be due to a naturally occurring variation among the sequences, for example, to an allelic variation in a nucleotide or an encoded amino acid, or can be due to the introduction of particular modifications into various sequences, for example, the differential incorporation of mass modified amino acids into each polypeptide in a plurality.

As used herein, "in vitro transcription system" refers to a cell-free system containing an RNA polymerase and other factors and reagents necessary for transcription of a DNA molecule operably linked to a promoter that specifically binds an RNA polymerase. An in vitro transcription system can be a cell extract, for example, a eukaryotic cell extract. The term "transcription," as used herein, generally means the process by which the production of RNA molecules is initiated, elongated and terminated based on a DNA template. In addition, the process of "reverse transcription," which is well known in the art, is considered as encompassed within the meaning of the term "transcription" as used herein. Transcription is a polymerization reaction that is catalyzed by DNA-dependent or RNA-dependent RNA polymerases. Examples of RNA polymerases include the bacterial RNA polymerases, SP6 RNA polymerase, T3 RNA polymerase, T3 RNA polymerase, and T7 RNA polymerase.

As used herein, the term "translation" describes the process by which the production of a polypeptide is initiated, elongated and terminated based on an RNA template. For a polypeptide to be produced from DNA, the DNA must be transcribed into RNA, then the RNA is translated due to the interaction of various cellular components into the polypeptide. In prokaryotic cells, transcription and translation are "coupled", meaning that RNA is translated into a polypeptide during the time that it is being transcribed from the DNA. In eukaryotic cells, including plant and animal cells, DNA is transcribed into RNA in the cell nucleus, then the RNA is processed into mRNA, which is transported to the cytoplasm, where it is translated into a polypeptide.

The term "translation system" refers to a cellular or cell-free system for performing a translation reaction. The term "cellular translation system" refers to a translation system based on a permeabilized cell; the term "cell-free translation system" or "in vitro translation system" refers to a cell extract or a reconstituted translation system. The term "reconstituted translation system" refers to a system containing purified or partially purified translation factors such as elongation factors. An in vitro translation system contains at least the minimum elements necessary for translation of an RNA molecule into a polypeptide. An in vitro translation system, which can be a eukaryotic or prokaryotic system, typically contains ribosomes, tRNA molecules, rRNA, an initiator methionyl-tRNA$^{Met}$, proteins or complexes involved in translation, for example, eukaryotic initiation factor 2 (eIF$_2$), eIF$_3$ and eIF$_{4F}$, and the cap-binding complex, including the cap-binding protein.

The term "isolated" as used herein with respect to a nucleic acid, including DNA and RNA, refers to nucleic acid molecules that are substantially separated from other macromolecules normally associated with the nucleic acid in its natural state. An isolated nucleic acid molecule is substantially separated from the cellular material normally associated with it in a cell or, as relevant, can be substantially separated from bacterial or viral material; or from culture medium when produced by recombinant DNA techniques; or from chemical precursors or other chemicals when the nucleic acid is chemically synthesized. In general, an isolated nucleic acid molecule is at least about 50% enriched with respect to its natural state, and generally is about 70% to about 80% enriched, particularly about 90% or 95% or more. Preferably, an isolated nucleic acid constitutes at least about 50% of a sample containing the nucleic acid, and can be at least about 70% or 80% of the material in a sample, particularly at least about 90% to 95% or greater of the sample. An isolated nucleic acid can be a nucleic acid fragment that does not occur in nature and, therefore, is not found in a natural state.

The term "isolated" also is used herein to refer to polypeptides that are substantially separated from other macromolecules normally associated with the polypeptide in its natural state. An isolated polypeptide can be identified based on its being enriched with respect to materials it naturally is associated with or its constituting a fraction of a sample containing the polypeptide to the same degree as defined above for an "isolated" nucleic acid, i.e., enriched at least about 50% with respect to its natural state or constituting at least about 50% of a sample containing the polypeptide. An isolated polypeptide, for example, can be purified from a cell that normally expresses the polypeptide or can produced using recombinant DNA methodology.

As used herein, the term "nucleic acid" refers to a polynucleotide, including a deoxyribonucleic acid (DNA), a ribonucleic acid (RNA), and an analog of DNA or RNA containing, for example, a nucleotide analog or a "backbone" bond other than a phosphodiester bond, for example, a phosphotriester bond, a thioester bond, or a peptide bond (peptide nucleic acid). A nucleic acid can be single stranded or double stranded and can be, for example, a DNA-RNA hybrid. A nucleic acid also can be a portion of a longer nucleic acid molecule, for example, a portion of a gene containing a polymorphic region. The molecular structure of a nucleotide sequence, for example, a gene or a portion thereof, is defined by its nucleotide content, including deletions, substitutions or additions of one or more nucleotides; the nucleotide sequence; the state of methylation; or any other modification of the nucleotide sequence.

Reference to a nucleic acid as a "polynucleotide" is used in its broadest sense to mean two or more nucleotides or nucleotide analogs linked by a covalent bond, including single stranded or double stranded molecules. The term "oligonucleotide" also is used herein to mean two or more nucleotides or nucleotide analogs linked by a covalent bond, although those in the art will recognize that oligonucleotides such as PCR primers generally are less than about fifty to one hundred nucleotides in length. The term "amplifying," when used in reference to a nucleic acid, means the repeated copying of a DNA sequence or an RNA sequence, through the use of specific or non-specific means, resulting in an increase in the amount of the specific DNA or RNA sequences intended to be copied.

A process as disclosed herein can be used to determine a nucleotide sequence of an unknown polynucleotide by comparing the amino acid sequence of a polypeptide encoded by the unknown polynucleotide with the amino acid sequence of a polypeptide encoded by a corresponding known polynucleotide. The determined nucleotide sequence of the unknown polynucleotide can be the same as a naturally occurring nucleotide sequence encoding the polypeptide, or can be different from the naturally occurring sequence due to degeneracy of the genetic code.

As used herein, the term "unknown polynucleotide" refers to a polynucleotide, the encoded polypeptide of which is being examined by mass spectrometry. Generally, an unknown polynucleotide is obtained from a biological sample. The term "corresponding known polynucleotide" means a defined counterpart of the unknown polynucleotide. A corresponding known polynucleotide generally is used as a control for comparison to the unknown polynucleotide and can be, for example, the nucleotide sequence of an allele of the unknown polynucleotide that is present in the majority of subjects in a population. For example, an "unknown polynucleotide" can be a DNA sequence that is obtained from a prostate cancer patient and includes the polymorphic region that demonstrates amplification of a trinucleotide sequence associated with prostate cancer, and the "corresponding known polynucleotide" can be the same polymorphic region from a subject that does not have prostate cancer, for example, from a female subject. An unknown polynucleotide also can be mutated gene, which can alter the phenotype of a subject as compared to a subject not having the mutated gene. A mutated gene can be recessive, dominant or codominant, as is well known in the art.

The term "plasmid" refers generally to a circular DNA sequence which, in its vector form, is not bound to a chromosome. The terms "plasmid" and "vector" are used interchangeably herein, since the plasmid is the most commonly used form of a vector. Vectors such as a lambda vector can be linear but, nevertheless, are included within the meaning of the term "plasmid" or "vector" as used herein. Expression vectors and other vectors serving equivalent functions, and that become known in the art subsequently hereto, are included within the meaning of the term "plasmid" or "vector" as used herein.

In general, a nucleic acid encoding a polypeptide of interest, for examples, a target polypeptide, is cloned into a plasmid and is operably linked to regulatory elements necessary for transcription or translation of the cloned nucleic acid. As used herein, the term "operably linked" means that a nucleic acid encoding a polypeptide is associated with a regulatory element, particularly a promoter, such that the regulatory element performs its function with respect to the nucleic acid molecule to which it is linked. For example, a promoter element that is operably linked to a nucleic acid allows for transcription of the nucleic acid when the construct is placed in conditions suitable for transcription to occur. It should be recognized that the term "regulatory element" is used broadly herein to include a nucleotide sequence, either DNA or RNA, that is required for transcription or translation, for example, a nucleotide sequence encoding a STOP codon or a ribosome binding site.

The term "target nucleic acid" refers to any nucleic acid of interest, including a portion of a larger nucleic acid such as a gene or an mRNA. A target nucleic acid can be a polymorphic region of a chromosomal nucleic acid, for example, a gene, or a region of a gene potentially having a mutation. Target nucleic acids include, but are not limited to, nucleotide sequence motifs or patterns specific to a particular disease and causative thereof, and to nucleotide sequences specific as a marker of a disease but not necessarily causative of the disease or condition. A target nucleic acid also can be a nucleotide sequence that is of interest for research purposes, but that may not have a direct connection to a disease or that may be associated with a disease or condition, although not yet proven so. A target nucleic acid can be any region of contiguous nucleotides that encodes a polypeptide of at least 2 amino acids, generally at least 3 or 4 amino acids, particularly at least 5 amino acids. A target nucleic acid encodes a target polypeptide.

The term "target polypeptide" refers to any polypeptide of interest that is subjected to mass spectrometry for the purposes disclosed herein, for example, for identifying the presence of a polymorphism or a mutation. A target polypeptide contains at least 2 amino acids, generally at least 3 or 4 amino acids, and particularly at least 5 amino acids. A target polypeptide can be encoded by a nucleotide sequence encoding a protein, which can be associated with a specific disease or condition, or a portion of a protein. A target polypeptide also can be encoded by a nucleotide sequence that normally does not encode a translated polypeptide. A target polypeptide can be encoded, for example, from a sequence of dinucleotide repeats or trinucleotide repeats or the like, which can be present in chromosomal nucleic acid, for example, a coding or a non-coding region of a gene, for example, in the telomeric region of a chromosome.

A process as disclosed herein also provides a means to identify a target polypeptide by mass spectrometric analysis of peptide fragments of the target polypeptide. As used herein, the term "peptide fragments of a target polypeptide" refers to cleavage fragments produced by specific chemical or enzymatic degradation of the polypeptide. The production of such peptide fragments of a target polypeptide is defined by the primary amino acid sequence of the polypeptide, since chemical and enzymatic cleavage occurs in a sequence specific manner. Peptide fragments of a target polypeptide can be produced, for example, by contacting the polypeptide, which can be immobilized to a solid support, with a chemical agent such as cyanogen bromide, which cleaves a polypeptide at methionine residues, or hydroxylamine at high pH, which can cleave an Asp-Gly peptide bond; or with an endopeptidase such as trypsin, which cleaves a polypeptide at Lys or Arg residues.

The identity of a target polypeptide can be determined by comparison of the molecular mass or sequence with that of a reference or known polypeptide. For example, the mass spectra of the target and known polypeptides can be compared.

As used herein, the term "corresponding or known polypeptide" is a known polypeptide generally used as a control to determine, for example, whether a target polypeptide is an allelic variant of the corresponding known polypeptide. It should be recognized that a corresponding known protein can have substantially the same amino acid sequence as the target polypeptide, or can be substantially different. For example, where a target polypeptide is an allelic variant that differs from a corresponding known protein by a single amino acid difference, the amino acid sequences of the polypeptides will be the same except for the single difference. Where a mutation in a nucleic acid encoding the target polypeptide changes, for example, the reading frame of the encoding nucleic acid or introduces or deletes a STOP codon, the sequence of the target polypeptide can be substantially different from that of the corresponding known polypeptide.

As disclosed herein, a target polypeptide can be isolated using a reagent that interacts specifically with the target polypeptide, with a tag peptide fused to the target polypeptide, or with a tag conjugated to the target polypeptide. As used herein, the term "reagent" means a ligand or a ligand binding molecule that interacts specifically with a particular ligand binding molecule or ligand, respectively. The term "tag peptide" is used herein to mean a peptide that is specifically bound by a reagent. The term "tag" refers more generally to any molecule that is specifically bound by a reagent and, therefore, includes a tag peptide. A reagent can be, for example, an antibody that interacts specifically with an epitope of a target polypeptide or an epitope of a tag peptide. For example, a reagent can be an anti-myc epitope antibody, which can interact specifically with a myc epitope fused to a target polypeptide. A reagent also can be, for example, a metal ion such as nickel ion or cobalt ion, which interacts specifically with a polyhistidine tag peptide; or zinc, copper or, for example, a zinc finger domain, which interacts specifically with an polyarginine or polylysine tag peptide; or a molecule such as avidin, streptavidin or a derivative thereof, which interacts specifically with a tag such as biotin or a derivative thereof (see, e.g., U.S. application Ser. No. 08/649,876. and also the corresponding published International PCT application No. WO 97/43617, which describe methods for dissociating biotin compounds, including biotin and biotin analogs conjugated (biotinylated) to the polypeptide, from biotin binding compounds, including avidin and streptavidin, using amines, particularly ammonia).

The term "interacts specifically," when used in reference to a reagent and the epitope, tag peptide or tag to which the reagent binds, indicates that binding occurs with relatively high affinity. As such, a reagent has an affinity of at least about $1\times10^6$ $M^{-1}$, generally, at least about $1\times10^7$ $M^{-1}$, and, in particular, at least about $1\times10^8$ $M^{-1}$, for the particular epitope, tag peptide or tag. A reagent the interacts specifically, for example, with a particular tag peptide primarily binds the tag peptide, regardless of whether other unrelated molecules are present and, therefore, is useful for isolating the tag peptide, particularly a target polypeptide fused to the tag peptide, from a sample containing the target polypeptide, for example, from an in vitro translation reaction.

It can be advantageous in performing a disclosed process to conjugate a nucleic acid, for example, a target nucleic acid, or a polypeptide, for example, a target polypeptide, to a solid support such as a bead, microchip, glass or plastic capillary, or any surface, particularly a flat surface, which can contain a structure such as wells, pins or the like. A nucleic acid or a polypeptide can be conjugated to a solid support by various means, including, for example, by a streptavidin or avidin to biotin interaction; a hydrophobic interaction; by a magnetic interaction using, for example, functionalized magnetic beads such as DYNABEADS, which are streptavidin coated magnetic beads (Dynal Inc.; Great Neck N.Y.; Oslo Norway); by a polar interaction such as a "wetting" association between two polar surfaces or between oligo/polyethylene glycol; by the formation of a covalent bond such as an amide bond, a disulfide bond, a thioether bond; through a crosslinking agent; and through an acid-labile or photocleavable linker (see, for example, Hermanson, "Bioconjugate Techniques" (Academic Press 1996)). In addition, a tag or a peptide such as a tag peptide can be conjugated to polypeptide of interest, particularly to a target polypeptide.

A process as disclosed herein can be useful for determining the amino acid sequence of a polypeptide of interest, for example, by using an agent that cleaves amino acids from a terminus of the polypeptide to produce a nested set of deletion fragments of the polypeptide and cleaved amino acids, and using mass spectrometry to identify either the cleaved amino acids or the deletion fragments. As used herein, the phrase "agent that cleaves amino acids from a terminus of a polypeptide" refers to a means, which can be physical, chemical or biological, for removing a carboxyl terminal or an amino terminal amino acid from a polypeptide. A physical agent is exemplified by a light source, for example, a laser, that can cleave a terminal amino acid, particularly where the amino acid is bound to the polypeptide through a photolabile bond. A chemical agent is exemplified by phenylisothiocyanate (Edman's reagent), which, in the presence of an acid, cleaves an amino terminal amino acid from a polypeptide. A biological agent the cleaves an amino acid from a terminus of a polypeptide is exemplified by enzymes such as aminopeptidases and carboxypeptidases, which are well known in the art (see, for example, U.S. Pat. No. 5,792,664; International Publ. No. WO 96/36732).

As used herein, the term "deletion fragment" refers to that portion of a polypeptide that remains following cleavage of one or more amino acids. The phrase "nested set of deletion fragments," when used in reference to a polypeptide to be sequenced, means a population of deletion fragments that results from sequential terminal cleavage of the amino acids of the polypeptide and that contains at least one deletion fragment that terminates in each amino acid of the portion of the polypeptide to be sequenced.

A process as disclosed herein can be used to identify a subject that has or is predisposed to a disease or condition. As used herein, the term "disease" has its commonly understood meaning of a pathologic state in a subject. For purposes of the present disclosure, a disease can be due, for example, to a genetic mutation, a chromosomal defect or an infectious organism. The term "condition," which is to be distinguished from conditioning of a polypeptide, is used herein to mean any state of a subject, including, for example, a pathologic state or a state that determines, in part, how the subject will respond to a stimulus. The condition of a subject is determined, in part, by the subject's genotype, which can provide an indication as to how the subject will respond, for example, to a graft or to treatment with a particular medicament. Accordingly, reference to a subject being predisposed to a condition can indicate, for example, that the subject has a genotype indicating that the subject will not respond favorably to a particular medicament.

Reference herein to an allele or an allelic variant being "associated" with a disease or condition means that the particular genotype is characteristic, at least in part, of the genotype exhibited by a population of subjects that have or are predisposed to the disease or condition. For example, an allelic variant such as a mutation in the BRCA1 gene is associated with breast cancer, and an allelic variant such as a higher than normal number of trinucleotide repeats in a particular gene is associated with prostate cancer. The skilled artisan will recognize that an association of an allelic variant with a disease or condition can be identified using well known statistical methods for sampling and analysis of a population.

As used herein, the term "conjugated" refers to a stable attachment, which can be a covalent attachment or a noncovalent attachment, provided the noncovalent attachment is stable under the condition to which the bond is to be exposed. In particular, a polypeptide can be conjugated to a solid support through a linker, which can provide a noncleavable, cleavable or reversible attachment.

As used herein, the term "solid support" means a flat surface or a surface with structures, to which a functional group, including a polypeptide containing a reactive group, can be conjugated. The term "surface with structures" is used herein to mean a support that contains, for example, wells, pins or the like, to which a functional group, including a polypeptide containing a reactive group, can be attached. Numerous examples of solid supports are disclosed herein or otherwise known in the art.

As used herein, the term "starting nucleic acid" refers to at least one molecule of a target nucleic acid, which encodes a target polypeptide. The starting nucleic acid can be DNA or RNA, including mRNA, and can be single stranded or double stranded, including a DNA-RNA hybrid. A mixture of any of these nucleic acids also can be employed as a starting nucleic acid for performing a process as disclosed herein, as can the nucleic acids produced following an amplification reaction.

It should be understood that the term "primer," as used herein, can refer to more than one primer, particularly in the case where there is some ambiguity in the information regarding the terminal sequence of a nucleic acid to be amplified. For example, where a nucleic acid sequence is inferred from protein sequence information, a collection of primers containing sequences representing all possible codon variations based on degeneracy of the genetic code is used for each strand. One primer from this collection is expected to be identical with a region of the sequence to be amplified.

A process is provided for determining the identity of a target polypeptide by using mass spectroscopy to determine the molecular mass of the target polypeptide and comparing it to the molecular mass of a polypeptide of known identity, thereby determining the identity of the target polypeptide. The identity of a target polypeptide can be, for example, the mass or amino acid sequence of at least a portion of the target polypeptide or by comparing the mass to a known polypeptide, which is a wild-type or known mutein.

A target polypeptide can be obtained from a subject, particularly from a cell or tissue in the subject or from a biological fluid. A target polypeptide also can be obtained by in vitro translation of an RNA molecule encoding the target polypeptide; or by in vitro transcription of a nucleic acid encoding the target polypeptide, followed by translation, which can be performed in vitro or in a cell, where the nucleic acid to be transcribed is obtained from a subject. Kits for performing the processes are also provided.

A process as disclosed herein provides a fast and reliable means for indirectly obtaining nucleic acid sequence information. Since the mass of a polypeptide is only about 10% of the mass of the corresponding DNA, the translated polypeptide generally is far more amenable to mass spectrometric detection than the corresponding nucleic acid. In addition, mass spectrometric detection of polypeptides yields analytical signals of far higher sensitivity and resolution than signals routinely obtained with DNA, due to the inherent instability of DNA to volatilization and its affinity for nonvolatile cationic impurities.

These processes and kits are particularly useful for a number of applications, such as identifying mutations and thereby screening for certain genetic disorders. A process as disclosed herein also provides an efficient means for determining the presence of a single base in a polynucleotide, for example, a single base mutation that introduces a STOP codon into an open reading frame of a gene, since such a mutation results in premature protein truncation; or a single base difference that results in a change in the encoded amino acid in an allelic variant of a polymorphic gene, since different amino acids can be distinguished based on their masses. Mutation screening by direct mass analysis of a gene such as p53 or BRCA1 requires a system that permits detection of a single base mutation, which can be difficult when examining a DNA sequence directly. A single base mutation resulting, for example, in a premature STOP codon, can radically change the mass of the encoded protein by truncation and, therefore, is readily identifiable using a process as disclosed herein. A single base change need not result in a STOP codon in order to be detectable, since a single base change that results in an amino acid change, for example, alanine to glycine, also is detectable using a process as disclosed herein (see Examples).

A process as disclosed herein can be used for identifying the presence of nucleotide repeats, particularly an abnormal number of nucleotide repeats, by determining the identity of a target polypeptide encoded by such repeats. As disclosed herein, an abnormal number of nucleotide repeats can be identified by using mass spectrometry to compare the mass of a target polypeptide with that of a corresponding known polypeptide.

In a particular application, the disclosed processes, and the kits useful for performing such processes, can be used, for example, in detecting an abnormal number of CAG repeats in the SCA-1 gene or in detecting the presence of a nucleotide substitution from a C to a G in one of the trinucleotide repeats in a subject with spino-cerebellar ataxia 1 (SCA-1). Mass spectrometry is used to determine the molecular mass of a target polypeptide encoded by a nucleic acid containing the trinucleotide repeats and comparing the molecular mass of the target polypeptide with the molecular mass of a polypeptide encoded by a nucleic acid having a known number of trinucleotide repeats and a known nucleotide sequence (see Example 1). The identification of the nucleotide sequence of the target nucleic acid by this method is made possible, in part, due to the increased mass accuracy obtained by using mass spectrometry to detect the translation product, rather than directly detecting the nucleic acid by mass spectrometry.

For illustrative purposes, the open reading frame of the gene containing the $(CAG)_X$ repeat associated with SCA-1 is shown in FIG. 1. The SCA-1 sequence contains, in addition to a nonvariable stretch of 12 CAG repeats, a variable stretch that is shown in FIG. 1A as containing 10 CAG repeats. As shown in FIG. 1A, the SCA-1 gene encodes a 7.5 kiloDalton (kDa) protein containing 10 consecutive glutamine (Q) residues (FIG. 1B). Accurate direct mass analysis of the 60 kDa 200-mer shown in FIG. 1A with currently available mass spectrometric instrumentation would be challenging. A recent study of the SCA-1 gene showed that 25 to 36 repeat units generally are present in unaffected subjects, while affected subjects have 43 to 81 repeat units. Assuming a worst case of 81 repeat units, 213 bases in addition to the 200-mer shown in FIG. 1A would have to be detected with sufficient resolution. A nucleotide sequence of greater than about a 400-mer (>120 kDa) has not been detected satisfactorily by mass spectrometry. In comparison, analysis of the translation product for the sequence having 81 repeats requires mass measurement of only about 137 amino acid residues (about 15 kDa). A typical 0.3% mass accuracy for low resolution instrumentation results in a maximum 13 Dalton error, which is far lower than the mass of a single amino acid residue. Accordingly, far better than single amino acid resolution can be obtained with a process for determining the identity of a target polypeptide as disclosed herein.

Obtaining a Target Polypeptide

Any polypeptide for which identifying information is required is contemplated herein as a target polypeptide. The polypeptide may be obtained from any source. A target polypeptide, or a target nucleic acid encoding the polypeptide, is can be obtained from a subject, which is typically a mammal, particularly a human. Generally, the target polypeptide is isolated prior to mass spectrometry so as to permit the determination of the molecular mass of the polypeptide by mass spectrometric analysis. The degree of to which a polypeptide must be isolated for mass spectrometry is known in the art and varies depending on the type of mass spectrometric analysis performed.

A target polypeptide can be a portion of a protein, and can be obtained using methods known in the art. For example, a protein can be isolated from a biological sample using an antibody, then can be cleaved using a proteinase that cuts selectively at specific amino acid sequences, and the target polypeptide can be purified by a method such as chromatography or electrophoresis. Thus, a process as disclosed herein can be performed, for example, by subjecting a protein, which contains a target polypeptide, to limited proteolysis; isolating the target polypeptide; and examining it by mass spectrometric analysis, thereby providing a means for determining the identity of the target polypeptide.

An antibody, or antigen binding fragment of an antibody, that interacts specifically with an epitope present on a polypeptide of interest is characterized by having specific binding activity for the epitope of at least about $1 \times 10^6$ M$^{-1}$, generally, at least about $1 \times 10^7$ M$^{-1}$ or greater. Accordingly, Fab, F(ab')$_2$, Fd and Fv fragments of an antibody that retain specific binding activity for a particular epitope are included within the meaning of the term antibody.

An antibody useful for isolating a polypeptide of interest, particularly a target polypeptide, can be a naturally occurring antibody or a non-naturally occurring antibody, including, for example, a single chain antibody, a chimeric antibody, a bifunctional antibody or a humanized antibody, as well as an antigen-binding fragment of such antibodies. Such non-naturally occurring antibodies can be constructed using solid phase peptide synthesis, can be produced recombinantly or can be obtained, for example, by screening combinatorial libraries containing of variable heavy chains and variable light chains (see Huse et al., *Science* 246:1275–1281 (1989)). These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Hilyard et al., *Protein Engineering: A practical approach* (IRL Press 1992); Borrabeck, *Antibody Engineering*, 2d ed. (Oxford University Press 1995); Harlow and Lane, "Antibodies: A laboratory manual" (Cold Spring Harbor Laboratory Press 1988)).

An antibody useful for isolating a target polypeptide can be obtained from a commercial source, or can be raised using a protein containing the target polypeptide, or a peptide portion thereof, as an immunogen, or using an epitope that is fused to the polypeptide, for example, a myc epitope. Such an immunogen can be prepared from natural sources or produced recombinantly, or can be synthesized using routine chemical methods. An otherwise non-immunogenic epitope can be made immunogenic by coupling the hapten to a carrier molecule such bovine serum albumin (BSA) or keyhole limpet hemocyanin (KLH), or by expressing the epitope as a fusion protein. Various other carrier molecules and methods for coupling a hapten to a carrier molecule are well known in the art (see, for example, Harlow and Lane, "Antibodies: A laboratory manual" (Cold Spring Harbor Laboratory Press 1988)).

An antibody that interacts specifically with a polypeptide of interest, particularly a target polypeptide or peptide portion thereof, is useful, for example, for determining whether the target polypeptide is present in a biological sample. The identification of the presence or level of the target polypeptide can be made using well known immunoassay and immunohistochemical methods (Harlow and Lane, "Antibodies: A laboratory manual" (Cold Spring Harbor Laboratory Press 1988)). In particular, an antibody that interacts specifically with a tag peptide fused to a target polypeptide can be used to isolate the target polypeptide from a sample, which can be, for example, a biological sample or an in vitro translation reaction.

Methods for raising polyclonal antibodies, for example, in a rabbit, goat, mouse or other mammal, are well known in the art (Harlow and Lane, "Antibodies: A laboratory manual" (Cold Spring Harbor Laboratory Press 1988)). In addition, monoclonal antibodies can be obtained using methods that are well known and routine in the art (Harlow and Lane, "Antibodies: A laboratory manual" (Cold Spring Harbor Laboratory Press 1988)). Essentially, spleen cells from a mouse immunized with a polypeptide of interest, or a peptide portion thereof, can be fused to an appropriate myeloma cell line such as SP/02 myeloma cells to produce hybridoma cells. Cloned hybridoma cell lines can be screened using the immunizing polypeptide to identify clones that secrete appropriately specific antibodies. Hybridomas expressing antibodies having a desirable specificity and affinity can be isolated and utilized as a continuous source of the antibodies, which are useful, for example, for inclusion in a kit as provided herein. Similarly, a recombinant phage that expresses, for example, a single chain antibody of interest also provides a monoclonal antibody that can used for preparing standardized kits.

Isolation and identification of a target polypeptide can be facilitated by linking a tag to the polypeptide, for example, by fusing the polypeptide to a tag peptide. Such a fusion polypeptide can be obtained, for example, by in vitro transcription and translation of a nucleotide sequence encoding the target polypeptide linked in frame to a nucleotide sequence encoding the tag peptide, then isolating the fusion polypeptide from the translation reaction using a reagent that interacts specifically with the tag peptide. The tag peptide can be, for example, a myc epitope or a peptide portion of the *Haemophilus influenza* hemagglutinin protein, against which specific antibodies can be prepared and also are commercially available. A tag peptide also can be a polyhistidine sequence, for example, a hexahistidine sequence (His-6), which interacts specifically with metal ions such as zinc, nickel, or cobalt ions, or a polylysine or polyarginine sequence, comprising at least about four lysine or four arginine residues, respectively, which interact specifically with zinc, copper or, for example a zinc finger protein.

A tag can be also can be added to the polypeptide either by chemical modification of the polypeptide during or following its synthesis. For example, a target polypeptide containing a tag can be obtained by isolation from an in vitro translation reaction of a target nucleic acid molecule, where the translation reaction is performed in the presence of a modified amino acid and, if appropriate, a mis-aminoacylated tRNA carrying the modified amino acid. The modification of the amino acid is selected so that it contains a tag that allows the isolation of a polypeptide containing the modified amino acid. For example, a lysine residue can be replaced with a biotinylated lysine analog (or other lysine analog containing a tag) in the translation reaction, resulting in a translated polypeptide that contains biotinylated lysine residues. Such a tagged polypeptide can be isolated by affinity chromatography on a bed of immobilized avidin or streptavidin, for example. Other modified amino acids are disclosed in the U.S. Pat. No. 5,643,722.

A target polypeptide can be isolated by affinity purification using, for example, an antibody, avidin or other specific reagent linked to a solid support. In such a method, the translation reaction is poured over the support, which can be present, for example, in a column, and the polypeptide is bound due to its specifically interacting with the reagent. For example, a target polypeptide fused to a polyhistidine tag peptide can be isolated on a column or bed of chelated nickel ions, whereas a target polypeptide fused to a polylysine or polyarginine tag can be isolated on a column or bed of chelated zinc or copper ions. Beds or columns having such divalent metal ions chelated thereto can be obtained from a commercial source or prepared using methods known in the art. The polypeptide then can be eluted from the column in an isolated form and subjected to mass spectrometry.

Isolation of a Nucleic Acid Encoding a Target Polypeptide

In other embodiments, the polypeptide may be prepared from nucleic acid that encodes it. Thus, the target polypeptide can be isolated from a cell or tissue of the subject; or can be synthesized in vitro from an RNA molecule, for example, by in vitro translation, or from a DNA molecule by in vitro transcription and translation; or can be synthesized in a eukaryotic or prokaryotic host cell that is transformed with a target nucleic acid, which encodes the target polypeptide.

In preferred embodiments herein, a target polypeptide is isolated from a cell, a tissue or an in vitro translation system, for example, a reticulocyte lysate system. In vitro translation or in vitro transcription followed by translation are among the preferred methods of preparation of the polypeptides. The polypeptides can be purified after translation using any method known to those of skill in the art for purification. For example, the polypeptide can be isolated using a reagent that interacts specifically with the target polypeptide or with a protein containing the target polypeptide. Such a reagent can be an antibody that interacts specifically with an epitope of the target polypeptide, for example, an antibody to an epitope encoded by a trinucleotide repeat sequence. If the target polypeptide contains an amino acid that can be any of several amino acids, for example, where the target polypeptide is from a mutated protein, the antibody preferably interacts with an epitope that does not include an epitope containing the mutated amino acid(s). Antibodies that interact specifically with a protein containing a target polypeptide, or with the target polypeptide, can be prepared using methods well known in the art (Harlow and Lane, "Antibodies: A laboratory manual" (Cold Spring Harbor Laboratory Press 1988)).

A target polypeptide can be obtained from an RNA molecule, for example, by in vitro translation of the RNA molecule. The target polypeptide also can be obtained from a DNA molecule, where in vitro transcription of at least a portion of the DNA molecule is performed prior to translation. In particular, at least a portion of the DNA molecule containing the nucleotide sequence encoding the target polypeptide can be amplified, for example, by PCR prior to performing in vitro transcription or translation. Accordingly, a process for determining the identity of a target polypeptide, as disclosed herein, can include a step of isolating a target nucleic acid molecule, which can be DNA or RNA and from which the target polypeptide is obtained.

A nucleic acid sample, in an isolated or unisolated form, can be utilized as a starting nucleic acid in a method as disclosed herein, provided the sample is suspected of containing the target nucleic acid. The target nucleic acid can be a portion of a larger molecule or can be present initially as a discrete molecule such that the specific sequence constitutes the entire nucleic acid.

It is not necessary that a starting nucleic acid contain only the target nucleic acid in an isolated form. Provided that the starting nucleic acid is in an isolated form, the target nucleic acid can be a minor fraction of a complex mixture, for example, a portion of the, β-globin gene contained in whole human DNA, or a portion of nucleic acid sequence of a particular microorganism that constitutes only a minor fraction of a particular biological sample. A starting nucleic acid also can contain more than one population of target nucleic acids.

The starting nucleic acid can be obtained from any source, including a natural source such as bacteria, yeast, viruses, protists, and higher organisms, including plants or animals, particularly from tissues, cells or organelles of such sources, or can be obtained from a plasmid such as pBR322, in which the nucleic acid previously was cloned. The starting nucleic acid can represent a sample of DNA, for example, isolated from an animal, particularly a mammal such as a human subject, and can be obtained from any cell source or body fluid. Examples of cell sources available in clinical practice include, but are not limited to, blood cells, buccal cells, cervico-vaginal cells, epithelial cells from urine, or cells present in a tissue obtained, for example, by biopsy. Body fluids include blood, urine and cerebrospinal fluid, as well as tissue exudates from a site of infection or inflammation.

A nucleic acid molecule can be extracted from a cell source or body fluid using any of numerous methods well known and routine in the art, and the particular method used to extract the nucleic acid will be selected as appropriate for the particular biological sample, including whether the nucleic acid to be isolated is DNA or RNA (see, for example, Sambrook et al., *Molecular Cloning: A laboratory manual* (Cold Spring Harbor Laboratory Press 1989). For example, freeze-thaw and alkaline lysis procedures can be useful for obtaining nucleic acid molecules from solid materials such as cell or tissue samples; heat and alkaline lysis procedures can be useful for obtaining nucleic acid molecules from urine; and proteinase K extraction or phenol extraction can be useful to obtain nucleic acid from cells or tissues such as a blood sample (Rolff et al., "PCR: Clinical diagnostics and research" (Springer Verlag Publ. 1994)).

For utilization of a target nucleic acid from cells, the cells can be suspended in a hypotonic buffer and heated to about 90° C. to 100° C. for about 1 to 15 minutes, until cell lysis and dispersion of intracellular components occur. After the heating step, amplification reagents, if desired, can be added directly to the lysate. Such a direct amplification method can be used, for example, on peripheral blood lymphocytes or amniocytes. The amount of DNA extracted for analysis of human genomic DNA generally is at least about 5 pg, which corresponds to about 1 cell equivalent of a genome size of $4 \times 10^9$ base pairs. In some applications, for example, detection of sequence alterations in the genome of a microorganism, variable amounts of DNA can be extracted.

In general, the nucleotides forming a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. A polynucleotide also includes nucleotide analogs, including non-naturally occurring synthetic nucleotides or modified naturally occurring nucleotides. Such nucleotide analogs are well known in the art and are commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997)). The covalent bond linking the nucleotides of a polynucleotide generally is a phosphodiester bond. The covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977–986 (1994); Ecker and Crooke, *BioTechnology* 13:351360 (1995)).

Where it is desired to synthesize a polynucleotide for use in a process as disclosed herein or for inclusion in a kit, the artisan will know that the selection of particular nucleotides or nucleotide analogs and the covalent bond used to link the nucleotides will depend, in part, on the purpose for which the polynucleotide is prepared. For example, where a polynucleotide will be exposed to an environment containing substantial nuclease activity, the artisan will select nucleotide analogs or covalent bonds that are relatively resistant to the nucleases. A polynucleotide containing naturally occurring nucleotides and phosphodiester bonds can be chemically synthesized or can be produced using recombinant DNA methods, using an appropriate polynucleotide as a template. In comparison, a polynucleotide containing nucleotide analogs or covalent bonds other than phosphodiester bonds generally will be chemically synthesized, although an enzyme such as T7 polymerase can incorporate certain types of nucleotide analogs and, therefore, can be used to produce such a polynucleotide recombinantly from an appropriate template (Jellinek et al., *Biochemistry* 34:11363–11372 (1995)).

A polynucleotide, for example, an oligonucleotide, that specifically hybridizes to a nucleic acid, particularly to a target nucleic acid or to sequences flanking a target nucleic acid is particularly useful. Such a hybridizing polynucleotide is characterized, in part, in that it is at least nine nucleotides in length, such sequences being particularly useful as primers for the polymerase chain reaction (PCR) and can be at least fourteen nucleotides in length or, if desired, at least seventeen nucleotides in length, such nucleotide sequences being particularly useful as hybridization probes, as well as for PCR. It should be recognized that the conditions required for specific hybridization of a first polynucleotide, for example, a PCR primer, with a second polynucleotide, for example, a target nucleic acid, depends, in part, on the degree of complementarity shared between the sequences, the GC content of the hybridizing molecules, and the length of the antisense nucleic acid sequence, and that conditions suitable for obtaining specific hybridization can be calculated based on readily available formulas or can be determined empirically (Sambrook et al., *Molecular Cloning: A laboratory manual* (Cold Spring Harbor Laboratory Press 1989; Ausubel et al., *Current Protocols in Molecular Biology* (Green Publ., NY 1989)).

Transcription and Translation of a Target Nucleic Acid

A target polypeptide can be obtained by translating an RNA molecule encoding the target polypeptide in vitro. If desired, the RNA molecule can be obtained by in vitro transcription of a nucleic acid, generally DNA, encoding the target polypeptide. Translation of a target polypeptide can be effected by directly introducing an RNA molecule encoding the polypeptide into an in vitro translation reaction or by introducing a DNA molecule encoding the polypeptide into an in vitro transcription/translation reaction or into an in vitro transcription reaction, then transferring the RNA to an in vitro translation reaction.

For in vitro transcription, the target DNA is operably linked to a promoter, from which transcription is initiated in the presence of an RNA polymerase capable of interacting with the promoter, ribonucleotides, and other reagents necessary for in vitro transcription. In vitro transcription can be performed as a separate step from an in vitro translation reaction or can be carried out in a single reaction, using well known methods (see, for example, Sambrook et al., *Molecular Cloning: A laboratory manual* (Cold Spring Harbor Laboratory Press 1989; see, also, U.S. Pat. No. 4,766,072, which describes vectors useful for in vitro transcription). In vitro transcription kits are well known and are commercially available (Promega Corp.; Madison Wis.).

An in vitro transcription reaction is carried out by incubating a template DNA, which generally includes the target nucleic acid, for about 1 hour at 37° C. or 40° C., depending on the polymerase, in the presence of ribonucleotides, a cap analog such as GpppG or a methylated derivative thereof, an RNAase inhibitor, an RNA polymerase that recognizes the promoter operably linked upstream of the DNA to be transcribed, and an appropriate buffer containing Tris-HCl, $MgCl_2$, spermidine and NaCl. Following the transcription reaction, RNAase-free DNAse can be added to remove the DNA template and the RNA purified, for example, by phenol-chloroform extraction (see, Sambrook et al., *Molecular Cloning: A laboratory manual* (Cold Spring Harbor Laboratory Press 1989). Usually about 5 to 10 µg of RNA is obtained per microgram of template DNA.

Where RNA is produced in a prokaryotic in vitro transcription system, the RNA can be produced in an uncapped form, such as by in vitro transcription in the absence of a cap analog, since translation of RNA in a prokaryotic system does not require the presence of a cap such as $N_7$-methyl-G covalently linked to the 5' end of the mRNA. Capped RNA is translated much more efficiently than uncapped RNA in eukaryotic systems and, therefore, it can be desirable to cap the RNA during transcription or during translation when using a eukaryotic translation system. The in vitro transcribed RNA can be isolated, for example, by ethanol precipitation, then used for in vitro translation.

Translation systems can be cellular or cell-free and can be prokaryotic or eukaryotic. Cellular translation systems generally utilize intact cells, for example, oocytes, or utilize permeabilized cells, whereas cell-free (in vitro) translation systems utilize cell or tissue lysates or extracts, purified or partially purified components, or combinations thereof.

In vitro translation systems are well known and are commercially available and many different types and systems are well known and routinely used. Examples of in vitro translation systems include eukaryotic cell lysates such as rabbit reticulocyte lysates, rabbit oocyte lysates, human cell lysates, insect cell lysates and wheat germ extracts. Such lysates and extracts are can be prepared or are commercially available (Promega Corp.; Stratagene, La Jolla Calif.; Amersham, Arlington Heights Ill.; and GIBCO/BRL, Grand Island N.Y.). In vitro translation systems generally contain macromolecules such as enzymes; translation, initiation and elongation factors; chemical reagents; and ribosomes. Mixtures of purified translation factors, as well as combinations of lysates or lysates supplemented with purified translation factors such as initiation factor-1 (IF-1), IF-2, IF-3 (alpha or beta), elongation factor T (EF-Tu) or termination factors, also can be used for mRNA translation in vitro.

Incubation times for in vitro translation range from about 5 minutes to many hours, but generally are about thirty minutes to five hours, usually about one to three hours. Incubation can be performed in a continuous manner, whereby reagents are flowed into the system and nascent polypeptides removed or left to accumulate, using a continuous flow system as described by Spirin et al. (*Science* 242:1162–64 (1988)). Such a process can be desirable for large scale production of nascent polypeptides. Incubation times vary significantly with the volume of the translation mix and the temperature of the incubation. Incubation temperatures can be between about 4° C. to 60° C., generally about 15° C. to 50° C., and usually about 25° C. to 45° C., particularly about 25° C. or about 37° C.

Translation reactions generally contain a buffer such as Tris-HCl, HEPES, or other suitable buffering agent to maintain the solution at about pH 6 to pH 8, generally about pH 7. Other components of a translation system can include dithiothreitol (DTT) or 2-mercaptoethanol as reducing agents, RNasin to inhibit RNA breakdown, and nucleoside triphosphates or creatine phosphate and creatine kinase to provide chemical energy for the translation process.

An in vitro translation system can be a reticulocyte lysate, which is available commercially or can be prepared according to methods disclosed herein or otherwise known in the art. Commercially available reticulocyte lysates are available, for example, from New England Nuclear and Promega Corp. (Cat. #L4960, L4970, and L4980). An in vitro translation system also can be a wheat germ translation system, which is available commercially or can be prepared according to well known methods. Commercially available wheat germ extracts can be obtained, for example, from Promega Corp. (for example, Cat # L4370). An in vitro translation system also can be a mixture of a reticulocyte lysate and a wheat germ extract, as can be obtained commercially (for example, Promega Corp., catalog # L4340). Other useful in vitro translation systems include *E. coli* extracts, insect cell extracts and frog oocyte extracts.

A rabbit reticulocyte lysate can be prepared as follows. Rabbits are rendered anemic by inoculation with acetylphenylhydrazine. About 7 days later, the rabbits are bled and the blood is collected and mixed with an ice cold salt solution containing NaCl, magnesium acetate (MgAc), KCl, and heparin. The blood mixture is filtered through a cheesecloth, centrifuged, and the buffy coat of white cells is removed. The pellet, which contains erythrocytes and reticulocytes, is washed with the salt solution, then lysed by the addition of in equal volume of cold water. Endogenous RNA is degraded by treating the lysate with micrococcal nuclease and calcium ions, which are necessary for nuclease activity, and the reaction is stopped by the addition of EGTA, which chelates the calcium ions and inactivates the nuclease. Hemin (about 20 to 80 $\mu$M), which is a powerful suppressor of an inhibitor of the initiation factor elF-2, also can be added to the lysate. Translation activity of the lysates can be optimized by the addition of an energy generating system, for example, phosphocreatine kinase and phosphocreatine. The lysates then can be aliquoted and stored at −70° C. or in liquid nitrogen. Further details regarding such a protocol are known (see, e.g., Sambrook et al., *Molecular Cloning: A laboratory manual* (Cold Spring Harbor Laboratory Press 1989).

An in vitro translation reaction using a reticulocyte lysate can be carried out as follows. Ten $\mu$l of a reticulocyte lysate, which can be prepared as disclosed above or can be obtained commercially, is mixed with spermidine, creatine phosphate, amino acids, HEPES buffer (pH 7.4), KCl, MgAc and the RNA to be translated, and incubated for an appropriate time, generally about one hour at 30° C. The optimum amount of MgAc for obtaining efficient translation varies from one reticulocyte lysate preparation to another and can be determined using a standard preparation of RNA and a concentration of MgAc varying from 0 to 1 mM. The optimal concentration of KCl also can vary depending on the specific reaction. For example, 70 mM KCl generally is optimal for translation of capped RNA, whereas 40 mM generally is optimal for translation of uncapped RNA. Optionally, the translation process is monitored by a method such as mass spectrometric analysis. Monitoring also can be performed, for example, by adding one or more radioactive amino acids such as $^{35}$S-methionine and measuring incorporation of the radiolabel into the translation products by precipitating the proteins in the lysate such as with TCA and counting the amount of radioactivity present in the precipitate at various times during incubation. The translation products also can be analyzed by immunoprecipitation or by SDS-polyacrylamide gel electrophoresis (see, for example, Sambrook et al., *Molecular Cloning: A laboratory manual* (Cold Spring Harbor Laboratory Press 1989; Harlow and Lane, "Antibodies: A laboratory manual" (Cold Spring Harbor Laboratory Press 1988)).

A wheat germ extract can be prepared as described by Roberts and Paterson (*Proc. Natl. Acad. Sci., USA* 70:2330–2334 (1973)) and can be modified as described by Anderson (*Meth. Enzymol.* 101:635 (1983)), if desired. The protocol also can be modified according to manufacturing protocol L418 (Promega Corp.). Generally, wheat germ extract is prepared by grinding wheat germ in an extraction buffer, followed by centrifugation to remove cell debris. The supernatant is separated by chromatography from endogenous amino acids and from plant pigments that are inhibitory to translation. The extract also is treated with micrococcal nuclease to destroy endogenous mRNA, thereby reducing background translation to a minimum. The wheat germ extract contains the cellular components necessary for protein synthesis, including tRNA, rRNA and initiation, elongation and termination factors. The extract can be optimized further by the adding an energy generating system such as phosphocreatine kinase and phosphocreatine; MgAc is added at a level recommended for the translation of most mRNA species, generally about 6.0 to 7.5 mM magnesium.

In vitro translation in wheat germ extracts can be performed as described, for example, Erickson and Blobel (*Meth. Enzymol.* 96:38 (1982)), and can be modified, for example, by adjusting the final ion concentrations to 2.6 mM magnesium and 140 mM potassium, and the pH to 7.5 (U.S. Pat. No. 4,983,521). Reaction mixtures can be incubated at 24° C. for 60 minutes. Translations in wheat germ extracts can also be performed as described in U.S. Pat. No. 5,492, 817.

In vitro translation reactions can be optimized by the addition of ions or other reagents. For example, magnesium is important for optimal translation, as it enhances the stability of assembled ribosomes and functions in their binding together during translation. Magnesium also appears to facilitate polymerase binding. Potassium also is important for optimizing translation but, unlike magnesium, for coupled transcription and translation reactions, the potassium ion concentration need not be altered beyond standard translation preparation levels.

Potassium and magnesium are in the standard rabbit reticulocyte lysate and their levels are partially from the endogenous lysate level and partially from the additions made in the preparation of the lysate, as are done for translation lysates. Since the magnesium concentration should be adjusted within a rather narrow range for optimal translation, the lysate magnesium levels should be measured directly through the use of a magnesium assay, prior to the addition of extra magnesium, so that the amount of magnesium in a reaction can be standardized from one batch of lysate to the next. The Lancer "Magnesium Rapid Stat Diagnostic Kit" (Oxford Lab Ware Division, Sherwood Medical Co.; St. Louis Mo.) is a useful assay for accurately measuring the magnesium level in a biological fluid. Once the magnesium on concentration for a given batch of lysate is determined, additional magnesium, for example, in the form of a concentrated magnesium salt solution, can be added in a known manner to bring the magnesium concentration of the lysate to within the optimal range or, in the case of a modified lysate preparation to be used as one-half of a reaction mixture, to within twice the optimal range. The final magnesium concentration of rabbit reticulocyte lysate is adjusted, for example, by adding a concentrated solution of $MgCl_2$ or MgAc to a concentration greater than 2.5 mM, but less than 3.5 mM, generally between 2.6 mM and 3.0 mM.

A common addition to an in vitro translation reaction is an amount of a polyamine sufficient to stimulate efficient chain elongation. Accordingly, spermidine can be added to a reticulocyte lysate translation reaction to a final concentration of about 0.2 mM. Spermidine also can be added to wheat germ extracts, generally at a concentration of about 0.9 mM. Since the presence of polyamines lowers the effective magnesium concentration in a reaction, the presence of spermidine in a translation reaction should be considered when determining the appropriate concentration of magnesium to use. DTT also is added to the translation mixture, generally at a final concentration of about 1.45 mM in reticulocyte lysates and about 5.1 mM in wheat germ extracts.

Translation systems can be supplemented with additional factors such as tRNA molecules, which are commercially available (Sigma Chemical, St. Louis, Mo.; Promega Corp., Madison Wis.; Boehringer Mannheim Biochemicals, Indianapolis Ind.) or can be prepared from E. coli, yeast, calf liver or wheat germ using well known methods. Isolation and purification of tRNA molecules involve cell lysis and phenol extraction, followed by chromatography on DEAE-cellulose. Amino acid-specific tRNA, for example, tRNA<fMet>, can be isolated by expression from cloned genes and overexpressed in host cells and separated from total tRNA in high yield and purity using, for example, preparative polyacrylamide gel electrophoresis, followed by band excision and elution (Seong and RajBhandary, Proc. Natl. Acad. Sci., USA 84:334–338, 1987)).

Translation efficiency can be improved by adding RNAase inhibitors such as RNASIN or heparin to the translation reaction. RNASIN can be obtained, for example, from Promega Corp. (Cat # N2514). About 40 units of RNASIN are added to a 50 $\mu$l reaction. Although the addition of an RNAase inhibitor to reticulocyte lysates is not crucial, only limited translation occurs if an RNAase inhibitor is not added to a wheat germ extract translation reaction.

The translation process, including the movement of the ribosomes on the RNA molecules, is inhibited at an appropriate time by the addition of an inhibitor of translation, for example, cycloheximide at a final concentration of 1 $\mu$g/ml. Magnesium ion, for example, $MgCl_2$, at a concentration of about 5 mM also can be added to maintain the mRNA-80S ribosome-nascent polypeptide complexes (polysomes).

For determining the optimal in vitro translation conditions, translation of mRNA in an in vitro system can be monitored, for example, by mass spectrometric analysis. Alternatively, a labeled amino acid such as $^{35}$S-methionine can be included in the translation reaction together with an amino acid mixture lacking this specific amino acid (e.g., methionine). A labeled non-radioactive amino acid also can be incorporated into a nascent polypeptide. For example, the translation reaction can contain a mis-aminoacylated tRNA (U.S. Pat. No. 5,643,722). For example, a non-radioactive marker can be mis-aminoacylated to a tRNA molecule and the tRNA amino acid complex is added to the translation system. The system is incubated to incorporate the non-radioactive marker into the nascent polypeptide and polypeptides containing the marker can be detected using a detection method appropriate for the marker. Mis-aminoacylation of a tRNA molecule also can be used to add a marker to the polypeptide in order to facilitate isolation of the polypeptide. Such markers include, for example, biotin, streptavidin and derivatives thereof (see U.S. Pat. No. 5,643, 722). The translation process can also be followed by mass spectrometric analysis, which does not require the use of radioactivity or other label.

In vitro transcription and translation reactions can be performed simultaneously using, for example, a commercially available system such as the Coupled Transcription/Translation System (Promega Corp, catalog # L4606, # 4610 or # 4950). Coupled transcription and translation systems using RNA polymerases and eukaryotic lysates are described in U.S. Pat. No. 5,324,637. Coupled in vitro transcription and translation also can be carried out using a prokaryotic system such as a bacterial system, for example, E. coli S30 cell-free extracts (Zubay, Ann. Rev. Genet. 7:267 (1973)). Although such prokaryotic systems allow coupled in vitro transcription and translation, they also can be used for in vitro translation only. When using a prokaryotic translation system, the RNA should contain sequence elements necessary for translation of an RNA in a prokaryotic system. For example, the RNA should contain prokaryotic ribosome binding sites, which can be incorporated into a target nucleic acid sequence during amplification using a primer containing the prokaryotic ribosome binding sequence. The ribosome binding sequence is positioned downstream of a promoter for use in in vitro transcription.

Cellular translation systems can be prepared as follows. Cells are permeabilized by incubation for a short period of time in a solution containing low concentrations of detergents in a hypotonic media. Useful detergents include Nonidet-P 40 (NP40), Triton X-100 (TX-100) or deoxycholate at concentrations of about 0.01 nM to 1.0 mM, generally between about 0.1 $\mu$M to about 0.01 mM, particularly about 1 $\mu$M. Such systems can be formed from intact cells in culture, including bacterial cells, primary cells, immortalized cell lines, human cells or mixed cell populations.

A target polypeptide can be obtained from a host cell transformed with and expressing a nucleic acid encoding the target polypeptide. The target nucleic acid can be amplified, for example, by PCR, inserted into an expression vector, and the expression vector introduced into a host cell suitable for expressing the polypeptide encoded by the target nucleic acid. Host cells can be eukaryotic cells, particularly mammalian cells such as human cells, or prokaryotic cells, including, for example, E. coli. Eukaryotic and prokaryotic expression vectors are well known in the art and can be obtained from commercial sources. Following expression in the host cell, the target polypeptide can be isolated using methods as disclosed herein. For example, if the target polypeptide is fused to a His-6 peptide, the target polypeptide can be purified by affinity chromatography on a chelated nickel ion column.

Amplification of the Target Nucleic Acid Sequence

At least a portion of a target nucleic acid can be amplified prior to obtaining the target polypeptide encoded by the nucleic acid. PCR, for example, can be performed prior to in vitro transcription and translation of a target nucleic acid. Amplification processes include the polymerase chain reaction (Newton and Graham, "PCR" (BIOS Publ. 1994)); nucleic acid sequence based amplification; transcription-based amplification system, self-sustained sequence replication; Q-beta replicase based amplification; ligation amplification reaction; ligase chain reaction (Wiedmann et al., *PCR Meth. Appl.* 3:57–64 (1994); Barany, *Proc. Natl. Acad. Sci., USA* 88, 189–93 (1991)); strand displacement amplification (Walker et al., *Nucl. Acids Res.* 22:2670–77 (1994)); and variations of these methods, including, for example, reverse transcription PCR (RT-PCR; Higuchi et al., *Bio/Technology* 11:1026–1030 (1993)), and allele-specific amplification.

Where a nucleotide sequence of the target nucleic acid is amplified by PCR, well known reaction conditions are used. The minimal components of an amplification reaction include a template DNA molecule; a forward primer and a reverse primer, each of which is capable of hybridizing to the template DNA molecule or a nucleotide sequence linked thereto; each of the four different nucleoside triphosphates or appropriate analogs thereof; an agent for polymerization such as DNA polymerase; and a buffer having the appropriate pH, ionic strength, cofactors, and the like. Generally, about 25 to 30 amplification cycles, each including a denaturation step, an annealing step and an extension step, are performed, but fewer cycles can be sufficient or more cycles can be required depending, for example, on the amount of the template DNA molecules present in the reaction. Examples of PCR reaction conditions are described in U.S. Pat. No. 5,604,099.

A nucleic acid sequence can be amplified using PCR as described in U.S. Pat. No. 5,545,539, which provides an improvement of the basic procedure for amplifying a target nucleotide sequence by including an effective amount of a glycine-based osmolyte in the amplification reaction mixture. The use of a glycine-based osmolyte improves amplification of sequences rich in G and C residues and, therefore, can be useful, for example, to amplify trinucleotide repeat sequences such as those associated with Fragile X syndrome (CGG repeats) and myotonic dystrophy (CTG repeats).

A primer can be prepared from a naturally occurring nucleic acid, for example, by purification from a restriction digest of the nucleic acid, or can be produced synthetically. A primer is capable of acting as a point of initiation of nucleic acid synthesis when placed under conditions sufficient for synthesis of a primer extension product. Particularly useful primers can hybridize specifically to the target sequence or to sequences adjacent to the target sequence. Any specific nucleic acid sequence can be amplified by PCR. It is only necessary that a sufficient number of bases at the ends of the target sequence or in the target sequence be known so as to allow preparation of two oligonucleotide primers that can hybridize to the termini of the sequence to be amplified and its complement, at relative positions along each sequence such that an extension product synthesized from one primer, when it is separated from its template (complement), can serve as a template for extension from the other primer into a nucleic acid of defined length. The greater the knowledge about the bases at both ends of the sequence, the greater can be the specificity of the primers for the target nucleic acid sequence and, therefore, the greater the efficiency of the amplification process. If desired, however, a primer specific for one end of the target nucleic acid can be used and a second primer, based on a known sequence linked to the opposite terminus of the target nucleic acid, can be used for amplification of the complementary strand.

A primer must be sufficiently long to prime the synthesis of extension products in the presence of the agent for polymerization. The exact length of a primer will depend on many factors, including the temperature at which hybridization and primer extension are to be performed; the composition of the primer; and the method used. Depending on the complexity of the target sequence, a primer generally contains about 9 to about 25 nucleotides, although it can contain more nucleotides. As compared to longer primers, shorter primers generally require lower temperatures to form sufficiently stable hybrid complexes with a template nucleic acid (see Sambrook et al., *Molecular Cloning: A laboratory manual* (Cold Spring Harbor Laboratory Press 1989).

Primers as disclosed herein are selected to be substantially complementary to the different strands of each specific sequence to be amplified. As such, the primers can hybridize specifically with their respective complementary strands under defined hybridization conditions. A primer sequence need not reflect the exact sequence of the template. For example, a non-complementary nucleotide fragment can be attached to the 5' end of the primer, with the remainder of the primer sequence being complementary to the template strand. Primers generally should have exact complementarity with a sequence from the target nucleic acid, or complement thereof, so that optimal amplification can be obtained.

A forward or the reverse primer can contain, if desired, a nucleotide sequence of a promoter, for example, a bacteriophage promoter such as an SP6, T3 or T7 promoter. Amplification of a target nucleic acid sequence using such a primer produces an amplified target nucleic acid operably linked to the promoter. Such a nucleic acid can be used in an in vitro transcription reaction to transcribe the amplified target nucleic acid sequence. Nucleotide sequences of the SP6, T3 and T7 promoter are set forth below:

```
SP6 promoter sequences:
5' d(CATACGATTTAGGTGACACTATAG)3'   SEQ ID NO: 1;

5' d(ATTTAGGTGACACTATAG)3'         SEQ ID NO: 2;

T3 promoter sequence:
5' d(ATTAACCCTCACTAAAGGGA)3'       SEQ ID NO: 3; and
```

```
-continued
T7 promoter sequence:
5' d(TAATACGACTCACTATAGGG)3'      SEQ ID NO: 4.
```

A primer, which can contain a promoter, also can contain an initiation (ATG) codon, or complement thereof, as appropriate, located downstream of the promoter, such that amplification of the target nucleic acid results in an amplified target sequence containing an ATG codon in frame with the desired reading frame. The reading frame can be the natural reading frame or can be any other reading frame. Where the target polypeptide does not exist naturally, operably linking an initiation codon to the nucleic acid encoding the target polypeptide allows translation of the target polypeptide in the desired reading frame.

A forward or reverse primer also can contain a nucleotide sequence, or the complement of a nucleotide sequence (if present in the reverse primer), encoding a second polypeptide. The second polypeptide can be a tag peptide, which interacts specifically with a particular reagent, for example, an antibody. A second polypeptide also can have an unblocked and reactive amino terminus or carboxyl terminus.

The fusion of a tag peptide to a target polypeptide or other polypeptide of interest allows the detection and isolation of the polypeptide. A target polypeptide encoded by a target nucleic acid fused to a sequence encoding a tag peptide can be isolated from an in vitro translation reaction mixture using a reagent that interacts specifically with the tag peptide, then the isolated target polypeptide can be subjected to mass spectrometry, as disclosed herein. It should be recognized that an isolated target polypeptide fused to a tag peptide or other second polypeptide is in a sufficiently purified form to allow mass spectrometric analysis, since the mass of the tag peptide will be known and can be considered in the determination.

Numerous tag peptides and the nucleic acid sequences encoding such tag peptides, generally contained in a plasmid, are known and are commercially available (e.g., NOVAGEN). Any peptide can be used as a tag, provided a reagent such as an antibody that interacts specifically with the tag peptide is available or can be prepared and identified. Frequently used tag peptides include a myc epitope, which includes a 10 amino acid sequence from c-myc (see Ellison et al., *J. Biol. Chem.* 266:21150–21157 (1991)); the pFLAG system (International Biotechnologies, Inc.); the pEZZ-protein A system (Pharmacia); a 16 amino acid peptide portion of the *Haemophilus influenza* hemagglutinin protein; a glutathione-S-transferase (GST) protein; and a His-6 peptide. Reagents that interact specifically with a tag peptide also are known, and some are commercially available and include antibodies and various other molecules, depending on the tag, for example, metal ions such as nickel or cobalt ions, which interact specifically with a polyhistidine peptide such as His-6; or glutathione, which can be conjugated to a solid support such as agarose and interacts specifically with GST.

A second polypeptide also can be designed to serve as a mass modifier of the target polypeptide encoded by the target nucleic acid. Accordingly, a target polypeptide can be mass modified by translating an RNA molecule encoding the target polypeptide operably linked to a mass modifying amino acid sequence, where the mass modifying sequence can be at the amino terminus or the carboxyl terminus of the fusion polypeptide. Modification of the mass of the polypeptide derived from the target nucleic acid is useful, for example, when several peptides are analyzed in a single mass spectrometric analysis, since mass modification can increase resolution of a mass spectrum and allow for analysis of two or more different target polypeptides by multiplexing.

A mass modification includes modifications such as, but not limited to, addition of a peptide or polypeptide fragment to the target polypeptide. For example, a target polypeptide can be mass modified by translating the target polypeptide to include additional amino acids, such as polyhistidine, polylysine or polyarginine. These modifications serve not only to aid in mass spectrometric analyses, but also can aid in purification, identification, immobilization. The modifications can be added post-translationally or can be included in the nucleic acid that encodes the resulting polypeptide.

In addition, where a plurality of target polypeptides is to be differentially mass modified, each target polypeptide in the plurality can be mass modified using a different polyhistidine sequence, for example, His-4, His-5, His-6, and so on. The use of such a mass modifying moiety provides the further advantage that the moiety acts as a tag peptide, which can be useful, for example, for isolating the target polypeptide attached thereto.

An advantage of the above processes is that they permit multiplexing to be performed on a plurality of polypeptides, and, therefore, are useful for determining the amino acid sequences of each of a plurality of polypeptides, particularly a plurality of target polypeptides.

More than one target nucleic acid can be amplified in the same reaction using several pairs of primers, each pair of which amplifies a different target nucleic acid sequence in a mixture of starting nucleic acids. Amplification can be performed simultaneously, provided the annealing temperature of all the primer pairs is sufficiently similar, or can be performed sequentially, starting with a first pair of primers having the lowest annealing temperature of several pairs of primers, then, after amplifying the first target nucleic acid, adding a second pair of primers having a higher annealing temperature and performing the second amplification at the higher temperature, and so on. Individual reactions with different primer pairs also can be performed, then the reaction products can be pooled. Using such methods provide a means for simultaneously determining the identity of more than one allelic variant of one or more polymorphic regions of one or more genes or genetic lesion.

A primer, for example, the forward primer, also can contain regulatory sequence elements necessary for translation of an RNA in a prokaryotic or eukaryotic system. In particular, where it is desirable to perform a translation reaction in a prokaryotic translation system, a primer can contain a prokaryotic ribosome binding sequence (Shine-Dalgarno sequence) located downstream of a promoter sequence and about 5 to 10 nucleotides upstream of the initiation codon. A prokaryotic ribosome binding sequence, for example, can have the nucleotide sequence, TAAG-GAGG (SEQ ID NO: 5).

A primer, generally the reverse primer, also can contain a sequence encoding a STOP codon in one or more of the reading frames, to assure proper termination of the target polypeptide. Further, by incorporating into the reverse primer sequences encoding three STOP codons, one into each of the three possible reading frames, optionally separated by several residues, additional mutations that occur downstream (3') of a mutation that otherwise results in premature termination of a polypeptide can be detected.

For preparing the primers for the amplification process, the nucleotide sequences of numerous target nucleic acids can be obtained from GenBank, or from relevant journal articles, patents or published patent applications. Oligonucleotide primers can be prepared using any suitable method, including, for example, organic synthesis of a nucleic acid from nucleoside derivatives, and can be performed in solution or on a solid support. The phosphotriester method, for example, has been utilized to prepare gene fragments or short genes. In the phosphotriester method, oligonucleotides are prepared, then joined together to form longer nucleic acids (see Narang et al., *Meth. Enzymol.* 68:90 (1979); U.S. Pat. No. 4,356,270). Primers also can be synthesized as described in U.S. Pat. Nos. 5,547,835; 5,605, 798 5,622,824.

Primers for amplification are selected such that the amplification reaction produces a nucleic acid that, upon transcription and translation, can result in a non-naturally occurring polypeptide, for example, a polypeptide encoded by an open reading frame that is not the open reading frame encoding the natural polypeptide. Accordingly, by appropriate primer design, in particular, by including an initiation codon in the desired reading frame and, if present, downstream of a promoter in the primer, a polypeptide produced from a target nucleic acid can be encoded by one of the two non-coding frames of the nucleic acid. Such a method can be used to shift out of frame STOP codons, which prematurely truncate the protein and exclude relevant amino acids, or to make a polypeptide containing an amino acid repeat more soluble.

A non-naturally occurring target polypeptide also can be encoded by ;5' or 3' non-coding region of an exonic region of a nucleic acid; by an intron; or by a regulatory element such as a promoter sequence that contains, in one of the six frames (3 frames per strand), at least a portion of an open reading frame. In these situations, one primer for amplification of the target nucleic acid contains a promoter and an initiation codon, such that the amplified nucleic acid can be transcribed and translated in vitro. Thus, a method for determining the identity of a target polypeptide, as disclosed herein, permits the determination of the identity of a nucleotide sequence located in any region of a chromosome, provided a polypeptide of at least 2 amino acids, generally at least 3 or 4 amino acids, particularly at least 5 amino acids, is encoded by one of the six frames of the polynucleotide.

Immobilization of a Polypeptide to a Solid Support

For mass spectrometric analyses, a target polypeptide or other polypeptide of interest can be conjugated and immobilized to a solid support in order to facilitate manipulation of the polypeptide. Such supports are well known to those of skill in the art, and include any matrix used as a solid support for linking proteins. The support is selected to be impervious to the conditions of mass spectrometric analyses. Supports, which can have a flat surface or a surface with structures, include, but are not limited to, beads such as silica gel beads, controlled pore glass beads, magnetic beads, Dynabeads, Wang resin; Merrifield resin, SEPHADEX/SEPHAROSE beads or cellulose beads; capillaries: flat supports such as glass fiber filters, glass surfaces, metal surfaces (including steel, gold silver, aluminum, silicon and copper), plastic materials (including multiwell plates or membranes (formed, for example, of polyethylene, polypropylene, polyamide, polyvinylidene difluoride), wafers, combs, pins or needles (including arrays of pins suitable for combinatorial synthesis or analysis) or beads in an array of pits; wells, particularly nanoliter wells, in flat surfaces, including wafers such as silicon wafers; and wafers with pits, with or without filter bottoms. A solid support is appropriately functionalized for conjugation of the polypeptide and can be of any suitable shape appropriate for the support.

A solid support, such as a bead, can be functionalized for the immobilization of polypeptides, and the bead can be further associated with a solid support, if desired. Where a bead is to be conjugated to a second solid support, polypeptides can be immobilized on the functionalized support before, during or after the bead is conjugated to the second support.

A polypeptide of interest can be conjugated directly to a solid support or can be conjugated indirectly through a functional group present either on the support, or a linker attached to the support, or the polypeptide or both. For example, a polypeptide can be immobilized to a solid support due to a hydrophobic, hydrophilic or ionic interaction between the support and the polypeptide. Although such a method can be useful for certain manipulations such as for conditioning of the polypeptide prior to mass spectrometry, such a direct interaction is limited in that the orientation of the polypeptide is not known and can be random based on the position of the interacting amino acids, for example, hydrophobic amino acids, in the polypeptide. Thus, a polypeptide generally is immobilized in a defined orientation by conjugation through a functional group on either the solid support or the polypeptide or both.

A polypeptide of interest can be modified by adding an appropriate functional group to the carboxyl terminus or amino terminus of the polypeptide, or to an amino acid in the peptide, for example, to a reactive side chain, or to the peptide backbone. It should be recognized, however, that a naturally occurring amino acid normally present in the polypeptide also can contain a functional group suitable for conjugating the polypeptide to the solid support. For example, a cysteine residue present in the polypeptide can be used to conjugate the polypeptide to a support containing a sulfhydryl group, for example, a support having cysteine residues attached thereto, through a disulfide linkage. Other bonds that can be formed between two amino acids, include, for example, monosulfide bonds between two lanthionine residues, which are non-naturally occurring amino acids that can be incorporated into a polypeptide; a lactam bond formed by a transamidation reaction between the side chains of an acidic amino acid and a basic amino acid, such as between the $\gamma$-carboxyl group of Glu (or,$\beta$-carboxyl group of Asp) and the $\epsilon$-amino group of Lys; or a lactone bond produced, for example, by a crosslink between the hydroxy group of Ser and the $\gamma$-carboxyl group of Glu (or $\beta$-carboxyl group of Asp). Thus, a solid support can be modified to contain a desired amino acid residue, for example, a Glu residue, and a polypeptide having a Ser residue, particularly a Ser residue at the carboxyl terminus or amino terminus, can be conjugated to the solid support through the formation of a lactone bond. It should be recognized, however, that the support need not be modified to contain the particular amino acid, for example, Glu, where it is desired to form a lactone-like bond with a Ser in the polypeptide, but can be modified, instead, to contain an accessible carboxyl group, thus providing a function corresponding to the $\gamma$-carboxyl group of Glu.

A polypeptide of interest also can be modified to facilitate conjugation to a solid support, for example, by incorporating a chemical or physical moiety at an appropriate position in the polypeptide, generally the C-terminus or N-terminus. The artisan will recognize, however, that such a modification, for example, the incorporation of a biotin moiety, can affect the ability of a particular reagent to interact specifically with the polypeptide and, accordingly, will consider this factor, if relevant, in selecting how best to modify a polypeptide of interest.

In one aspect of the processes provided herein, a polypeptide of interest can be covalently conjugated to a solid support and the immobilized polypeptide can be used to capture a target polypeptide, which binds to the immobilized polypeptide. The target polypeptide then can be released from immobilized polypeptide by ionization or volatization for mass spectrometry, whereas the covalently conjugated polypeptide remains bound to the support.

Accordingly, a method to determine the identity of polypeptides that interact specifically with a polypeptide of interest is provided. For example, such a process can be used to determine the identity of target polypeptides obtained from one or more biological samples that interact specifically with the immobilized polypeptide of interest. Such a process also can be used, for example, to determine the identity of binding proteins such as antibodies that bind to the immobilized polypeptide antigen of interest, or receptors that bind to an immobilized polypeptide ligand of interest, or the like. Such a process can be useful, for example, for screening a combinatorial library of modified target polypeptides such as modified antibodies, antigens, receptors, hormones, or other polypeptides to determine the identity of those target polypeptides that interact specifically with the immobilized polypeptide.

In one aspect of the processes provided herein, a polypeptide of interest can be covalently conjugated to a solid support and the immobilized polypeptide can be used to capture a target polypeptide, which binds to the immobilized polypeptide. The target polypeptide then can be released from immobilized polypeptide by ionization or volatization for mass spectrometry, whereas the covalently conjugated polypeptide remains bound to the support.

Accordingly, a process is provided to determine the identity of polypeptides that interact specifically with a polypeptide of interest. For example, such a process can be used to determine the identity of target polypeptides obtained from one or more biological samples that interact specifically with the immobilized polypeptide of interest. Such a process also can be used, for example, to determine the identity of binding proteins such as antibodies that bind to the immobilized polypeptide antigen of interest, or receptors that bind to an immobilized polypeptide ligand of interest, or the like. Such a process can be useful, for example, for screening a combinatorial library of modified target polypeptides such as modified antibodies, antigens, receptors, hormones, or other polypeptides to determine the identity of those target polypeptides that interact specifically with the immobilized polypeptide.

A polypeptide of interest can be conjugated to a solid support, which can be selected based on advantages that can be provided. Conjugation of a polypeptide to a support, for example, provides the advantage that a support has a relatively large surface area for immobilization of polypeptides. A support, such as a bead, can have any three dimensional structure, including a surface to which a polypeptide, functional group, or other molecule can be attached. If desired, a support, such as a bead, can have the additional characteristic that it can be conjugated further to a different solid support, for example, to the walls of a capillary tube. A support useful for the disclosed processes or kits generally has a size in the range of about 1 to about 100 μm in diameter; can be made of any insoluble or solid material, as disclosed above; and can be a swellable bead, for example, a polymeric bead such as Wang resin, or a non-swellable bead such as a controlled pore glass.

A solid surface also can be modified to facilitate conjugation of a polypeptide of interest. A thiol-reactive functionality is particularly useful for conjugating a polypeptide to a solid support. A thiol-reactive functionality is a chemical group that can rapidly react with a nucleophilic thiol moiety to produce a covalent bond, for example, a disulfide bond or a thioether bond. In general, thiol groups are good nucleophiles and, therefore, thiol-reactive functionalities generally are reactive electrophiles. A variety of thiol-reactive functionalities are known in the art, including, for example, haloacetyls such as iodoacetyl; diazoketones; epoxy ketones, α- and β-unsaturated carbonyls such as α-enones and βenones; and other reactive Michael acceptors such as maleimide; acid halides; benzyl halides; and the like. A free thiol group of a disulfide, for example, can react with a free thiol group by disulfide bond formation, including by disulfide exchange. Reaction of a thiol group can be temporarily prevented by blocking with an appropriate protecting group, as is conventional in the art (see Greene and Wuts "Protective Groups in Organic Synthesis" 2nd ed. (John Wiley & Sons 1991)).

Reducing agents that are useful for reducing a polypeptide containing a disulfide bond include tris-(2-carboxyethyl) phosphine (TCEP), which generally is used in a concentration of about 1 to 100 mM, usually about 10 mM, and is reacted at a pH of about 3 to 6, usually about pH 4.5, a temperature of about 20 to 45° C., usually about 37° C., for about 1 to 10 hours, usually about 5 hours); dithiothreitol, which generally is used in a concentration of about 25 to 100 mM, and is reacted at a pH of about 6 to 10, usually about pH 8, a temperature of about 25 to 45° C., usually about 37° C., for about 1 to 10 hours, usually about 5 hours. TCE provides an advantage in that it is reactive at a low pH, which effectively protonates thiols, thus suppressing nucleophilic reactions of thiols and resulting in fewer side reactions than with other disulfide reducing agents.

A thiol-reactive functionality such as 3-mercaptopropyltriethoxysilane can be used to functionalize a silicon surface with thiol groups. The amino functionalized silicon surface then can be reacted with a heterobifunctional reagent such as N-succinimidyl (4-iodacetyl) aminobenzoate (SIAB) (Pierce; Rockford Ill.). If desired, the thiol groups can be blocked with a photocleavable protecting group, which then can be selectively cleaved, for example, by photolithography, to provide portions of a surface activated for immobilization of a polypeptide of interest. Photocleavable protecting groups are known in the art (see, for example, published International PCT application No. WO 92/10092; McCray et al., *Ann. Rev. Biophys. Biophys. Chem.* 18:239–270 (1989)) and can be selectively deblocked by irradiation of selected areas of the surface using, for example, a photolithography mask.

Linkers

As noted herein, the polypeptide can be linked either directly to the support or via a linking moiety or moieties. Any linkers known to those of skill in the art to be suitable for linking peptides or amino acids to supports, either directly or via a spacer, may be used. Linkers, include, Rink amide linkers (see, e.g. Rink (1976) *Tetrahedron Letters* 28:3787), trityl chloride linkers (see, e.g., Leznoff (1978) *Ace. Chem. Res.* 11:327), Merrifield linkers (see, e.g., Bodansky et al. (1976) *Peptide Synthesis,* Academic Press, 2nd edition, New York). For example, trityl linkers are known (see, e.g., U.S. Pat. Nos. 5,410,068 and 5,612,474). Amino trityl linkers (see, FIG. 3) are also known (see, e.g., U.S. Pat. No. 5,198,531). Linkers that are suitable for chemically linking peptides to supports, include disulfide bonds, thioether bonds, hindered disulfide bonds, and covalent bonds between free reactive groups, such as amine and thiol groups. These bonds can be produced using heterobifunctional reagents to produce reactive thiol groups on one or both of the polypeptides and then reacting the thiol groups on one polypeptide with reactive thiol groups or amine groups on the other. Other linkers include, acid cleavable linkers, such as bismaleimideothoxy propane, acid labile-transferrin conjugates and adipic acid diihydrazide, that would be cleaved in more acidic intracellular compartments; photocleavable cross linkers that are cleaved by visible or UV light, RNA linkers that are cleavable by ribozymes and other RNA enzymes, and linkers, such as the various domains, such as $C_H1$, $C_H2$, and $C_H3$, from the constant region of human $IgG^1$ (see, Batra et al. (1993) *Molecular Immunol.* 30:379–386).

Any linker known to one skilled in the art for immobilizing a polypeptide to a solid support can be used in a process as disclosed herein. Combinations of any linkers are also contemplated herein. For example, a linker that is cleavable under mass spectrometric conditions, such as a silyl linkage or photocleavable linkage, can be combined with a linker, such as an avidin biotin linkage, that is not cleaved under these conditions, but may be cleaved under other conditions.

A polypeptide of interest can be attached directly to a support of via a linker. For example, the polypeptide can be conjugated to a support, such as a bead, through means of a variable spacer. In addition, the conjugation can be directly cleavable, for example, through a photocleavable linkage such as a streptavidin or avidin to biotin interaction, which can be cleaved by a laser as occurs for mass spectrometry, or indirectly through a photocleavable linker (see U.S. Pat. No. 5,643,722) or an acid labile linker, heat sensitive linker, enzymatically cleavable linker or other such linker.

A linker can provide a reversible linkage such that it is cleaved under the conditions of mass spectrometry. Such a linker can be, for example, a photocleavable bond such as a charge transfer complex or a labile bond formed between relatively stable organic radicals. A linker (L) on a polypeptide can form a linkage, which generally is a temporary linkage, with a second functional group (L') on the solid support. Furthermore, where the polypeptide of interest has a net negative charge, or is conditioned to have such a charge, the linkage can be formed with L' being, for example, a quaternary ammonium group. In this case, the surface of the solid support carries a negative charge that repels the negatively charged polypeptide, thereby facilitating desorption of the polypeptide for mass spectrometric analysis. Desorption can occur due to the heat created by the laser pulse or, where L' is a chromophore, by specific absorption of laser energy that is in resonance with the chromophore.

A linkage (L-L') can be, for example, a disulfide bond, which is chemically cleavable by mercaptoethanol or dithioerythrol; a biotin/streptavidin linkage, which can be photocleavable; a heterobifunctional derivative of a trityl ether group, which can be cleaved by exposure to acidic conditions or under conditions of mass spectrometry (Köster et al., "A Versatile Acid-Labile Linker for Modification of Synthetic Biomolecules," *Tetrahedron Lett.* 31:7095 (1990)); a levulinyl-mediated linkage, which can be cleaved under almost neutral conditions with a hydrazinium/acetate buffer; an arginine-arginine or a lysine-lysine bond, either of which can be cleaved by an endopeptidase such as trypsin; a pyrophosphate bond, which can be cleaved by a pyrophosphatase; or a ribonucleotide bond, which can be cleaved using a ribonuclease or by exposure to alkali condition.

The functionalities, L and L', can also form a charge transfer complex, thereby forming a temporary L-L' linkage.

Since the "charge-transfer band" can be determined by UV/vis spectrometry (see Foster, "Organic Charge Transfer Complexes" (Academic Press 1969)), the laser energy can be tuned to the corresponding energy of the charge-transfer wavelength and specific desorption from the solid support can be initiated. It will be recognized that several combinations of L and L' can serve this purpose and that the donor functionality can be on the solid support or can be coupled to the polypeptide to be detected or vice versa.

A reversible L-L' linkage also can be generated by homolytically forming relatively stable radicals. Under the influence of the laser pulse, desorption, as well as ionization, can take place at the radical position. Various organic radicals can be selected such that, in relation to the dissociation energy needed to homolytically cleave the bond between the radicals, a corresponding laser wavelength can be selected (see Wentrup, "Reactive Molecules" (John Wiley & Sons 1984)).

Other linkers include are those that can be incorporated into fusion proteins and expressed in a host cell. Such linkers may be selected amino acids, enzyme substrates, or any suitable peptide. The linker may be made, for example, by appropriate selection of primers when isolating the nucleic acid. Alternatively, they may be added by post translational modification of the protein of interest.

In particular, selectively cleavable linkers, including photocleavable linkers, acid cleavable linkers, acid-labile linkers, and heat sensitive linkers are useful. Acid cleavable linkers include, for example, bismaleimideothoxy propane, adipic acid dihydrazide linkers (see Fattom et al., *Infect. Immun.* 60:584–589 (1992)), and acid labile transferrin conjugates that contain a sufficient portion of transferrin to permit entry into the intracellular transferrin cycling pathway (see Welhöner et al., *J. Biol. Chem.* 266:4309–4314 (1991)).

FIG. 2 shows a preferred embodiment of a method of orthogonal capture, cleavage and MALDI analysis of a peptide. This embodiment demonstrates capture through the amino-terminus of the peptide. As shown, the peptide is captured onto a surface of a support through the use of a diisopropylsilyl diether group. Other silyl diether groups, including, but not limited to, dialkylsilyl, diarylsilyl and alkylarylsilyl, may also be used. Reaction of a hydroxylated support surface with diisopropylsilyl dichloride and a hydroxyester provides the starting surface-bound diisopropylsilyl diether ester.

With reference to the FIGURE, $R^3$ is any attachment moiety, resulting from a support that has been derivatized for linkage, with a derivatizing group that has a hydroxyl group available for reaction. $R^3$ also can be a linkage, such as biotin-streptavidin or biotin-avidin. $R^3$ includes groups such as polyethylene glycol (PEG), an alkylene or arylene group.

The hydroxylated support surface may be prepared by methods that are well-known to those of skill in the art. For example, N-succinimidyl(4-iodacetyl) aminobenzoate (SIAB). Other agents as linkers ($R^3$) include, but are not limited to, dimaleimide, dithio-bis-nitrobenzoic acid (DTNB), N-succinimidyl-S-acetyl-thioacetate (SATA), N-succinimidyl-3-(2-pyridyldithiol propionate (SPDP), succinimidyl 4-(N-maleimidomethyl)cyclohexane-1-carboxylate (SMCC) ad 6-hydrazinonicotimide (HYNIC) may also be used in the novel process. For further examples of cross-linking reagents, see, e.g., Wong "Chemistry of Protein Conjugation and Cross-Linking," CRC Press (1991), and Hermanson, *Bioconjugate Techniques" Academic Press* (1995). Hydroxyesters that may be used include, but are not limited to, hydroxyacetate (glycolate), α-, β-, γ-, . . . , ω-hydroxyalkanoates, ω-hydroxy(polyethyleneglycol) COOH, hydroxybenzoates, hydroxyarylalkanoates and hydroxyalkylbenzoates. Thus, with reference to FIG. 2, $R^4$ may be any divalent group that is 2 or more bonds in length, such as $(CH_2)_n$, where n is 2 or more, and polyethylene glycol. The derivatized support is then reacted with the desired peptide to capture the peptide on the support with loss of $R^1OH$. The peptide may be reacted directly with the ester group in embodiments where $COOR^1$ is an active ester group. In these preferred embodiments, $R^1$ is selected from groups such as, but not limited to, N-succinimidyl, sodium 3-sulfo-N-succinimidyl and 4-nitrophenyl. In other embodiments, the ester is saponified, e.g., with hydroxide, to provide the corresponding acid. This acid is then coupled with the amino-terminus of the peptide under standard peptide coupling conditions (e.g., 1-(3-dimethylaminopropyl)-3-ethylcarbodiimide hydrochloride (EDC) and N-hydroxysuccinimide (NHS)). The captured peptide is then truncated (fragmented) by reaction with an enzyme or reagent specific for a given amide bond of the peptide. Cleavage of the truncated peptide, containing an N-terminal fragment of the original peptide, from the support is then accomplished by reaction with mild acid. Acids suitable for this cleavage include, but are not limited to, acetic acid, trifluoroacetic acid, para-toluenesulfonic acid and mineral acids. A preferred acid is 3-hydroxypicolinic acid, which is also a suitable matrix for the subsequent MALDI analysis.

Figure 3:
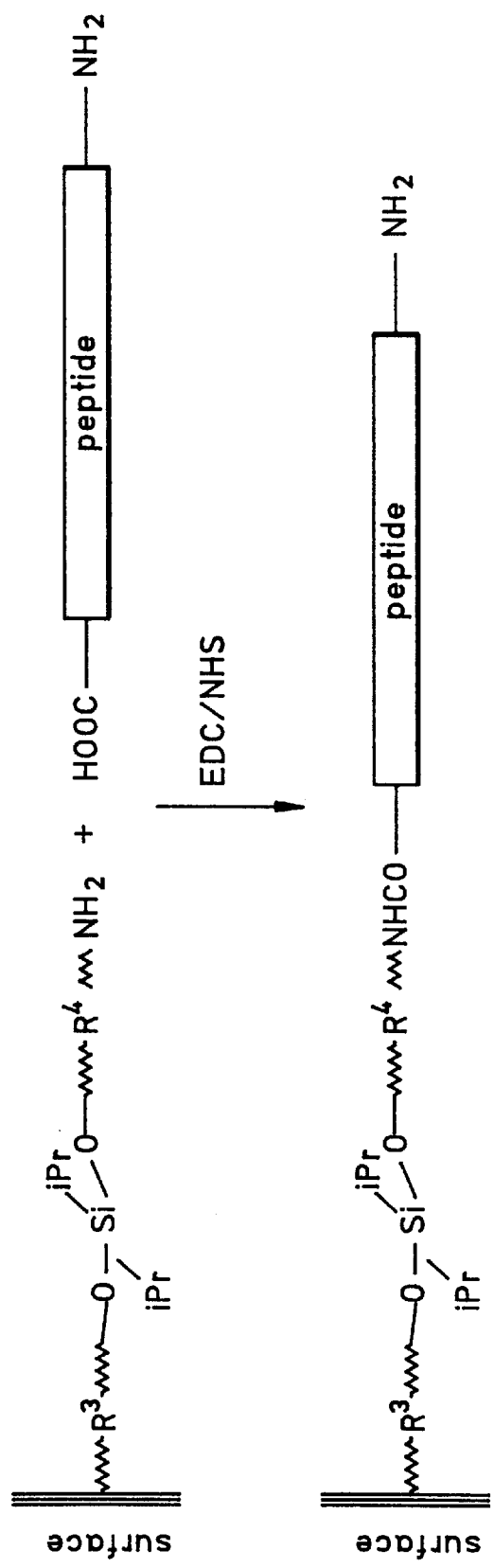
FIG. 3 illustrates additional linkers and capture strategies for reversibly immobilizing a polypeptide on a solid surface.

FIG. 3 illustrates other preferred linkers and capture strategies for MALDI analysis of peptides. As shown, the peptide may be captured through the carboxy terminus by employing an amino-derivatized support. The starting amino-derivatized support may be prepared by reacting a hydroxylated support surface with diisopropylsilyl dichloride and an aminoalcohol. Aminoalcohols that may be used include, but are not limited to, α-, β-, γ-, . . . , ω-aminoalkanols, ω-hydroxy(polyethyleneglycol)NH$_2$, hydroxyanilines, hydroxyarylalkylamines and hydroxyalkylanilined. Thus, with reference to FIG. 3, $R^4$ may be any divalent group that is 2 or more bonds in length. Capture of the peptide by the amino-derivatized support is achieved by dehydrative coupling of the peptide with the amino group. Such peptide coupling conditions are well-known to those of skill in the art. Illustrated is one set of conditions for capture of the peptide (i.e., 1-(3-dimethylaminopropyl)-3-ethylcarbodiimide hydrochloride (EDC) and N-hydroxysuccinimide (NHS)). The captured peptide may then be truncated, cleaved from the support, and analyzed as shown in FIG. 2.

Also illustrated in FIG. 3 are other linkers useful in capturing peptides on supports for MALDI analysis. For example, trityl-containing linkers, functionallized with either ester or amino moieties, may be used to capture peptides at the amino or carboxy terminus, respectively. Other linkers known to those of skill in art, e.g., photocleavable linkers, are also available for use in capturing the peptides on the support surface.

Photocleavable Linkers

Photocleavable linkers are provided. The linkers contain o-nitrobenzyl moieties and phosphate linkages, which allow for complete photolytic cleavage of the conjugates within minutes upon UV irradiation. The UV wavelengths used are selected so that the irradiation will not damage the polypeptides and generally are about 350 to 380 nm, usually about 365 nm.

A photocleavable linker can have the general structure of formula I:

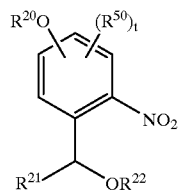

(I)

where $R^{20}$ is ω-(4,4'-dimethoxytrityloxy)alkyl or ω-hydroxyalkyl; $R^{21}$ is selected from hydrogen, alkyl, aryl, alkoxycarbonyl, aryloxycarbonyl and carboxy; $R^{22}$ is hydrogen or (dialkylamino)(ω-cyanoalkoxy)P—; t is 0–3; and $R^{50}$ is alkyl, alkoxy, aryl or aryloxy.

A photocleavable linker also can have the formula II:

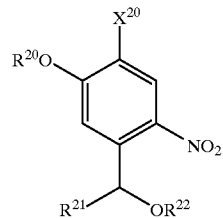

(II)

where $R^{20}$ is ω-(4,4'-dimethoxytrityloxy)alkyl, ω-hydroxyalkyl or alkyl; $R^{21}$ is selected from hydrogen, alkyl, aryl, alkoxycarbonyl, aryloxycarbonyl and carboxy; $R^{22}$ is hydrogen or (dialkylamino)(ω-cyanoalkoxy)P—; and $X^{20}$ is hydrogen, alkyl or $OR^{20}$.

In a particular photocleavable linker, $R^{20}$ is 3-(4,4'-dimethoxytrityloxy)propyl, 3-hydroxypropyl or methyl; $R^{21}$ is selected from hydrogen, methyl and carboxy; $R^{22}$ is hydrogen or (diisopropylamino) (2-cyanoethoxy)P—; and $X^{20}$ is hydrogen, methyl or $OR^{20}$. In another photocleavable, $R^{20}$ is 3-(4,4'-dimethoxytrityloxy)propyl; $R^{21}$ is methyl; $R^{22}$ is (diisopropylamino)(2-cyanoethoxy)P—; and $X^{20}$ is hydrogen. In still another photocleavable linker, $R^{20}$ is methyl; $R^{21}$ is methyl; $R^{22}$ is (diisopropylamino)(2-cyanoethoxy)P—; and $X^{20}$ is 3-(4,4'-dimethoxytrityloxy) propoxy.

A photocleavable linker also can have the general formula of formula III:

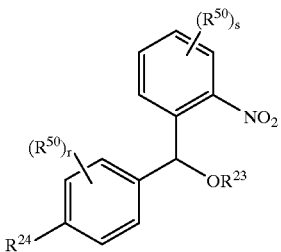

(III)

where $R^{23}$ is hydrogen or (dialkylamino)(ω-cyanoalkoxy) P—; and $R^{24}$ is selected from ω-hydroxyalkoxy, ω-(4,4'-dimethoxytrityloxy)alkoxy, ω-hydroxyalkyl and ω-(4,4'-dimethoxytrityloxy)alkyl, and is unsubstituted or substituted on the alkyl or alkoxy chain with one or more alkyl groups; r and s are each independently 0–4; and $R^{50}$ is alkyl, alkoxy, aryl or aryloxy.

In particular photocleavable linkers, $R^{24}$ is ω-hydroxyalkyl or ω-(4,4'-dimethoxytrityloxy)alkyl, and is substituted on the alkyl chain with a methyl group. In another photocleavable linker, $R^{23}$ is hydrogen or (diisopropylamino)(2-cyanoethoxy)P—; and $R^{24}$ is selected from 3-hydroxypropoxy, 3-(4,4'-dimethoxytrityloxy) propoxy, 4-hydroxybutyl, 3-hydroxy-1-propyl, 1-hydroxy-2-propyl, 3-hydroxy-2-methyl-1-propyl, 2-hydroxyethyl, hydroxymethyl, 4-(4,4'-dimethoxytrityloxy)butyl, 3-(4,4'-dimethoxytrityloxy)-1-propyl, 2-(4,4'-dimethoxytrityloxy) ethyl, 1-(4,4'-dimethoxytrityloxy)-2-propyl, 3-(4,4'-dimethoxytriyloxy)-2-methyl-1-propyl and 4,4'-dimethyoxytrityloxymethyl. In still another photocleavable linker, $R^{23}$ is (diisopropylamino)(2-cyanoethoxy)P—; r and s are O; and $R^{24}$ is selected from 3-(4,4'-dimethoxytrityloxy) propoxy, 4-(4,4'-dimethoxytrityloxy)butyl, 3-(4,4'-dimethoxytrityloxy)propyl, 2-(4,4'-dimethoxytrityloxy) ethyl, 1-(4,4'-dimethoxytrityloxy)-2-propyl, 3-(4,4'-dimethoxytriyloxy)-2-methyl-1-propyl and 4,4'-dimethyoxytrityloxymethyl. $R^{24}$ is most preferably 3-(4,4'-dimethoxytrityloxy)propoxy.

Preparation of the Photocleavable Linkers
Preparation of Photocleavable Linkers of Formulae I or II Photocleavable linkers of formulae I or II can be prepared by the methods described below, by minor modification of the methods by choosing the appropriate starting materials or by any other methods known to those of skill in the art. Detailed procedures for the synthesis of photocleavable linkers of formula II are provided in Examples 2 and 3.

In the photocleavable linkers of formula II, where $X^{20}$ is hydrogen, the linkers can be prepared in the following manner. Alkylation of 5-hydroxy-2-nitrobenzaldehyde with an ω-hydroxyalkyl halide, for example, 3-hydroxypropyl bromide, followed by protection of the resulting alcohol, for example, as a silyl ether, provides a 5-(ω-silyloxyalkoxy)-2-nitrobenzaldehyde. Addition of an organometallic to the aldehyde affords a benzylic alcohol. Organometallics that can be used include trialkylaluminums (for linkers where $R^{21}$ is alkyl) such as trimethylaluminum; borohydrides (for linkers where $R^{21}$ is hydrogen) such as sodium borohydride; or metal cyanides (for linkers where $R^{21}$ is carboxy or alkoxycarbonyl) such as potassium cyanide. In the case of the metal cyanides, the product of the reaction, a cyanohydrin, is hydrolyzed under either acidic or basic conditions in the presence of either water or an alcohol to afford the compounds of interest.

The silyl group of the side chain of the resulting benzylic alcohols can be exchanged for a 4,4'-dimethoxytriyl group by desilylation using, for example, tetrabutylammonium fluoride, to give the corresponding alcohol, followed by reaction with 4,4'-dimethoxytrityl chloride. Reaction, for example, with 2-cyanoethyl diisopropylchlorophosphoramidite affords the linkers where $R^{22}$ is (dialkylamino)(ω-cyanoalkoxy)P—.

A specific example of a synthesis of a photocleavable linker of formula II is shown in the following scheme, which also demonstrates use of the linker in oligonucleotide synthesis. This scheme is intended to be illustrative only and in no way limits the scope of the methods herein. Experimental details of these synthetic transformations are provided in the Examples.

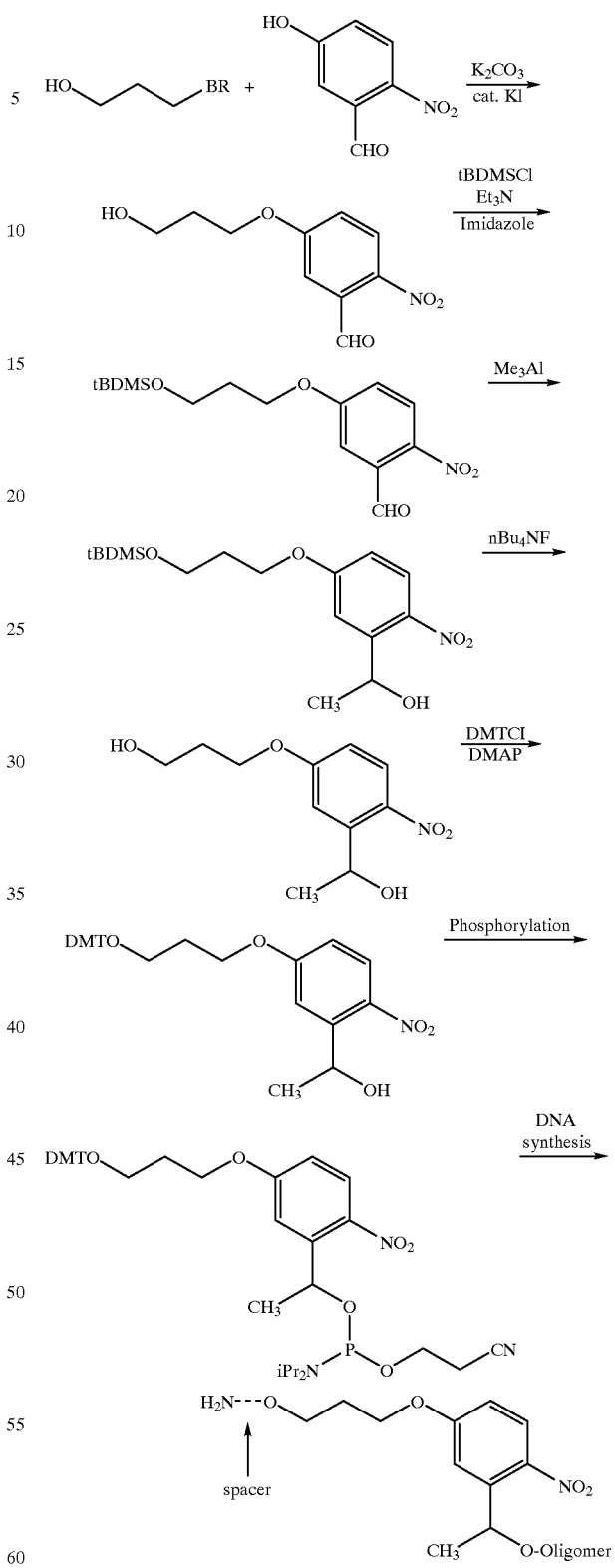

Synthesis of the linkers of formula II, where $X^{20}$ is $OR^{20}$, 3,4-dihydroxyacetophenone is protected selectively at the 4-hydroxyl by reaction, for example, with potassium carbonate and a silyl chloride. Benzoate esteres, propiophenones, butyrophenones, and the like can be used in place of the acetophenone. The resulting 4-silyloxy-3- hydroxyacetophenone then is alkylated at the with an alkyl halide (for linkers where $R^{20}$ is alkyl) at the 3-hydroxyl and desilylated, for example, with tetrabuylammonium fluoride to afford a 3-alkoxy-4-hydroxyacetophenone. This compound then is alkylated at the 4-hydroxyl by reaction with an ω-hydroxyalkyl halide, for example, 3-hydroxypropyl bromide, to give a 4-(ω-hydroxyalkoxy)-3-alkoxy acetophenone. The side chain alcohol is then protected as an ester, for example, an acetate. This compound is then nitrated at the 5-position, for example, with concentrated nitric acid to provide the corresponding 2-nitroacetophenones. Saponification of the side chain ester, for example, with potassium carbonate, and reduction of the ketone, for example, with sodium borohydride, in either order gives a 2-nitro-4-(ω-hydroxyalkoxy)-5-alkoxybenzylic alcohol.

Selective protection of the side chain alcohol as the corresponding 4,4'-dimethoxytrityl ether is then accomplished by reaction with 4,4'-dimethoxytrityl chloride. Further reaction, for example, with 2-cyanoethyl diisopropylchlorophosphoramidite affords the linkers where $R^{22}$ is (dialkylamino)(ω-cyanoalkoxy)P—.

A specific example of the synthesis of a photocleavable linker of formula II is shown the following scheme. This scheme is intended to be illustrative only and in no way limit the scope of the methods herein.

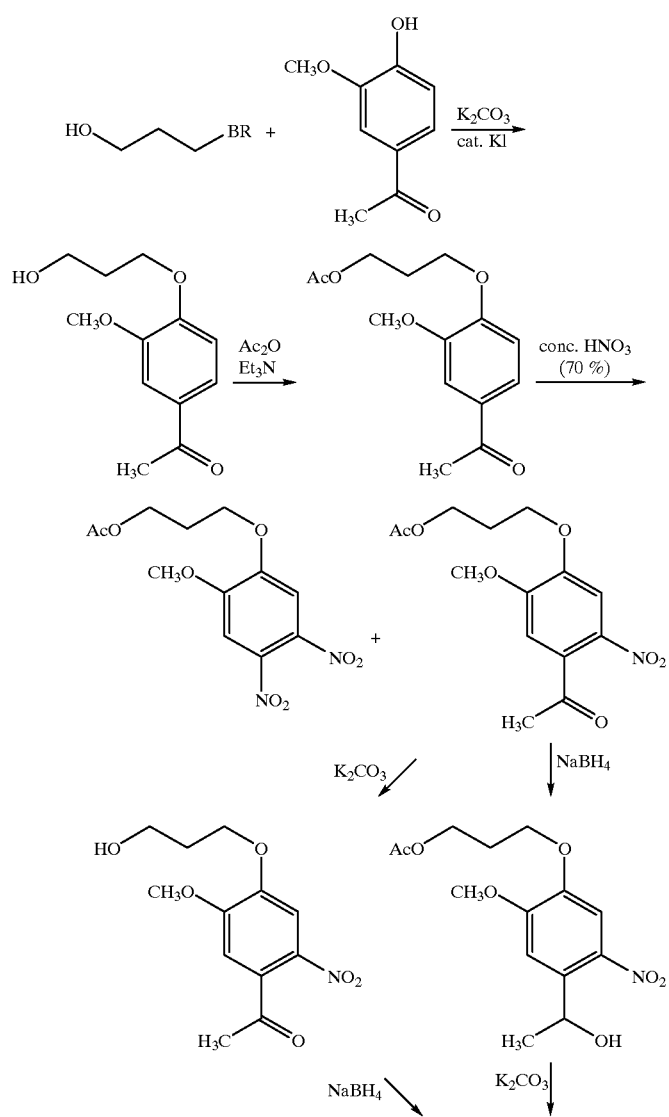

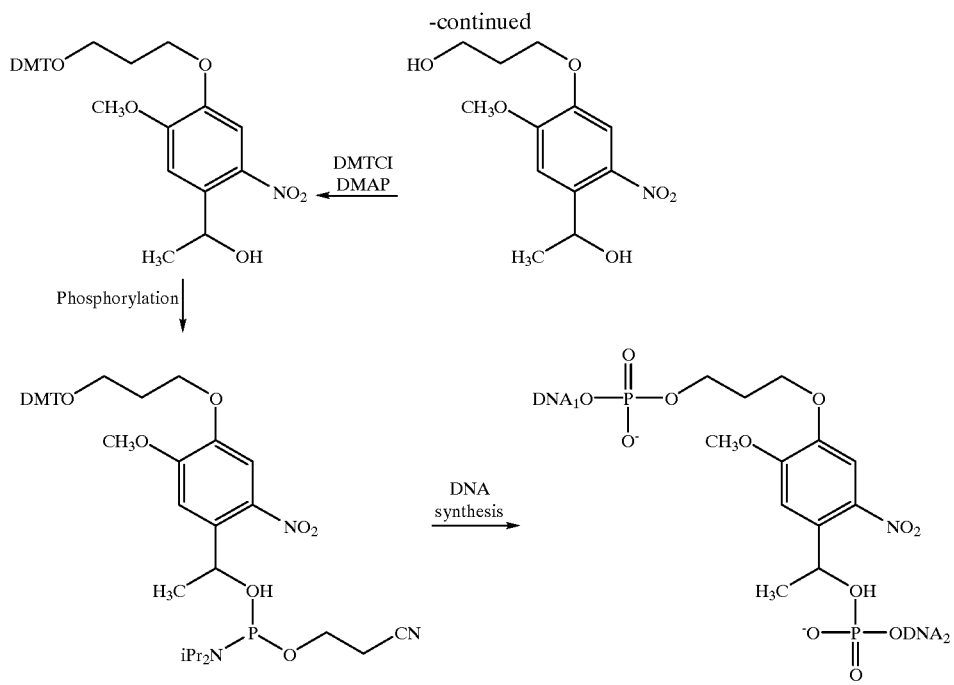

Preparation of Photocleavable Linkers of Formula III

Photocleavable linkers of formula III can be prepared by the methods disclosed herein, by minor modification of the methods by choosing appropriate starting materials, or by other methods known to those of skill in the art.

In general, photocleavable linkers of formula III are prepared from ω-hydroxyalkyl- or alkoxyaryl compounds, in particular ω-hydroxy-alkyl or alkoxy-benzenes. These compounds are commercially available, or may be prepared from an ω-hydroxyalkyl halide, for example, 3-hydroxypropyl bromide, and either phenyllithium (for the ω-hydroxyalkylbenzenes) or phenol (for the ω-hydroxyalkoxybenzenes). Acylation of the ω-hydroxyl group, for example, as an acetate ester, followed by Friedel-Crafts acylation of the aromatic ring with 2-nitrobenzoyl chloride provides a 4-(ω-acetoxy-alkyl or alkoxy)-2-nitro benzophenone. Reduction of the ketone, for example, with sodium borohydride, and saponification of the side chain ester are performed in either order to afford a 2-nitrophenyl-4-(hydroxy-alkyl or alkoxy)phenylmethanol. Protection of the terminal hydroxyl group as the corresponding 4,4'-dimethoxytrityl ether is achieved by reaction with 4,4'-dimethoxytrityl chloride. The benzylic hydroxyl group is then reacted, for example, with 2-cyanoethyl diisopropyl-chlorophosphoramidite to afford linkers of formula II where $R^{23}$ is (dialkylamino)(ω-cyanoalkoxy)P—.

Other photocleavable linkers of formula III can be prepared by substituting 2-phenyl-1-propanol or 2-phenylmethyl-1-propanol for the ω-hydroxy-alkyl or alkoxy-benzenes in the above synthesis. These compounds are commercially available, but also can be prepared by reaction, for example, of phenylmagnesium bromide or benzylmagnesium bromide, with the requisite oxirane (propylene oxide) in the presence of catalytic cuprous ion.

Chemically Cleavable Linkers

A variety of chemically cleavable linkers also can be used to link a polypeptide to a solid support. Acid-labile linkers are particularly useful chemically cleavable linkers for mass spectrometry, especially for MALDI-TOF, because the acid labile bond is cleaved during conditioning of the target polypeptide upon addition of a 3-HPA matrix solution. The acid labile bond can be introduced as a separate linker group, for example, an acid labile trityl group, or can be incorporated in a synthetic linker by introducing one or more silyl bridges using diisopropylsilyl, thereby forming a diisopropylsilyl linkage between the polypeptide and the solid support. The diisopropylsilyl linkage can be cleaved using mildly acidic conditions such as 1.5% trifluoroacetic acid (TFA) or 3-HPA/1% TFA MALDI-TOF matrix solution. Methods for the preparation of diisopropylsilyl linkages and analogs thereof are well known in the art (see, for example, Saha et al., *J. Org. Chem.* 58:7827–7831 (1993)).

As disclosed herein, a polypeptide of interest can be conjugated to a solid support such as a bead. In addition, a first solid support such as a bead also can be conjugated, if desired, to a second solid support, which can be a second bead or other support, by any suitable means, including those disclosed herein for conjugation of a polypeptide to a support. Accordingly, any of the conjugation methods and means disclosed herein with reference to conjugation of a polypeptide to a solid support also can be applied for conjugation of a first support to a second support, where the first and second solid support can be the same or different.

Appropriate linkers, which can be crosslinking agents, for use for conjugating a polypeptide to a solid support include a variety of agents that can react with a functional group present on a surface of the support, or with the polypeptide, or both. Reagents useful as crosslinking agents include homobifunctional and, in particular, heterobifunctional reagents. Useful bifunctional crosslinking agents include, but are not limited to, N-succinimidyl(4-iodoacetyl) aminobenzoate (SIAB), dimaleimide, dithio-bis-nitrobenzoic acid (DTNB), N-succinimidyl-S-acetyl-thioacetate (SATA), N-succinimidyl-3-(2-pyridyldithio) propionate (SPDP), succinimidyl 4-(N-maleimidomethyl)cyclohexane-1-carboxylate (SMCC) and 6-hydrazino-nicotimide (HYNIC).

A crosslinking agent can be selected to provide a selectively cleavable bond between a polypeptide and the solid support. For example, a photolabile crosslinker such as 3-amino-(2-nitrophenyl)propionic acid (Brown et al., *Molec. Divers.* 4–12 (1995); Rothschild et al., *Nucl. Acids Res.* 24:351–66 (1996); U.S. Pat. No. 5,643,722) can be employed as a means for cleaving a polypeptide from a solid support. Other crosslinking reagents are well known in the art (see, for example, Wong, "Chemistry of Protein Conjugation and Cross-Linking" (CRC Press 1991); Hermanson, supra, 1996).

A polypeptide can be immobilized on a solid support such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide.

In addition, a bifunctional trityl linker can be attached to the support, for example, to the 4-nitrophenyl active ester on a resin such as a Wang resin, through an amino group or a carboxyl group on the resin via an amino resin. Using a bifunctional trityl approach, the solid support can require treatment with a volatile acid such as formic acid or trifluoroacetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a mass spectrometer.

Hydrophobic trityl linkers also can be exploited as acid-labile linkers by using a volatile acid or an appropriate matrix solution, for example, a matrix solution containing 3-HPA, to cleave an amino linked trityl group from the polypeptide. Acid lability also can be changed. For example, trityl, monomethoxytrityl, dimethoxytrityl or trimethoxytrityl can be changed to the appropriate p-substituted, or more acid-labile tritylamine derivatives, of the polypeptide; i.e. trityl ether and tritylamine bonds to the can be made to the polypeptide. Accordingly, a polypeptide can be removed from a hydrophobic linker, for example, by disrupting the hydrophobic attraction or by cleaving tritylether or tritylamine bonds under acidic conditions, including, if desired, under typical mass spectrometry conditions, where a matrix such as 3-HPA acts as an acid.

As disclosed herein, a polypeptide can be conjugated to a solid support, for example, a bead, and the bead, either prior to, during or after conjugation of the polypeptide, can be conjugated to a second solid support, where one or both conjugations result in the formation of an acid-labile bond. For example, use of a trityl linker can provide a covalent or a hydrophobic conjugation, and, regardless of the nature of the conjugation, the trityl group is readily cleaved in acidic conditions. Orthogonally cleavable linkers also can be useful for binding a first solid support, for example, a bead to a second solid support, or for binding a polypeptide of interest to a solid support. Using such linkers, a first solid support, for example, a bead, can be selectively cleaved from a second solid support, without cleaving the polypeptide from the support; the polypeptide then can be cleaved from the bead at a later time. For example, a disulfide linker, which can be cleaved using a reducing agent such as DTT, can be employed to bind a bead to a second solid support, and an acid cleavable bifunctional trityl group could be used to immobilize a polypeptide to the support. As desired, the linkage of the polypeptide to the solid support can be cleaved first, for example, leaving the linkage between the first and second support intact. Trityl linkers can provide a covalent or hydrophobic conjugation and, regardless of the nature of the conjugation, the trityl group is readily cleaved in acidic conditions.

A first a solid support such as a bead can be conjugated to a second solid support using the methods, linkages and conjugation means disclosed herein. In addition, a bead, for example, can be bound to a second support through a linking group, which can be selected to have a length and a chemical nature such that high density binding of the beads to the solid support, or high density binding of the polypeptides to the beads, is promoted. Such a linking group can have, for example, "tree-like" structure, thereby providing a multiplicity of functional groups per attachment site on a solid support. Examples of such linking groups include polylysine, polyglutamic acid, penta-erythrole and tris-hydroxy-aminomethane.

A polypeptide can be conjugated to a solid support, or a first solid support also can be conjugated to a second solid support, through a noncovalent interaction. For example, a magnetic bead made of a ferromagnetic material, which is capable of being magnetized, can be attracted to a magnetic solid support, and can be released from the support by removal of the magnetic field. Alternatively, the solid support can be provided with an ionic or hydrophobic moiety, which can allow the interaction of an ionic or hydrophobic moiety, respectively, with a polypeptide, for example, a polypeptide containing an attached trityl group or with a second solid support having hydrophobic character.

A solid support also can be provided with a member of a specific binding pair and, therefore, can be conjugated to a polypeptide or a second solid support containing a complementary binding moiety. For example, a bead coated with avidin or with streptavidin can be bound to a polypeptide having a biotin moiety incorporated therein, or to a second solid support coated with biotin or derivative of biotin such as imino-biotin.

It should be recognized that any of the binding members disclosed herein or otherwise known in the art can be reversed with respect to the examples provided herein. Thus, biotin, for example, can be incorporated into either a polypeptide or a solid support and, conversely, avidin or other biotin binding moiety would be incorporated into the support or the polypeptide, respectively. Other specific binding pairs contemplated for use herein include, but are not limited to, hormones and their receptors, enzymes and their substrates, a nucleotide sequence and its complementary sequence, an antibody and the antigen to which it interacts specifically, and other such pairs knows to those skilled in the art.

Immobilization of one or more polypeptides of interest, particularly target polypeptides, facilitates manipulation of the polypeptides. For example, immobilization of the polypeptides to a solid support facilitates isolation of the polypeptides from a reaction, or transfer of the polypeptides during the performance of a series of reactions. As such, immobilization of the polypeptides can facilitate conditioning the polypeptides or mass modification of the polypeptides prior to performing mass spectrometric analysis.

Examples of preferred binding pairs or linker/interactions are provided in the Table.

TABLE

| LINKER/INTERACTION | EXAMPLES |
| --- | --- |
| streptavidin-biotin[a,c]/photolabile biotin[b] | biotinylated pin, avidin beads, photolabile biotin polypeptide |
| hydrophobic[a] | C18-coated pin, tritylated polypeptide |
| magnetic[a] | electromagnetic pin, steptavidin magnetic beads (e.g., DYNABEADS), |

TABLE-continued

| LINKER/INTERACTION | EXAMPLES |
| --- | --- |
| | biotin polypeptide |
| acid-labile linker[b] | glass pin, bifunctional trityl-linked DNA |
| amide bond(s)[c] | silicon wafer, Wang resin, amino-linked polypeptide |
| disulfide bond[a] | silicon wafer, beads are bound on the flat surface forming arrays or in arrays of nanoliter wells, thiol beads, thiolated polypeptide |
| photocleavable bond/linker | biotinylated pin/wafer, avidin beads, photolabile biotin polypeptide |
| thioether bond[c] | silicon wafer, beads are bound on the flat surface forming arrays or in arrays of nanoliter wells, thiolated peptide |

[a]these interactions are reversible.
[b]these non-reversible interactions are rapidly cleaved.
[c]unless cleavable-linkers are incorporated at some point in the scheme, only the complement of the solid-bound DNA can be analyzed in these schemes.

Conditioning a Polypeptide

Conditioning of a polypeptide prior to mass spectrometry can increase the resolution of a mass spectrum of the polypeptide, thereby facilitating determining the identity of a target polypeptide. A polypeptide can be conditioned, for example, by treating the polypeptide with a cation exchange material or an anion exchange material, which can reduce the charge heterogeneity of the polypeptide, thereby reducing or eliminating peak broadening. In addition, contacting a polypeptide with an alkylating agent such as alkyliodide, iodoacetamide, iodoethanol, or 2,3-epoxy-1-propanol, for example, can prevent the formation of disulfide bonds in the polypeptide, thereby increasing resolution of a mass spectrum of the polypeptide. Likewise, charged amino acid side chains can be converted to uncharged derivatives by contacting the polypeptides with trialkylsilyl chlorides, thus reducing charge heterogeneity and increasing resolution of the mass spectrum.

There are also means of improving resolution, particularly for shorter peptides, by incorporating modified amino acids that are more basic than the corresponding unmodified residues. Such modification in general increases the stability of the polypeptide during mass spectrometric analysis. Also, cation exchange chromatography, as well as general washing and purification procedures which remove proteins and other reaction mixture components away from the target polypeptide, can be used to clean up the peptide after in vitro translation and thereby increase the resolution of the spectrum resulting from mass spectrometric analysis of the target polypeptide.

Conditioning also can involve incorporating modified amino acids into the polypeptide, for example, mass modified amino acids, which can increase resolution of a mass spectrum. For example, the incorporation of a mass modified leucine residue in a polypeptide of interest can be useful for increasing the resolution (e.g., by increasing the mass difference) of a leucine residue from an isoleucine residue, thereby facilitating determination of an amino acid sequence of the polypeptide. A modified amino acid also can be an amino acid containing a particular blocking group, such as those groups used in chemical methods of amino acid synthesis. For example, the incorporation of a glutamic acid residue having a blocking group attached to the side chain carboxyl group can mass modify the glutamic acid residue and, provides the additional advantage of removing a charged group from the polypeptide, thereby further increasing resolution of a mass spectrum of a polypeptide containing the blocked amino acid.

Use of a Pin Tool to Immobilize a Polypeptide

The immobilization of a polypeptide of interest to a solid support using a pin tool can be particularly advantageous. Pin tools include those disclosed herein or otherwise known in the art (see, e.g., copending U.S. application Ser. Nos. 08/786,988 and 08/787,639, and International PCT application No. WO 98/20166).

A pin tool in an array, for example, a 4×4 array, can be applied to wells containing polypeptides of interest. Where the pin tool has a functional group attached to each pin tip, or a solid support, for example, functionalized beads or paramagnetic beads, are attached to each pin, the polypeptides in a well can be captured ($\geq 1$ pmol capacity). During the capture step, the pins can be kept in motion (vertical, 1–2 mm travel) to increase the efficiency of the capture. Where a reaction such as an in vitro transcription is being performed in the wells, movement of the pins can increase efficiency of the reaction.

Polypeptides of interest, particularly target polypeptides, are immobilized due to contact with the pin tool. Further immobilization can result by applying an electrical field to the pin tool. When a voltage is applied to the pin tool, the polypeptides are attracted to the anode or the cathode, depending on their net charge. Such a system also can be useful for isolating the polypeptides, since uncharged molecules remain in solution and molecules having a charge opposite to the net charge of the polypeptides are attracted to the opposite pole (anode or cathode). For more specificity, the pin tool (with or without voltage) can be modified to have conjugated thereto a reagent specific for the polypeptide of interest, such that only the polypeptides of interest are bound by the pins. For example, the pins can have nickel ions attached, such that only polypeptides containing a polyhistidine sequence are bound. Similarly, the pins can have antibodies specific for a target polypeptide attached thereto, or to beads that, in turn, are attached to the pins, such that only the target polypeptides, which contain the epitope recognized by the antibody, are bound by the pins.

Different pin conformations include, for example, a solid pin configuration, or pins with a channel or with a hole through the center, which can accommodate an optic fiber for mass spectrometer detection. The pin can have a flat tip or any of a number of configurations, including nanowell, concave, convex, truncated conic or truncated pyramidal, for example, a size 4 to 800 μm across×100 μm in depth. The individual pins, which can be any size desired, generally are as long as about 10 mm, usually about 5 mm long, and particularly about 1 mm long. The pins and mounting plate can be made of polystyrene, which can be one piece injection molded. Polystyrene is convenient for this use because it can be functionalized readily and can be molded to very high tolerances. The pins in a pin tool apparatus can be collapsible, for example, controlled by a scissor-like mechanism, so that the pins can be brought into closer proximity, reducing the overall size.

Captured polypeptides can be analyzed by a variety of means including, for example, spectrometric techniques such as UV/VIS, IR, fluorescence, chemiluminescence, NMR spectroscopy, mass spectrometry, or other methods known in the art, or combinations thereof. If conditions preclude direct analysis of captured polypeptides, the polypeptides can be released or transferred from the pins, under conditions such that the advantages of sample concentration are not lost. Accordingly, the polypeptides can be removed from the pins using a minimal volume of eluent, and without any loss of sample. Where the polypeptides are bound to the beads attached to the pins, the beads containing the polypeptides can be removed from the pins and measurements made directly from the beads.

Prior to determining the identity of a target polypeptide by mass spectrometry, a pin tool having the polypeptide attached thereto can be withdrawn and washed several times, for example, in ammonium citrate to condition the polypeptide prior to addition of matrix. The pins then can be dipped into matrix solution, with the concentration of matrix adjusted such that matrix solution adheres only to the very tips of the pins. Alternatively, the pin tool can be inverted and the matrix solution sprayed onto the tip of each pin using a microdrop device. The polypeptides also can be cleaved from the pin, for example, into a nanowell on a chip, prior to addition of matrix. For analysis directly from the pins, a stainless steel "mask" probe can be fitted over the pins, then the mask probe can be installed in the mass spectrometer.

Two mass spectrometer geometries can be used for accommodating a pin tool apparatus. A first geometry accommodates solid pins. In effect, the laser ablates a layer of material from the surface of the crystals, such that the resultant ions are accelerated and focused through the ion optics. A second geometry accommodates fibre optic pins, in which the laser strikes the samples from behind. In effect, the laser is focused onto the pin tool back plate and into a short optical fibre about 100 $\mu$m in diameter and about 7 mm in length to include thickness of the back plate. This geometry requires that the volatilized sample go through the depth of the matrix/bead mix, slowing and cooling down the ions and resulting in a type of delayed extraction, which can increase the resolution of the analysis (see, e.g., Juhasz et al. (1996) *Analysis. Anal. Chem.* 68:941–946, see also, e.g., U.S. Pat. Nos. 5,777,325, 5,742,049, 5,654,545, 5,641,959, 5,654,545 and 5,760,393 for descriptions of MALDI and delayed extraction protocols).

The probe through which the pins are fitted also can be of various geometries. For example, a large probe with multiple holes, one for each pin, can be fitted over the pin tool and the entire assembly is translated in the X-Y axes in the mass spectrometer. The probe also can be a fixed probe with a single hole, which is large enough to give an adequate electric field, but small enough to fit between the pins. The pin tool then is translated in all three axes, with each pin being introduced through the hole for sequential analyses. This latter format is more suitable for a higher density pin tool, for example, a pin tool based on a 384 well or higher density microplate format. These two probes are suitable for the two mass spectrometer geometries, as disclosed above.

Pin tools can be useful for immobilizing polypeptides of interest in spatially addressable manner on an array. Such spatially addressable or pre-addressable arrays are useful in a variety of processes, including, for example, quality control and amino acid sequencing diagnostics. The pin tools described in the copending applications U.S. application Ser. Nos. 08/786,988 and 08/787,639 and International PCT application No. WO 98/20166 are serial and parallel dispensing tools that can be employed to generate multi-element arrays of polypeptides on a surface of the solid support. The array surface can be flat, with beads, or geometrically altered to include wells, which can contain beads. A pin tool that allows the parallel development of a sample array is provided. Such a tool is an assembly of vesicle elements, or pins, where each of the pins can include a narrow interior chamber suitable for holding nanoliter volumes of fluid. Each of the pins fits inside a housing that has an interior chamber. The interior housing can be connected to a pressure source that can control the pressure within the interior housing chamber to regulate the flow of fluid through the interior chamber of the pins, thereby allowing for the controlled dispensing of defined volumes of fluid from the vesicles.

The pin tool also can include a jet assembly, which can include a capillary pin having an interior chamber, and a transducer element mounted to the pin and capable of driving fluid through the interior chamber of the pin to eject fluid from the pin. In this way, the tool can dispense a spot of fluid to a support surface by spraying the fluid from the pin. The transducer also can cause a drop of fluid to extend from the capillary so that fluid can be passed to the array, or other solid support, by contacting the drop to the surface of the array. The pin tool also can form an array of polypeptides by dispensing the polypeptides in a series of steps, while moving the pin to different locations above the array surface to form the sample array. The pin tool then can pass prepared polypeptide arrays to a plate assembly that disposes the arrays for analysis by mass spectrometry, which generates a set of spectra signal indicative of the composition of the polypeptides under analysis.

The pin tool can include a housing having a plurality of sides and a bottom portion having formed therein a plurality of apertures, the walls and bottom portion of the housing defining an interior volume; one or more fluid transmitting vesicles, or pins, mounted within the apertures, having a nanovolume sized fluid holding chamber for holding nanovolumes of fluid, the fluid holding chamber being disposed in fluid communication with the interior volume of the housing, and a dispensing element that is in communication with the interior volume of the housing for selectively dispensing nanovolumes of fluid form the nanovolume sized fluid transmitting vesicles when the fluid is loaded with the fluid holding chambers of the vesicles. This allows the dispensing element to dispense nanovolumes of the fluid onto the surface of the support when the apparatus is disposed over and in registration with the support.

The fluid transmitting vesicle can have an open proximal end and a distal tip portion that extends beyond the housing bottom portion when mounted within the apertures. In this way the open proximal end can dispose the fluid holding chamber in fluid communication with the interior volume when mounted with the apertures. Optionally, the plurality of fluid transmitting vesicles are removably and replaceably mounted within the apertures of the housing, or alternatively can include a glue seal for fixedly mounting the vesicles within the housing.

The fluid holding chamber also can include a narrow bore, which is dimensionally adapted for being filled with the fluid through capillary action, and can be sized to fill substantially completely with the fluid through capillary action. The plurality of fluid transmitting vesicles includes an array of fluid delivering needles, which can be formed of metal, glass, silica, polymeric material, or any other suitable material, and, thus, as disclosed herein, also can serve as a solid support.

The housing also can include a top portion, and mechanical biasing elements for mechanically biasing the plurality of fluid transmitting vesicles into sealing contact with the housing bottom portion. In addition, each fluid transmitting vesicle can have a proximal end portion that includes a flange, and further includes a seal element disposed between the flange and an inner surface of the housing bottom portion for forming a seal between the interior volume and an external environment. The biasing elements can be mechanical and can include a plurality of spring elements each of which are coupled at one end to the proximal end of each the plurality of fluid transmitting vesicles, and at another end to an inner surface of the housing top portion. The springs can apply a mechanical biasing force to the vesicle proximal end to form the seal.

The housing also can include a top portion, and a securing element for securing the housing top portion to the housing bottom portion. The securing element can include a plurality of fastener-receiving apertures formed within one of the top and bottom portions of the housing, and a plurality of fasteners for mounting within the apertures for securing together the housing top and bottom portions.

The dispensing element can include a pressure source fluidly coupled to the interior volume of the housing for disposing the interior volume at a selected pressure condition. Moreover, where the fluid transmitting vesicles are to be filled through capillary action, the dispensing element can include a pressure controller that can vary the pressure source to dispose the interior volume of the housing at varying pressure conditions. This allows the controller varying element to dispose the interior volume at a selected pressure condition sufficient to offset the capillary action to fill the fluid holding chamber of each vesicle to a predetermined height corresponding to a predetermined fluid amount. Additionally, the controller can include a fluid selection element for selectively discharging a selected nanovolume fluid amount from the chamber of each the vesicle. In addition, a pressure controller that operates under the controller of a computer program operating on a data processing system to provide variable control over the pressure applied to the interior chamber of the housing is provided.

The fluid transmitting vesicle can have a proximal end that opens onto the interior volume of the housing, and the fluid holding chamber of the vesicles are sized to substantially completely fill with the fluid through capillary action without forming a meniscus at the proximal open end. Optionally, the apparatus can have plural vesicles, where a first portion of the plural vesicles include fluid holding chambers of a first size and a second portion including fluid holding chambers of a second size, whereby plural fluid volumes can be dispensed.

The tool also can include a fluid selection element that has a pressure source coupled to the housing and in communication with the interior volume for disposing the interior volume at a selected pressure condition, and an adjustment element that couples to the pressure source for varying the pressure within the interior volume of the housing to apply a positive pressure in the fluid chamber of each the fluid transmitting vesicle to vary the amount of fluid dispensed therefrom. The selection element and adjustment element can be computer programs operating on a data processing system that directs the operation of a pressure controller connected to the interior chamber.

The pin tool apparatus can be used for dispensing a fluid containing a polypeptide of interest, particularly a target polypeptide, into one or more wells of a multi-well device, which can be a solid support. The apparatus can include a housing having a plurality of sides and a bottom portion having formed therein a plurality of apertures, the walls and bottom portion defining an interior volume, a plurality of fluid transmitting vesicles, mounted within the apertures, having a fluid holding chamber disposed in communication with the interior volume of the housing, and a fluid selection and dispensing means in communication with the interior volume of the housing for variably selecting am amount of the fluid loaded within the fluid holding chambers of the vesicles to be dispensed from a single set of the plurality of fluid transmitting vesicles. Accordingly, the dispensing means dispenses a selected amount of the fluid into the wells of the multi-well device when the apparatus is disposed over and in registration with the device.

The fluid dispensing apparatus for dispensing fluid containing a polypeptide of interest into one or more wells of a multi-well device can include a housing having a plurality of sides and top and bottom portions, the bottom portion having formed therein a plurality of apertures, the walls and top and bottom portions of the housing defining an interior volume, a plurality of fluid transmitting vesicles, mounted within the apertures, having a fluid holding chamber sized to hold nanovolumes of the fluid, the fluid holding chamber being disposed in fluid communication with the volume of the housing, and mechanical biasing element for mechanically biasing the plurality of fluid transmitting vesicles into sealing contact with the housing bottom portion.

Determining the Mass of the Polypeptide by Mass Spectrometry

The identity of an isolated target polypeptide is determined by mass spectrometry. For mass spectrometry analysis, the target polypeptide can be solubilized in an appropriate solution or reagent system. The selection of a solution or reagent system, for example, an organic or inorganic solvent, will depend on the properties of the target polypeptide and the type of mass spectrometry performed, and is based on methods well known in the art (see, for example, Vorm et al., *Anal. Chem.* 66:3281 (1994), for MALDI; Valaskovic et al., *Anal. Chem.* 67:3802 (1995), for ESI). Mass spectrometry of peptides also is described, for example, in International PCT application No. WO 93/24834 to Chait et al. and U.S. Pat. No. 5,792,664.

A solvent is selected so as to considerably reduce or fully exclude the risk that the target polypeptide will be decomposed by the energy introduced for the vaporization process. A reduced risk of target polypeptide decomposition can be achieved, for example, by embedding the sample in a matrix, which can be an organic compound such as a sugar, for example, a pentose or hexose, or a polysaccharide such as cellulose. Such compounds are decomposed thermolytically into $CO_2$ and $H_2O$ such that no residues are formed that can lead to chemical reactions. The matrix also can be an inorganic compound such as nitrate of ammonium, which is decomposed essentially without leaving any residue. Use of these and other solvents is known to those of skill in the art (see, e.g., U.S. Pat. No. 5,062,935).

Mass spectrometer formats for use in analyzing a target polypeptide include ionization (I) techniques, such as, but not limited to, matrix assisted laser desorption (MALDI), continuous or pulsed electrospray (ESI) and related methods such as ionspray or thermospray), and massive cluster impact (MCI). Such ion sources can be matched with detection formats, including linear or non-linear reflectron time-of-flight (TOF), single or multiple quadrupole, single or multiple magnetic sector, Fourier transform ion cyclotron resonance (FTICR), ion trap, and combinations thereof such as ion-trap/time-of-flight. For ionization, numerous matrix/wavelength combinations (MALDI) or solvent combinations (ESI) can be employed. Sub-attomole levels of protein have been detected, for example, using ESI mass spectrometry (Valaskovic, et al., *Science* 273:1199–1202 (1996)) and MALDI mass spectrometry (Li et al., *J. Am. Chem. Soc.* 118:1662–1663(1996)).

Electrospray mass spectrometry has been described by Fenn et al. (*J. Phys. Chem.* 88:4451–59 (1984); PCT Application No. WO 90/14148) and current applications are summarized in review articles (Smith et al., *Anal. Chem.* 62:882–89 (1990); Ardrey, *Electrospray Mass Spectrometry,*

*Spectroscopy Europe* 4:10–18 (1992)). MALDI-TOF mass spectrometry has been described by Hillenkamp et al. ("Matrix Assisted UV-Laser Desorption/Ionization: A New Approach to Mass Spectrometry of Large Biomolecules, Biological Mass Spectrometry" (Burlingame and McCloskey, eds., Elsevier Science Publ. 1990), pp. 49–60). With ESI, the determination of molecular weights in femtomole amounts of sample is very accurate due to the presence of multiple ion peaks, all of which can be used for mass calculation.

The mass of a target polypeptide determined by mass spectrometry can be compared to the mass of a corresponding known polypeptide. For example, where the target polypeptide is a mutant protein, the corresponding known polypeptide can be the corresponding normal protein. Similarly, where the target polypeptide is suspected of being translated from a gene having an abnormally high number of trinucleotide repeats, the corresponding known polypeptide can be the corresponding protein having a wild type number of repeats, if any. Where the target polypeptide contains a number of repeated amino acids directly correlated to the number of trinucleotide repeats transcribed and translated from DNA, the number of repeated trinucleotide repeats in the DNA encoding the polypeptide can be deduced from the mass of the polypeptide. If desired, a target polypeptide can be conditioned prior to mass spectrometry, as disclosed herein, thus facilitating identification of the polypeptide.

MALDI

Matrix assisted laser desorption (MALDI) is preferred among the mass spectrometric methods herein. Methods for performing MALDI are well known to those of skill in the art (see, e.g., ). Numerous methods for improving resolution are also known. For example, resolution in MALDI TOF mass spectrometry can be improved by reducing the number of high energy collisions during ion extraction (see, e.g., Juhasz et al. (1996) *Analysis. Anal. Chem.* 68:941–946, see also, e.g., U.S. Pat. No. 5,777,325, 5,742,049, 5,654,545, 5,641,959, 5,654,545, 5,760,393 and 5,760,393 for descriptions of MALDI and delayed extraction protocols).

Amino Acid Sequencing of Target Polypeptides

A process of determining the identity of a target polypeptide using mass spectrometry, as disclosed herein, can be performed by determining the amino acid sequence, or a portion thereof, of a target polypeptide. Amino acid sequencing can be performed, for example, from the carboxyl terminus using carboxypeptidase such as carboxypeptidase Y, carboxypeptidase P, carboxypeptidase A, carboxypeptidase G or carboxypeptidase B, or other enzyme that progressively digests a polypeptide from its carboxyl terminus; or from the N-terminus of the target polypeptide by using the Edman degradation method or using an aminopeptidase such as alanine aminopeptidase, leucine aminopeptidase, pyroglutamate peptidase, dipeptidyl peptidase, microsomal peptidase, or other enzyme that progressively digests a polypeptide from its amino terminus. If desired, the target polypeptide first can be cleaved into peptide fragments using an enzyme such as trypsin, chymotrypsin, Asp-N, thrombin or or other suitable enzyme. The fragments then can be isolated and subjected to amino acid sequencing by mass spectrometry, or a nested set of deletion fragments of the polypeptide can be prepared by incubating the polypeptide for various periods of time in the presence of an aminopeptidase or a carboxypeptidase and, if desired, in the presence of reagents that modify the activity of a peptidase on the polypeptide (see, for example, U.S. Pat. No. 5,792,664; International Publ. No. WO 96/36732). If desired, a tag, for example, a tag peptide, can be conjugated to a fragment of a target polypeptide. Such a conjugation can be performed prior to or following cleavage of the target polypeptide.

Amino acid sequencing of a target polypeptide can be performed either on the free polypeptide or after immobilizing the polypeptide on a solid support. A target polypeptide can be immobilized on a solid support, for example, by linking the polypeptide to the support through its amino terminus or its carboxyl terminus or directly or via a linker or linkers by methods known to those of skill in the art or as described herein, then treating the immobilized polypeptide with an exopeptidase specific for the unbound terminus. For example, where a target polypeptide is linked to a solid support through its amino terminus, the immobilized polypeptide can be treated with a carboxypeptidase, which sequentially degrades the polypeptide from its carboxyl terminus. Alternatively, where the target polypeptide is linked to a solid support through its carboxyl terminus, the polypeptide can be digested from its amino terminus using, for example, Edman's reagent.

For amino acid sequencing, the target polypeptide is treated with the protease in a time-limited manner, and released amino acids are identified by mass spectrometry. If desired, degradation of a target polypeptide can be performed in a reactor apparatus (see International Publ. No. WO 94/21822, published Sep. 29, 1994), in which the polypeptide can be free in solution and the protease can be immobilized, or in which the protease can be free in solution and the polypeptide can be immobilized. At time intervals or as a continuous stream, the reaction mixture containing a released amino acid is transported to a mass spectrometer for analysis. Prior to mass spectrometric analysis, the released amino acids can be transported to a reaction vessel for conditioning, which can be by mass modification. The determination of the amino acid sequence of the target polypeptide, particularly the identification of an allelic variation in the target polypeptide as compared to a corresponding known polypeptide, can be useful, for example, to determine whether the subject from which the target polypeptide was obtained has or is predisposed to a particular disease or condition.

If desired, the target polypeptide can be conditioned, for example, by mass modified prior to sequencing. It should be recognized, however, that mass modification of a polypeptide prior to chemical or enzymatic degradation, for example, can influence the rate or extent of degradation. Accordingly, the skilled artisan will know that the influence of conditioning and mass modification on polypeptide degradation should be characterized prior to initiating amino acid sequencing.

A process as disclosed herein is conveniently performed in a multiplexing format, thereby allowing a determination of the identities of a plurality of two or more target polypeptides in a single procedure. For multiplexing, a population of target polypeptides can be synthesized by in vitro translation, where each of the target nucleic acids encoding each of the target polypeptides is translated, in a separate reaction, in the presence of one or more mass modifying amino acids. The population of target polypeptides can be encoded, for example, by target nucleic acids representing the different polymorphic regions of a particular gene. Each of the individual reactions can be performed using one or more amino acids that are differentially mass modified, for example, differentially mass modified, particularly using basic residues. Following translation, each target polypeptide is distinguishable by the particular mass modified amino acid.

A plurality of target polypeptides also can be obtained, for example, from naturally occurring proteins and examined by multiplexing, provided that each of the plurality of target polypeptides is differentially mass modified. For example, where a plurality of target polypeptides are being examined to determine whether a particular polypeptide is an allelic variant containing either a Gly residue or an Ala residue, the Gly and Ala residues in each polypeptide in the plurality can be mass modified with a mass label specific for that polypeptide. Identification of a Gly or Ala residue having a particular mass can be used to determine the particular polypeptide and the nature of the polymorphism.

Amino acid modifications can be effected during or after in vitro translation of the target polypeptide. For example, any amino acid with a functional group on a side chain can be derivatized using methods known to those of skill in the art. For example, N-succinimdyl-3(2-pyridyldithio) propionate (SPDP) can be used to introduce sulfhydryl groups on lysine residues, thereby altering the mass of the polypeptide compared to the untreated polypeptide.

Identifying the Polypeptide by Comparing the Mass of Target Polypeptide to a Known Polypeptide In methods other than those in which the polypeptide is sequenced and thereby identified, identification of the polypeptide is effected by comparison with a reference (or known) polypeptide. The result indicative of identity is a function of the selected reference polypeptide. The reference polypeptide can be selected so that the target polypeptide will either have a mass substantially identical (identical within experimental error) to the reference polypeptide, or will have a mass that is different from the reference polypeptide.

For example, if the reference polypeptide is encoded by a wild type allele of a gene that serves as a genetic marker, and the method is for screening for the presence of a disease or condition that is indicated by a mutation in that allele, then presence of the mutation will be identified by observing a difference between the mass of the target polypeptide and reference polypeptide. Observation of such difference thereby "identifies" the polypeptide and indicates the presence of the marker for the disease or condition. This result will indicate the presence of a mutation.

Alternatively, if the reference polypeptide is encoded by a mutant allele of a gene that serves as a genetic marker, and the method is for screening for the presence of a disease or condition that is indicated by a mutation in that allele, then presence of the mutation will be identified by observing no difference between the mass of the target polypeptide and reference polypeptide. Observation of no difference thereby "identifies" the polypeptide and indicates the presence of the marker for the disease or condition. Furthermore, this result can provide information about the specific mutation.

Identifying a Target Polypeptide Based on Peptide Fragments of the Target Polypeptide A process as disclosed herein also provides a means for determining the identity of a target polypeptide by comparing the masses of defined peptide fragments of the target polypeptide with the masses of corresponding peptide fragments of a known polypeptide. Such a process can be performed, for example, by obtaining the target polypeptide by in vitro translation, or by in vitro transcription followed by translation, of a nucleic acid encoding the target polypeptide; contacting the target polypeptide with at least one agent that cleaves at least one peptide bond in the target polypeptide, for example, an endopeptidase such as trypsin or a chemical cleaving agent such as cyanogen bromide, to produce peptide fragments of the target polypeptide; determining the molecular mass of at least one of the peptide fragments of the target polypeptide by mass spectrometry; and comparing the molecular mass of the peptide fragments of the target polypeptide with the molecular mass of peptide fragments of a corresponding known polypeptide. The masses of the peptide fragments of a corresponding known polypeptide either can be determined in a parallel reaction with the target polypeptide, wherein the corresponding known polypeptide also is contacted with the agent; can be compared with known masses for peptide fragments of a corresponding known polypeptide contacted with the particular cleaving agent; or can be obtained from a database of polypeptide sequence information using algorithms that determine the molecular mass of peptide fragment of a polypeptide.

The disclosed process of determining the identity of a target polypeptide by performing mass spectrometry on defined peptide fragments of the target polypeptide is particularly adaptable to a multiplexing format. Accordingly, a process is provided for determining the identity of each target polypeptide in a plurality of target polypeptides, by obtaining the plurality of target polypeptides; contacting each target polypeptide with at least one agent that cleaves at least one peptide bond in each target polypeptide to produce peptide fragments of each target polypeptide; determining the molecular mass of at least one of the peptide fragments of each target polypeptide in the plurality by mass spectrometry; and comparing the molecular mass of the peptide fragments of each target polypeptide with the molecular mass of peptide fragments of a corresponding known polypeptide.

In performing a process as disclosed, it can be desirable to condition the target polypeptides. The polypeptides can be conditioned prior to cleavage, or the peptide fragments of the target polypeptide that will be examined by mass spectrometry can be conditioned prior to mass spectrometry. It also can be desirable to mass modify the target polypeptide, particularly to differentially mass modify each target polypeptide where a plurality of target polypeptides is being examined in a multiplexing format. Mass modification can be performed either on each polypeptide prior to contacting the polypeptide with the cleaving agent, or on the peptide fragments of the polypeptide that will examined by mass spectrometry.

A target polypeptide, particularly each target polypeptide in a plurality of target polypeptides, can be immobilized to a solid support prior to conditioning or mass modifying the polypeptide, or prior to contacting the polypeptide with a cleaving agent. In particular, the solid support can be a flat surface, or a surface with a structure such as wells, such that each of the target polypeptides in the plurality can be positioned in an array, each at a particular address. In general, a target polypeptide is immobilized to the solid support through a cleavable linker such as an acid labile linker, a chemically cleavable linker or a photocleavable linker. Following treatment of the target polypeptide, the released peptide fragments can be analyzed by mass spectrometry, or the released peptide fragments can be washed from the reaction and the remaining immobilized peptide fragment can be released, for example, by chemical cleavage or photocleavage, as appropriate, and can be analyzed by mass spectrometry.

It also can be useful to immobilize a particular target polypeptide to the support through both the amino terminus and the carboxyl terminus using, for example, a chemically cleavable linker at one terminus and a photocleavable linker at the other end. In this way, the target polypeptides, which can be immobilized, for example, in an array in wells, can be contacted with one or more agents that cleave at least one peptide bond in the polypeptides, the internal peptide fragments then can be washed from the wells, along with the agent and any reagents in the well, leaving one peptide fragment of the target polypeptide immobilized to the solid support through the chemically cleavable linker and a second peptide fragment, from the opposite end of the target polypeptide, immobilized through the photocleavable linker. Each peptide fragment then can be analyzed by mass spectrometry following sequential cleavage of the fragments, for example, after first cleaving the chemically cleavable linker, then cleaving the photocleavable linker. Such a method provides a means of analyzing both termini of a polypeptide, thereby facilitating identification of the target polypeptide. It should be recognized that immobilization of a target polypeptide at both termini can be performed by modifying both ends of a target polypeptide, one terminus being modified to allow formation of a chemically cleavable linkage with the solid support and the other terminus being modified to allow formation of a photocleavable linkage with the solid support. Alternatively, the target polypeptides can be split into two portions, one portion being modified at one terminus allow formation, for example, of a chemically cleavable linkage, and the second portion being modified at the other terminus to allow formation, for example, of a photocleavable linkage. The two populations of modified target polypeptides then can be immobilized, together, on a solid support containing the appropriate functional groups for completing immobilization.

Exemplary Uses

Methods for determining the identity of a target polypeptide are disclosed herein. The identity of the target polypeptide allows information to be obtained regarding the DNA sequence encoding the target polypeptide. The target polypeptide can be from a eukaryote such as a vertebrate, particularly a mammal such as a human, or can be from a prokaryote, including a bacterium or a virus. Generally, the target polypeptide can be from any organism, including a plant.

A target polypeptide can be immobilized to a solid support, thereby facilitating manipulation of the polypeptide prior to mass spectrometry. For example, a target polypeptide can be translated in vitro. Such a method of obtaining a target polypeptide conveniently allows attachment of a tag to the polypeptide, for example, by producing a fusion polypeptide of the target polypeptide and a tag peptides such as a polyhistidine tag. The presence of a tag peptide such as a polyhistidine tag provides a means to isolate the target polypeptide, for example, from the in vitro translation reaction, by passing the mixture over a nickel chelate column, since nickel ions interact specifically with a polyhistidine sequence. The target polypeptide then can be captured by conjugation to a solid support, thereby immobilizing the target polypeptide. If general, conjugation of the polypeptide to the solid support can be mediated through a linker, which provides desirable characteristics such as being readily cleavable, for example, chemically cleavable, heat cleavable or photocleavable. As shown in FIG. 2, for example, the target polypeptide can be immobilized at its amino terminus to a solid support through a diisopropylsilyl linker, which readily is cleavable under acidic conditions such as when exposed to the mass spectrometry matrix solution 3-HPA. For example, the solid support, or a linker conjugated to the support or a group attached to such a linker, can be in the activated carboxy form such as a sulfo-NHS ester, which facilitates conjugation of the polypeptide through its amino terminus. Furthermore, conjugation of a polypeptide to a solid support can be facilitated by engineering the polypeptide to contain, for example, a string of lysine residues, which increases the concentration of amino groups available to react with an activated carboxyl support. Of course, a polypeptide also can be conjugated through its carboxyl terminus using a modified form of the linker shown in FIG. 2 (see FIG. 3), or can be conjugated using other linkers as disclosed herein or otherwise known in the art. The immobilized target polypeptide then can be manipulated, for example, by proteolytic cleavage using an endopeptidase or a chemical reagent such as cyanogen bromide, by sequential truncation from its free end using an exopeptidase or a chemical reagent such as Edman's reagent, or by conditioning in preparation for mass spectrometric analysis, for example, by cation exchange to improve mass spectrometric analysis. An advantage of performing such manipulations with an immobilized polypeptide is that the reagents and undesirable reaction products can be washed from the remaining immobilized polypeptide, which then can be cleaved from the solid support in a separate reaction or can be subjected to mass spectrometry, particularly MALDI-TOF, under conditions that cleave the polypeptide from the support, for example, exposure of a polypeptide linked to the support through a photocleavable linker to the MALDI laser.

For purposes of the conjugation reactions, as well as enzymatic reactions, it is assumed that the termini of a target polypeptide are more reactive than the amino acid side groups due, for example, to steric considerations. However, it is recognized that amino acid side groups can be more reactive than the relevant terminus, in which case the artisan would know that the side group should be blocked prior to performing the reaction of interest. Methods for blocking an amino acid side group are well known and blocked amino acid residues are readily available and used, for example, for chemical synthesis of peptides. Similarly, it is recognized that a terminus of interest of the polypeptide can be blocked due, for example, to a post-translational modification, or can be buried within a polypeptide due to secondary or tertiary conformation. Accordingly, the artisan will recognize that a blocked amino terminus of a polypeptide, for example, must be made reactive either by cleaving the amino terminal amino acid or by deblocking the amino acid. In addition, where the terminus of interest is buried within the polypeptide structure, the artisan will know that the polypeptide, in solution, can be heated to about 70 to 100° C. prior to performing a reaction. It is recognized, for example, that when the reaction to be performed is an enzymatic cleavage, the enzymes selected should be stable at elevated temperatures. Such temperature stable enzymes, for example, thermostable peptidases, including carboxypeptidases and aminopeptidases, are obtained from thermophilic organisms and are commercially available. In addition, where it is desirable not to use heat to expose an otherwise buried terminus of a polypeptide, altering the salt conditions can provide a means to expose the terminus. For example, a polypeptide terminus can be exposed using conditions of high ionic strength, in which case an enzyme such as an exopeptidase is selected based on its tolerance to high ionic strength conditions.

Depending on the target polypeptide to be detected, the disclosed methods allow the diagnosis, for example, of a genetic disease or chromosomal abnormality; a predisposition to or an early indication of a gene influenced disease or condition such as obesity, atherosclerosis, diabetes or cancer; or an infection by a pathogenic organism, including a virus, bacterium, parasite or fungus; or to provide information relating to identity or heredity based, for example, on an analysis of mini-satellites and micro-satellites, or to compatibility based, for example, on HLA phenotyping.

A process is provided herein for detecting genetic lesions that are characterized by an abnormal number of trinucleotide repeats, which can range from less than 10 to more than 100 additional trinucleotide repeats relative to the number of repeats, if any, in a gene in a non-affected individual. Diseases associated with such genetic lesions include, for example, Huntington's disease, prostate cancer, SCA-1, Fragile X syndrome (Kremer et al., *Science* 252:1711–14 (1991); Fu et al., *Cell* 67:1047–58 (1991); Hirst et al., *J. Med. Genet.* 28:824–29 (1991), myotonic dystrophy type I (Mahadevan et al., *Science* 255:1253–55 (1992); Brook et al., *Cell* 68:799–808 (1992)), Kennedy's disease (also termed spinal and bulbar muscular atrophy; La Spada et al., *Nature* 352:77079 (1991)); Machado-Joseph disease, and dentatorubral and pallidolyusian atrophy. The abnormal number of triplet repeats can be located in any region of a gene, including a coding region, a non-coding region of an exon, an intron, or a promoter or other regulatory element. For example, the expanded trinucleotide repeat associated with myotonic dystrophy occurs in the 3' untranslated region (UTR) of the MtPK gene on chromosome 19. In some of these diseases, for example, prostate cancer, the number of trinucleotide repeats is positively correlated with prognosis of the disease such that a higher number of trinucleotide repeats correlates with a poorer prognosis.

A process for determining the identity of an allelic variant of a polymorphic region of a gene, particularly a human gene, also is provided. Allelic variants can differ in the identity of a single nucleotide or base pair, for example, by substitution of one nucleotide; in two or more nucleotides or base pairs; or in the number of nucleotides due, for example, to additions or deletions of nucleotides or of trinucleotide repeats; or due to chromosomal rearrangements such as translocations. Specific allelic variants of polymorphic regions are associated with specific diseases and, in some cases, correlate with the prognosis of the disease. A specific allelic variant of a polymorphic region associated with a disease is referred to herein as a "mutant allelic variant" and is considered to be a "genetic lesion."

Also provided is a process for determining the genetic nature of a phenotype or for identifying a predisposition to that phenotype. For example, it can be determined whether a subject has a predisposition to a specific disease or condition, i.e., whether the subject has, or is at risk of developing, a disease or condition associated with a specific allelic variant of a polymorphic region of a gene. Such a subject can be identified by determining whether the subject carries an allelic variant associated with the specific disease or condition. Furthermore, if the disease is a recessive disease it can be determined whether a subject is a carrier of a recessive allele of a gene associated with the specific disease or condition.

Numerous diseases or conditions have been genetically linked to a specific gene and, more particularly, to a specific mutation or genetic lesion of a gene. For example, hyperproliferative diseases such as cancers are associated with mutations in specific genes. Such cancers include breast cancer, which has been linked to mutations in BRCA1 or BRCA2. Mutant alleles of BRCA1 are described, for example, in U.S. Pat. No. 5,622,829. Other genes such as tumor suppressor genes, which are associated with the development of cancer when mutated, include, but are not limited to, p53 (associated with many forms of cancer); Rb (retinoblastoma); WT1 (Wilm's tumor) and various proto-oncogenes such as c-myc and c-fos (see Thompson and Thompson, "Genetics in Medicine" 5th Ed.; Nora et al., "Medical Genetics" 4th Ed. (Lea and Febiger, eds.).

A process as disclosed herein also can be used to detect DNA mutations that result in the translation of a truncated polypeptide, as occurs, for example, with BRCA1 and BRCA2. Translation of nucleic acid regions containing such a mutation results in a truncated polypeptide that easily can be differentiated from the corresponding non-truncated polypeptide by mass spectrometry.

A process as disclosed herein also can be used to genotype a subject, for example, a subject being considered as a recipient or a donor of an organ or a bone marrow graft. For example, the identity of MHC alleles, particularly HLA alleles, in a subject can be determined. The information obtained using such a method is useful because transplantation of a graft to a recipient having different transplantation antigens than the graft can result in rejection of the graft and can result in graft versus host disease following bone marrow transplantation.

The response of a subject to medicaments can be affected by variations in drug modification systems such as the cytochrome P450 system, and susceptibility to particular infectious diseases can be influenced by genetic status. Thus, the identification of particular allelic variants can be used to predict the potential responsiveness of a subject to specific drug or the susceptibility of a subject to an infectious disease. Genes involved in pharmacogenetics are known (see, e.g., Nora et al., "Medical Genetics" 4th Ed. (Lea and Febiger, eds.).

Some polymorphic regions may not be related to any disease or condition. For example, many loci in the human genome contain a polymorphic short tandem repeat (STR) region. STR loci contain short, repetitive sequence elements of 3 to 7 base pairs in length. It is estimated that there are 200,000 expected trimeric and tetrameric STRs, which are present as frequently as once every 15 kb in the human genome (see, e.g., International PCT application No. WO 9213969 A1, Edwards et al., *Nucl. Acids Res.* 19:4791 (1991); Beckmann et al. (1992) *Genomics* 12:627–631). Nearly half of these STR loci are polymorphic, providing a rich source of genetic markers. Variation in the number of repeat units at a particular locus is responsible for the observed polymorphism reminiscent of variable nucleotide tandem repeat (VNTR) loci (Nakamura et al. (1987) *Science* 235:1616–1622); and minisatellite loci (Jeffreys et al. (1985) *Nature* 314:67–73), which contain longer repeat units, and microsatellite or dinucleotide repeat loci (Luty et al. (1991) *Nucleic Acids Res.* 19:4308; Litt et al. (1990) *Nucleic Acids Res.* 18:4301; Litt et al. (1990) *Nucleic Acids Res.* 18:5921; Luty et al. (1990) *Am. J. Hum. Genet.* 46:776–783; Tautz (1989) *Nucl. Acids Res.* 17:6463–6471; Weber et al. (1989) *Am. J. Hum. Genet.* 44:388–396; Beckmann et al. (1992) *Genomics* 12:627–631).

Polymorphic STR loci and other polymorphic regions of genes are extremely useful markers for human identification, paternity and maternity testing, genetic mapping, immigration and inheritance disputes, zygosity testing in twins, tests for inbreeding in humans, quality control of human cultured cells, identification of human remains, and testing of semen samples, blood stains and other material in forensic medicine. Such loci also are useful markers in commercial animal breeding and pedigree analysis and in commercial plant breeding. Traits of economic importance in plant crops and animals can be identified through linkage analysis using polymorphic DNA markers. Efficient processes for determining the identity of such loci are disclosed herein.

STR loci can be amplified by PCR using specific primer sequences identified in the regions flanking the tandem repeat to be targeted. Allelic forms of these loci are differentiated by the number of copies of the repeat sequence contained within the amplified region. Examples of STR loci include but are not limited to pentanucleotide repeats in the human CD4 locus (Edwards et al., *Nucl. Acids Res.* 19:4791 (1991)); tetranucleotide repeats in the human aromatase cytochrome P-450 gene (CYP19; Polymeropoulos et al., *Nucl. Acids Res.* 19:195 (1991)); tetranucleotide repeats in the human coagulation factor XIII A subunit gene (F13A1; Polymeropoulos et al., *Nucl. Acids Res.* 19:4306 (1991)); tetranucleotide repeats in the F13B locus (Nishimura et al., *Nucl. Acids Res.* 20:1167 (1992)); tetranucleotide repeats in the human c-les/fps, proto-oncogene (FES; Polymeropoulos et al., *Nucl. Acids Res.* 19:4018 (1991)); tetranucleotide repeats in the LFL gene (Zuliani et al., *Nucl. Acids Res.* 18:4958 (1990)); trinucleotide repeats polymorphism at the human pancreatic phospholipase A-2 gene (PLA2; Polymeropoulos et al., *Nucl. Acids Res.* 18:7468 (1990)); tetranucleotide repeats polymorphism in the VWF gene (Ploos et al., *Nucl. Acids Res.* 18:4957 (1990)); and tetranucleotide repeats in the human thyroid peroxidase (hTPO) locus (Anker et al, *Hum. Mol. Genet.* 1:137 (1992)).

A target DNA sequence can be part of a foreign genetic sequence such as the genome of an invading microorganism, including, for example, bacteria and their phages, viruses, fungi, protozoa, and the like. The processes provided herein are particularly applicable for distinguishing between different variants or strains of a microorganism in order, for example, to choose an appropriate therapeutic intervention. Examples of disease-causing viruses that infect humans and animals and that can be detected by a disclosed process include but are not limited to Retroviridae (e.g., human immunodeficiency viruses such as HIV-1 (also referred to as HTLV-III, LAV or HTLV-III/LAV; Ratner et al., *Nature*, 313:227–284 (1985); Wain Hobson et al, *Cell*, 40:9–17 (1985), HIV-2 (Guyader et al., *Nature*, 328:662–669 (1987); European Patent Publication No. 0 269 520; Chakrabarti et al., *Nature*, 328:543–547 (1987); European Patent Application No. 0 655 501), and other isolates such as HIV-LP (International Publication No. WO 94/00562); Picornaviridae (e.g., polioviruses, hepatitis A virus, (Gust et al., Intervirology, 20:1–7 (1983)); enteroviruses, human coxsackie viruses, rhinoviruses, echoviruses); Calcivirdae (e.g. strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Papovaviridae; Hepadnaviridae (Hepatitis B virus); Parvoviridae (most adenoviruses); Papovaviridae (papilloma viruses, polyoma viruses); Adenoviridae (most adenoviruses); Herpesviridae (herpes simplex virus type 1 (HSV-1) and HSV-2, varicella zoster virus, cytomegalovirus, herpes viruses; Poxviridae (variola viruses, vaccinia viruses, pox viruses); Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted, i.e., Hepatitis C); Norwalk and related viruses, and astroviruses.

Examples of infectious bacteria include but are not limited to *Helicobacter pyloris, Borelia burgdorferi, Legionella pneumophilia,* Mycobacteria sp. (e.g. *M. tuberculosis, M. avium, M. intracellulare, M. kansaii, M. gordonae*), *Staphylococcus aureus, Neisseria gonorrheae, Neisseria meningitidis, Listeria monocytogenes, Streptococcus pyogenes* (Group A Streptococcus), *Streptococcus agalactiae* (Group B Streptococcus), Streptococcus sp. (viridans group), *Streptococcus faecalis, Streptococcus bovis,* Streptococcus sp. (anaerobic species), *Streptococcus pneumoniae,* pathogenic Campylobacter sp., Enterococcus sp., *Haemophilus influenzae, Bacillus antracis, Corynebacterium diphtheriae,* Corynebacterium sp., *Erysipelothrix rhusiopathiae, Clostridium perfringens, Clostridium tetani, Enterobacter aerogenes, Klebsiella pneumoniae, Pasturella multocida,* Bacteroides sp., *Fusobacterium nucleatum, Streptobacillus moniliformis, Treponema pallidium, Treponema pertenue,* Leptospira, and *Actinomyces israelli.*

Examples of infectious fungi include but are not limited to *Cryptococcus neoformans, Histoplasma capsulatum, Coccidioides immitis, Blastomyces dermatitidis, Chlamydia trachomatis, Candida albicans.* Other infectious organisms include protists such as *Plasmodium falciparum* and *Toxoplasma gondii.*

The processes and kits provide herein are further illustrated by the following examples, which should not be construed as limiting in any way. The contents of all cited references including literature references, issued patents, published patent applications as cited throughout this application are hereby expressly incorporated by reference. The practice of the processes will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *DNA Cloning,* Volumes I and II (D. N. Glover ed., 1985); *Oligonucleotide Synthesis* (M. J. Gait ed., 1984); Mullis et al. U.S. Pat. No. : 4,683,194; *Nucleic Acid Hybridization* (B. D. Hames & S. J. Higgins eds. 1984); *Transcription and Translation* (B. D. Hames & S. J. Higgins eds. 1984); *Culture of Animal Cells* (R. I. Freshney, Alan R. Liss, Inc., 1987); *Immobilized Cells and Enzymes* (IRL Press, 1986); B. Perbal, *A Practical Guide to Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo* (Cold Spring Harbor Laboratory press, Cold Spring Harbor, N.Y., 1986).

The following examples are included for illustrative purposes only and are not intended to limit the scope of the invention.

EXAMPLE 1

This example demonstrates that genomic DNA obtained from patients with spinal cerebellar ataxia 1 (SCA-1) can be used to identify target polypeptides encoded by trinucleotide repeats associated with SCA-1.

Genomic DNA Amplification

Human genomic DNA was extracted using the QIAMP Blood Kit (Qiagen), following the manufacturer's protocol. A region of the extracted DNA containing the (CAG) repeat associated with SCA-1 was amplified by PCR using primers modified to contain a transcription promoter sequence and a region coding for a His-6 tag peptide. The forward primer had the following nucleotide sequence, in which the T7 promoter sequence is italicized and the bases on the 5'-side of the promoter are random:

5'-d(GAC TTT ACT TGT ACG TGC ATA ATA CGA CTC ACT ATA GGG AGA CTG ACC ATG GGC AGT CTG AGC CA) (SEQ ID NO: 6).

The reverse primer had the following nucleotide sequence, in which the nucleotide sequence encoding the His-6 tag peptide is represented in bold and the first six 5'-bases are random:

5'-d(TGA TTC TCA ATG ATG ATG ATG ATG ATG AAC TTG AAA TGT GGA CGT AC) (SEQ ID NO: 7).

Total reaction volume was 50 μl with 20 pmol primers per reaction. Taq polymerase including 10× buffer was obtained from Boehringer Mannheim and dNTPs were obtained from Pharmacia. Cycling conditions included 5 min at 94° C., followed by 35 cycles of 30 sec at 94° C., 45 sec at 53° C., 30 sec at 72° C., with a final extension time of 2 min at 72° C. PCR products were purified using the Qiagen QUIAQUICK kit and elution of the purified products was performed using 50 μL 10 mM Tris-HCl buffer (pH 8).

Coupled in vitro Transcription and Translation

Coupled transcription and translation was performed using the TNT reaction buffer (Promega). Reaction components, in a total volume of 50 μl, were thawed and mixed according to the manufacturer's protocol, using 1 μl of T7 RNA polymerase and 1 pmol of amplified DNA, except that unlabeled methionine was used in place of $^{35}$S-methionine. The reaction mixture was incubated at 30° C. for 90 min.

Target Polypeptide Purification

The translated His-6 tagged polypeptide was purified from the wheat germ extract mixture using the Qiagen QIAEXPRESS Ni-NTA protein purification system according to the manufacturer's protocol. Briefly, the extract mixture was washed by centrifugation through a spin column containing a nickel-nitriloacetic acid resin, which affinity captures the His-6 peptide tag on the polypeptide. The polypeptide was eluted from the column with 100 mM imidazole.

Mass Spectrometry

The translated polypeptide was mixed with matrix either directly from the elution solution or first was lyophilized and resuspended in 5 μl H$_2$O. This solution was mixed 1:1 (v:v) with matrix solution (concentrated sinnapinic acid in 50/50 v:v ethanol/H$_2$O), and 0.5 μl of the mixture was added to a sample probe for analysis in a linear time-of-flight mass spectrometer operated in delayed ion extraction mode with a source potential of 25 kV. Internal calibration was achieved for all spectra using three intense matrix ion signals.

Results

Genomic DNA was obtained from 4 patients having SCA-1, as described above. Three of the patients had 10, 15, or 16 CAG repeats and the fourth patient had an unknown number of trinucleotide repeats.

A region containing the trinucleotide repeats was PCR amplified using primers (SEQ ID NOS: 6 and 7) that hybridized to sequences located on either side of the repeats. The nucleotide sequence (SEQ ID NO: 8) of a PCR product amplified from a region containing 10 CAG repeats is shown in FIG. 1A and the amino acid sequence (SEQ ID NO: 8) of a polypeptide encoded by the amplified nucleic acid is shown in FIG. 1B (SEQ ID NO. 9).

The amplified DNA from each patient was subjected to in vitro transcription and translation, and the target polypeptides were isolated on a nickel chromatography column. Mass spectrometric analysis of the peptides encoded by target polypeptides encoded by the 10, 15, and 16 CAG repeats indicated that these peptides had a molecular mass of 8238.8, 8865.4, and 8993.6 Daltons, respectively. The polypeptide encoded by the nucleic acid from the fourth patient, having an unknown number of trinucleotide repeats, had a molecular weight of 8224.8 Da. While this value does not correspond exactly with a unit number of repeats (10 is the closest), it is consistent with detection of a point mutation; i.e., the −14 Dalton shift for this polypeptide corresponds to an Ala->Gly mutation due to a C->G mutation in one of the repeats. This result demonstrates that the disclosed process allows the identification of a target polypeptide encoded by a genetic lesion associated with a disease. In addition, the results demonstrate that such a process allows the detection of a single base difference between two nucleic acids.

Detection of such subtle differences in the protein lengths are not reproducibly obtained with electrophoretic methods even with use of multiple internal standards. Even low performance MS instrumentation is capable of far better than 0.1% mass accuracy in this mass range using internal calibration; higher performance instrumentation such as Fourier transform MS is capable of ppm mass accuracy with internal or external calibration. It is should be noted that the mass difference between the 15 and 16 repeat unit polypeptides is 1.4% and the 14 Dalton mass shift due to the point mutation between the 10 repeat patients is 0.17%. Clearly, each of these situations can be routinely analyzed successfully.

EXAMPLE 2

1-(2-Nitro-5-(3-O-4,4'-dimethoxytritylpropoxy) phenyl)-1-O-((2-cyanoethoxy)-diisopropylaminophosphino)ethane A. 2-Nitro-5-(3-hydroxypropoxy)benzaldehyde 3-Bromo-1-propanol (3.34 g, 24 mmol) was refluxed in 80 ml of anhydrous acetonitrile with 5-hydroxy-2-nitrobenzaldehyde (3.34 g, 20 mmol), K$_2$CO$_3$ (3.5 g), and KI (100 mg) overnight (15 hr). The reaction mixture was cooled to room temperature and 150 ml of methylene chloride was added. The mixture was filtered and the solid residue was washed with methylene chloride. The combined organic solution was evaporated to dryness and redissolved in 100 ml methylene chloride. The resulted solution was washed with saturated NaCl solution and dried over sodium sulfate. 4.31 g (96%) of desired product was obtained after removal of the solvent in vacuo.

R$_f$=0.33 (dichloromethane/methanol, 95/5).

UV (methanol) maximum: 313, 240 (shoulder), 215 nm; minimum: 266 nm.

$^1$H NMR (DMSO-d$_6$) δ10.28 (s, 1H), 8.17 (d, 1H), 7.35 (d, 1H), 7.22 (s, 1H), 4.22(t, 2H), 3.54 (t, 2H), 1.90 (m, 2H).

$^{13}$C NMR (DMSO-d$_6$) δ189.9, 153.0, 141.6, 134.3, 127.3, 118.4, 114.0, 66.2, 56.9, 31.7.

B. 2-Nitro-5-(3-O-t-butyldimethylsilylpropoxy)benzaldehyde

2-Nitro-5-(3-hydroxypropoxy)benzaldehyde(1 g, 4.44 mmol) was dissolved in 50 ml anhydrous acetonitrile. To this solution was added 1 ml of triethylamine, 200 mg of imidazole, and 0.8 g (5.3 mmol) of tBDMSCI. The mixture was stirred at room temperature for 4 hr. Methanol (1 ml) was added to stop the reaction. The solvent was removed in vacuo and the solid residue was redissolved in 100 ml methylene chloride. The resulting solution was washed with saturated sodium bicarbonate solution and then water. The organic phase was dried over sodium sulfate and the solvent was removed in vacuo. The crude mixture was subjected to a quick silica gel column with methylene chloride to yield 1.44 g (96%) of 2-nitro-5-(3-O-t-butyl dimethylsilylpropoxy)benzaldehyde.

$R_f$=0.67 (hexane/ethyl acetate, 5/1).

UV (methanol), maximum: 317, 243, 215 nm; minimum: 235, 267 nm.

$^1$H NMR (DMSO-$d_6$) δ10.28 (s, 1H), 8.14 (d, 1H), 7.32 (d, 1H), 7.20 (s, 1H), 4.20 (t, 2H), 3.75 (t, 2H), 1.90 (m, 2H), 0.85 (s, 9H), 0.02 (s, 6H).

$^{13}$C NMR (DMSO-$d_6$) δ189.6, 162.7, 141.5, 134.0, 127.1, 118.2, 113.8, 65.4, 58.5, 31.2, 25.5, −3.1, −5.7.

C. 1-(2-Nitro-5-(3-O-t-butyldimethylsilylpropoxy)phenyl)ethanol

High vacuum dried 2-nitro-5-(3-O-t-butyldimethylsilylpropoxy)benzaldehyde (1.02 g, 3 mmol) was dissolved 50 ml of anhydrous methylene chloride. 2 M trimethylaluminium in toluene (3 ml) was added dropwise within 10 min and keeped the reaction mixture at room temperature. It was stirred further for 10 min and the mixture was poured into 10 ml ice cooled water. The emulsion was separated from water phase and dried over 100 g of sodium sulfate to remove the remaining water. The solvent was removed in vacuo and the mixture was applied to a silica gel column with gradient methanol in methylene chloride. 0.94 g (86%) of desired product was isolated.

$R_f$=0.375 (hexane/ethyl acetate, 5/1).

UV (methanol), maximum: 306, 233, 206 nm; minimum: 255, 220 nm.

$^1$H NMR (DMSO-$d_6$) δ8.00 (d, 1H), 7.36 (s, 1H), 7.00 (d, 1H), 5.49 (b, OH), 5.31 (q, 1H), 4.19 (m, 2H), 3.77 (t, 2H), 1.95 (m, 2H), 1.37 (d, 3H), 0.86 (s, 9H), 0.04 (s, 6H).

$^{13}$C NMR (DMSO-$d_6$) δ162.6, 146.2, 139.6, 126.9, 112.9, 112.5, 64.8, 63.9, 58.7, 31.5, 25.6, 24.9, −3.4, −5.8.

D. 1-(2-Nitro-5-(3-hydroxypropoxy)phenyl)ethanol 1-(2-Nitro-5-(3-O-t-butyldimethylsilylpropoxy)phenyl)ethanol (0.89 g, 2.5 mmol) was dissolved in 30 ml of THF and 0.5 mmol of nBu$_4$NF was added under stirring. The mixture was stirred at room temperature for 5 hr and the solvent was removed in vacuo. The remaining residue was applied to a silica gel column with gradient methanol in methylene chloride. 1-(2-nitro-5-(3-hydroxypropoxy)phenyl)ethanol (0.6 g (99%) was obtained.

$R_f$=0.17 (dichloromethane/methanol, 95/5).

UV (methanol), maximum: 304, 232, 210 nm; minimum: 255, 219 nm.

$^1$H NMR (DMSO-$d_6$) δ8.00 (d, 1H), 7.33 (s, 1H), 7.00 (d, 1H), 5.50 (d, OH), 5.28 (t, OH), 4.59 (t, 1H), 4.17 (t, 2H), 3.57 (m, 2H), 1.89 (m, 2H), 1.36 (d, 2H).

$^{13}$C NMR (DMOS-$d_6$) δ162.8, 146.3, 139.7, 127.1, 113.1, 112.6, 65.5, 64.0, 57.0, 31.8, 25.0.

E. 1-(2-Nitro-5-(3-O-4,4'-dimethoxytritylpropoxy)phenyl)ethanol 1-(2-Nitro-5-(3-hydroxypropoxy)phenyl)ethanol (0.482 g, 2 mmol) was co-evaporated with anhydrous pyridine twice and dissolved in 20 ml anhydrous pyridine. The solution was cooled in ice water bath and 750 mg (2.2 mmol) of DMTCI was added. The reaction mixture was stirred at room temperature overnight and 0.5 ml methanol was added to stop the reaction. The solvent was removed in vacuo and the residue was co-evaporated with toluene twice to remove trace of pyridine. The final residue was applied to a silica gel column with gradient methanol in methylene chloride containing drops of triethylamine to yield 0.96 g (89%) of the desired product 1-(2-nitro-5-(3-O-4,4'-dimethoxytritylpropoxy)phenyl)ethanol.

$R_f$=0.50 (dichloromethane/methanol, 99/1).

UV (methanol), maximum: 350 (shoulder), 305, 283, 276 (shoulder), 233, 208 nm; minimum: 290, 258, 220 nm.

$^1$H NMR (DMSO-d6) δ8.00 (d, 1H), 6.82–7.42 (ArH), 5.52 (d, OH), 5.32 (m, 1H), 4.23 (t, 2H), 3.71 (s, 6H), 3.17 (t, 2H), 2.00 (m, 2H), 1.37 (d, 3H).

$^{13}$C NMR (DMOS-$d_6$) δ162.5, 157.9, 157.7, 146.1, 144.9, 140.1, 139.7, 135.7, 129.5, 128.8, 127.6, 127.5, 127.3, 126.9, 126.4, 113.0, 112.8, 112.6, 85.2, 65.3, 63.9, 59.0, 54.8, 28.9, 24.9.

F. 1-(2-Nitro-5-(3-O-4,4'-dimethoxytritylpropoxy)phenyl)-1-O-((2-cyanoethoxy)-diisopropylaminophosphino)ethane 1-(2-Nitro-5-(3-O-4,4'-dimethoxytritylpropoxy)phenyl)ethanol (400 mg, 0.74 mmol) was dried under high vacuum and was dissolved in 20 ml of anhydrous methylene chloride. To this solution, it was added 0.5 ml N,N-diisopropylethylamine and 0.3 ml (1.34 mmol) of 2-cyanoethyl-N,N-diisopropylchlorophosphoramidite. The reaction mixture was stirred at room temperature for 30 min and 0.5 ml of methanol was added to stop the reaction. The mixture was washed with saturated sodium bicarbonate solution and was dried over sodium sulfate. The solvent was removed in vacuo and a quick silica gel column with 1% methanol in methylene chloride containing drops of triethylamine yield 510 mg (93%) the desired phosphoramidite.

$R_f$=0.87 (dichloromethane/methanol, 99/1).

EXAMPLE 3

1-(4-(3-O-4,4'-Dimethoxytritylpropoxy)-3-methoxy-6-nitrophenyl)-1-O-((2-cyanoethoxy)-diisopropylaminophosphino)ethane

A. 4-(3-Hydroxypropoxy)-3-methoxyacetophenone

3-Bromo-1-propanol (53 ml, 33 mmol) was refluxed in 100 ml of anhydrous acetonitrile with 4-hydroxy-3-methoxyacetophenone (5 g, 30 mmol), K$_2$CO$_3$ (5 g), and KI (300 mg) overnight (15 h). Methylene chloride (150 ml) was added to the reaction mixture after cooling to room temperature. The mixture was filtered and the solid residue was washed with methylene chloride. The combined organic solution was evaporated to dryness and redissolved in 100 ml methylene chloride. The resulted solution was washed with saturated NaCl solution and dried over sodium sulfate. 6.5 g (96.4%) of desired product was obtained after removal of the solvent in vacuo.

$R_f$=0.41 (dichloromethane/methanol, 95/5).

UV (methanol), maximum: 304, 273, 227, 210 nm: minimum: 291, 244, 214 nm.

¹H NMR (DMSO-d₆) δ7.64 (d, 1H), 7.46 (s, 1H), 7.04 (d, 1H), 4.58 (b, OH), 4.12 (t, 2H), 3.80 (s, 3H), 3.56 (t, 2H), 2.54 (s, 3H), 1.88 (m, 2H).

¹³C NMR (DMSO-d₆) δ196.3, 152.5, 148.6, 129.7, 123.1, 111.5, 110.3, 65.4, 57.2, 55.5, 31.9, 26.3.

B. 4-(3-Acetoxypropoxy)-3-methoxyacetophenone 4-(3-Hydroxypropoxy)-3-methoxyacetophenone (3.5 g, 15.6 mmol) was dried and dissolved in 80 ml anhydrous acetonitrile. To this mixture, 6 ml of triethylamine and 6 ml of acetic anhydride were added. After 4 h, 6 ml methanol was added and the solvent was removed in vacuo. The residue was dissolved in 100 ml dichloromethane and the solution was washed with dilute sodium bicarbonate solution, then water. The organic phase was dried over sodium sulfate and the solvent was removed. The solid residue was applied to a silica gel column with methylene chloride to yield 4.1 g of 4-(3-acetoxypropoxy)-3-methoxyacetophenone (98.6%).

$R_f$=0.22 (dichloromethane/methanol, 99/1).

UV (methanol), maximum: 303, 273, 227, 210 nm; minimum: 290, 243, 214 nm.

¹H NMR (DMSO-d₆) δ7.62 (d, 1H), 7.45 (s, 1H), 7.08 (d, 1H), 4.12 (m, 4H), 3.82 (s, 3H), 2.54 (s, 3H), 2.04 (m, 2H), 2.00 (s, 3H).

¹³C NMR (DMSO-d₆) δ196.3, 170.4, 152.2, 148.6, 130.0, 123.0, 111.8, 110.4, 65.2, 60.8, 55.5, 27.9, 26.3, 20.7.

C. 4-(3-Acetoxypropoxy)-3-methoxy-6-nitroacetophenone 4-(3-Acetoxypropoxy)-3-methoxyacetophenone (3.99 g, 15 mmol) was added portionwise to 15 ml of 70% HNO₃ in water bath; the reaction temperature was maintained at the room temperature. The reaction mixture was stirred at room temperature for 30 min and 30 g of crushed ice was added. This mixture was extracted with 100 ml of dichloromethane and the organic phase was washed with saturated sodium bicarbonate solution. The solution was dried over sodium sulfate and the solvent was removed in vacuo. The crude mixture was applied to a silica gel column with gradient methanol in methylene chloride to yield 3.8 g (81.5%) of desired product 4-(3-acetoxypropoxy)-3-methoxy-6-nitroacetophenone and 0.38 g (8%) of ipso-substituted product 5-(3-acetoxypropoxy)-4-methoxy-1,2-dinitrobenzene.

Side ipso-substituted product 5-(3-acetoxypropoxy)-4-methoxy-1,2-dinitrobenzene:

$R_f$=0.47 (dichloromethane/methanol, 99/1).

UV (methanol), maximum: 334, 330, 270, 240, 212 nm; minimum: 310, 282, 263, 223 nm.

¹H NMR (CDCl₃) δ7.36 (s, 1H), 7.34 (s, 1H), 4.28 (t, 2H), 4.18 (t, 2H), 4.02 (s, 3H), 2.20 (m, 2H), 2.08 (s, 3H).

¹³C NMR (CDCl³) δ170.9, 152.2, 151.1, 117.6, 111.2, 107.9, 107.1, 66.7, 60.6, 56.9, 28.2, 20.9.

Desired product 4-(3-acetoxypropoxy)-3-methoxy-6-nitroacetophenone:

$R_f$=0.29 (dichloromethane/methanol, 99/1).

UV (methanol), maximum: 344, 300, 246, 213 nm; minimum: 320, 270, 227 nm.

¹H NMR (CDCl₃) δ7.62 (s, 1H), 6.74 (s, 1H), 4.28 (t, 2H), 4.20 (t, 2H), 3.96 (s, 3H), 2.48 (s, 3H), 2.20 (m, 2H), 2.08 (s, 3H).

¹³C NMR (CDCl₃) δ200.0, 171.0, 154.3, 148.8, 138.3, 133.0, 108.8, 108.0, 66.1, 60.8, 56.6, 30.4, 28.2, 20.9.

D. 1-(4-(3-Hydroxypropoxy)-3-methoxy-6-nitrophenyl)ethanol 4-(3-Acetoxypropoxy)-3-methoxy-6-nitroacetophenone (3.73 g, 12 mmol) was added 150 ml ethanol and 6.5 g of K₂CO₃. The mixture was stirred at room temperature for 4 hr and TLC with 5% methanol in dichloromethane indicated the completion of the reaction. To this same reaction mixture was added 3.5 g of NaBH₄ and the mixture was stirred at room temperature for 2 hr. Acetone (10 ml) was added to react with the remaining NaBH₄. The solvent was removed in vacuo and the residue was uptaken into 50 g of silica gel. The silica gel mixture was applied on the top of a silica gel column with 5% methanol in methylene chloride to yield 3.15 g (97%) of desired product 1-(4-(3-hydroxypropoxy)-3-methoxy-6-nitrophenyl)ethanol.

Intermediate product 4-(3-hydroxypropoxy)-3-methoxy-6-nitroacetophenone after deprotection:

$R_f$=0.60 (dichloromethane/methanol, 95/5).

Final product 1-(4-(3-hydroxypropoxy)-3-methoxy-6-nitrophenyl)ethanol:

$R_f$=0.50 (dichloromethane/methanol, 95/5).

UV (methanol), maximum: 344, 300, 243, 219 nm: minimum: 317, 264, 233 nm.

¹H NMR (DMSO-d₆) δ7.54 (s, 1H), 7.36 (s, 1H), 5.47 (d, OH), 5.27 (m, 1H), 4.55 (t, OH), 4.05 (t, 2H), 3.90 (s, 3H), 3.55 (q, 2H), 1.88 (m, 2H), 1.37 (d, 3H).

¹³C NMR (DMSO-d₆) δ153.4, 146.4, 138.8, 137.9, 109.0, 108.1, 68.5, 65.9, 57.2, 56.0, 31.9, 29.6.

E. 1-(4-(3-O-4,4'-Dimethoxytritylpropoxy)-3-methoxy-6-nitrophenyl)ethanol 1-(4-(3-Hydroxypropoxy)-3-methoxy-6-nitrophenyl)ethanol (0.325 g, 1.2 mmol) was co-evaporated with anhydrous pyridine twice and dissolved in 15 ml anhydrous pyridine. The solution was cooled in ice-water bath and 450 mg (1.33 mmol) of DMTCl was added. The reaction mixture was stirred at room temperature overnight and 0.5 ml methanol was added to stop the reaction. The solvent was removed in vacuo and the residue was co-evaporated with toluene twice to remove trace of pyridine. The final residue was applied to a silica gel column with gradient methanol in methylene chloride containing drops of triethylamine to yield 605 mg (88%) of desired product 1-(4-(3-O-4,4'-dimethoxytritylpropoxy)-3-methoxy-6-nitrophenyl)ethanol.

$R_f$=0.50 (dichloromethane/methanol, 95/5).

UV (methanol), maximum: 354, 302, 282, 274, 233, 209 nm; minimum: 322, 292, 263, 222 nm.

¹H NMR (DMSO-d₆) δ7.54 (s, 1H), 6.8–7.4 (ArH), 5.48 (d, OH), 5.27 (m, 1H), 4.16 (t, 2H), 3.85 (s, 3H), 3.72 (s, 6H), 3.15 (t, 2H), 1.98 (t, 2H), 1.37 (d, 3H).

¹³C NMR (DMSO-d₆) δ157.8, 153.3, 146.1, 144.9, 138.7, 137.8, 135.7, 129.4, 128.7, 127.5, 127.4, 126.3, 112.9, 112.6, 108.9, 108.2, 85.1, 65.7, 63.7, 59.2, 55.8, 54.8, 29.0, 25.0.

F. 1-(4-(3-O-4,4'-Dimethoxytritylpropoxy)-3-methoxy-6-nitrophenyl)-1-O-((2-cyanoethoxy)-diisopropylaminophosphino)ethane 1-(4-(3-O-4,4'-Dimethoxytritylpropoxy)-3-methoxy-6-nitrophenyl)ethanol (200 mg, 3.5 mmol) was dried under high vacuum and was dissolved in 15 ml of anhydrous methylene chloride. To this solution, it was added 0.5 ml N,N-diisopropylethylamine and 0.2 ml (0.89 mmol) of 2-cyanoethyl-N,N-diisopropylchlorophosphoramidite. The reaction mixture was stirred at room temperature for 30 min and 0.5 ml of methanol was added to stop the reaction. The mixture was washed with saturated sodium bicarbonate solution and was dried over sodium sulfate. The solvent was removed in vacuo and a quick silica gel column with 1% methanol in methylene chloride containing drops of triethylamine yield 247 mg (91.3%) the desired phosphoramidite 1-(4-(3-O-4,4'-dimethoxytritylpropoxy)-3-methoxy-6-nitrophenyl)-1-O-((2-cyanoethoxy)-diisopropylaminophosphino)ethane. $R_f=0.87$ (dichloromethane/methanol, 99/1).

Since modifications will be apparent to those of skill in this art, it is intended that this invention be limited only by the scope of the appended claims.

What is claimed is:

1. A process for obtaining information on a sequence of a target nucleic acid molecule by determining the identity of a polypeptide encoded by the nucleic acid molecule, comprising the steps of:
   a) preparing the encoded polypeptide from a target nucleic acid molecule by in vitro translation, or by in vitro transcription followed by translation, of the target nucleic acid molecule;
   b) determining the molecular mass of the encoded polypeptide by mass spectrometry; and
   c) determining the identity of the polypeptide by comparing the molecular mass of the polypeptide with the molecular mass of a corresponding known polypeptide, thereby obtaining information on a sequence of nucleotides in the target nucleic acid molecule.

2. The process of claim 1, wherein the nucleic acid encoding the encoded polypeptide is RNA, and wherein the encoded polypeptide is obtained by in vitro translation.

3. The process of claim 1, wherein an RNA encoding the encoded polypeptide is prepared by in vitro transcription of the nucleic acid encoding the encoded polypeptide, and wherein the encoded polypeptide is obtained by in vitro translation of the RNA.

4. The process of claim 1, further comprising amplifying the nucleic acid encoding the encoded polypeptide.

5. The process of claim 4, wherein the amplifying is performed using a forward primer and a reverse primer.

6. The process of claim 4, wherein the amplifying is performed using a primer comprising a nucleotide sequence encoding a regulatory element selected from the group consisting of a ribosome binding site, a START codon and a transcription start signal, wherein, following amplification, the regulatory element is operably linked to the nucleic acid encoding the encoded polypeptide.

7. The process of claim 4, wherein the amplifying is performed using a primer comprising a nucleotide sequence encoding an RNA polymerase promoter, wherein, following amplification, the promoter is operably linked to the nucleic acid encoding the encoded polypeptide.

8. The process of claim 7, wherein the RNA polymerase promoter is selected from the group consisting of SP6 promoter, T3 promoter, and T7 promoter.

9. The process of claim 1, wherein the nucleic acid further comprises an operably linked exogenous nucleotide sequence encoding a regulatory element selected from the group consisting of an RNA polymerase promoter, a ribosome binding site, a START codon, and a transcription start signal.

10. The process of claim 1, wherein the nucleic acid comprises a nucleotide sequence, or complement thereof, encoding a second polypeptide.

11. The process of claim 10, wherein the second polypeptide is a tag peptide.

12. The process of claim 11, wherein the tag peptide is selected from the group consisting of a myc epitope, a *Haemophilus influenza* hemagglutinin peptide, a polyhistidine sequence, a polylysine sequence, a polyarginine sequence, and glutathione-S-transferase.

13. The process of claim 1, wherein the encoded polypeptide comprises a tag.

14. The process of claim 13, wherein the tag is biotin or a derivative thereof.

15. The process of claim 13, wherein the tag is a tag peptide, which is conjugated to the encoded polypeptide.

16. The process of claim 2, wherein the in vitro translation is performed in a cell-free extract.

17. The process of claim 16, wherein the cell-free extract is a eukaryotic cell-free extract.

18. The process of claim 17, wherein the eukaryotic cell-free extract is selected from the group consisting of a reticulocyte lysate, a wheat germ extract, and a combination thereof.

19. The process of claim 3, wherein the in vitro transcription is performed in a cell-free extract, and wherein translation of the target polypeptide is performed in the same cell-free extract.

20. The process of claim 19, wherein the cell-free extract comprises a reticulocyte lysate.

21. The process of claim 19, wherein the cell-free extract is a prokaryotic cell-free extract.

22. The process of claim 21, wherein the prokaryotic cell-free extract is an *E. coli* cell-free extract.

23. The process of claim 22, wherein the cell-free extract is *E. coli* S30 cell-free extract.

24. The process of claim 1, wherein transcription or translation is performed in vivo.

25. The process of claim 24, which is performed in a host cell.

26. The process of claim 25, wherein the host cell is a bacterium.

27. The process of claim 1, wherein the encoded polypeptide is isolated prior to mass spectrometry.

28. The process of claim 27, wherein the encoded polypeptide is isolated be reaction with an antibody.

29. The process of claim 13, wherein the encoded polypeptide is isolated by reaction with a reagent that interacts specifically with the tag.

30. The process of claim 29, wherein the tag is a tag peptide and the reagent is an antibody.

31. The process of claim 29, wherein the tag is a polyhistidine tag peptide and the reagent is a metal ion selected from the group consisting of nickel ions and cobalt ions, or wherein the tag is a polylysine or a polyarginine tag peptide and the reagent is selected from the group consisting of copper ions and zinc ions, wherein the reagent is chelated to a solid support.

32. The process of claim 29, wherein the tag is biotin or a derivative thereof and the reagent is selected from the group consisting of avidin and streptavidin.

33. The process of claim 1, wherein, prior to determining the molecular mass of the target polypeptide by mass spectrometry, the target polypeptide is immobilized on a solid support.

34. The process of claim 33, wherein the encoded polypeptide is immobilized to the solid support through a cleavable linker.

35. The process of claim 34, wherein the cleavable linker is selected from the group consisting of an acid cleavable linker, acid-labile linker, heat sensitive linker, and a photocleavable linker.

36. The process of claim 33, wherein the encoded polypeptide is immobilized by interacting specifically with a polypeptide that is conjugated to the solid support.

37. The process of claim 33, wherein the solid support is selected from the group consisting of a support having a flat surface and a support having a surface with a structure.

38. The process of claim 1, wherein the mass spectrometry is selected from the group consisting of matrix assisted laser desorption ionization (MALDI), delayed extraction MALDI, continuous or pulsed electrospray, ionspray, thermospray, or massive cluster impact and a detection format selected from the group consisting of linear time-of-flight, reflectron time-of-flight, single quadrupole, multiple quadrupole, single magnetic sector, multiple magnetic sector, Fourier transform ion cyclotron resonance, ion trap, and combinations thereof.

39. The process of claim 1, wherein the mass spectrometry is matrix-assisted laser desorption/ionization time-of-flight spectrometry.

40. The process of claim 1, wherein the encoded polypeptide is encoded by an allelic variant of a polymorphic region of a chromosome in a subject.

41. The process of claim 40, wherein the polymorphic region is in a gene.

42. The process of claim 40, wherein the polymorphic region is not in a gene.

43. The process of claim 40, wherein the allelic variant is associated with a disease or condition, thereby indicating that the subject has or is at risk of developing the disease or condition.

44. The process of claim 43, wherein the disease or condition is associated with an abnormal number of nucleotide repeats in the allelic variant.

45. The process of claim 44, wherein the nucleotide repeats are trinucleotide repeats.

46. The process of claim 45, wherein the disease or condition is selected from the group consisting of Huntington's disease, prostate cancer, Fragile X syndrome type A, myotonic dystrophy type I, Kennedy disease, Machado-Joseph disease, dentatorubral and pallidolyusian atrophy, spino bulbar muscular atrophy and aging.

47. The process of claim 41, wherein the gene is selected from the group consisting of BRCA1, BRCA2, APC, dystrophin gene, β-globin, Factor IX, Factor VIIc, ornithine-d-amino-transferase, hypoxanthine guanine phosphoribosyl transferase, CFTR, p53, and a proto-oncogene.

48. The process of claim 40, wherein the allelic variant is due to a point mutation.

49. The process of claim 41, wherein the polymorphic region is associated with graft rejection and the process is for determining compatibility between a donor and a recipient of a graft.

50. The process of claim 49, wherein the polymorphic region is the major histocompatibility locus.

51. The process of claim 40, wherein the encoded polypeptide is encoded by a nucleic acid comprising nucleotide repeats and the process is for a use selected from the group consisting of genotyping the subject, forensic analysis, and paternity testing.

52. The process of claim 51, wherein genotyping is performed by quantifying the number of nucleotide repeats.

53. The process of claim 51, wherein the nucleotide repeats are dinucleotide, trinucleotide, tetranucleotide, or pentanucleotide repeats.

54. The process of claim 42, wherein the gene is a mitochondrial gene.

55. The process of claim 1, wherein the encoded polypeptide is obtained from an infectious organism.

56. The process of claim 55, wherein the infectious organism is selected from the group consisting of a virus, a bacterium, a fungus, and a protist.

57. A process for obtaining information on sequences of a plurality of nucleic acid molecules by determining the identity of a plurality of target polypeptides encoded by the nucleic acid molecules, comprising the steps of:
  a) obtaining a plurality of nucleic acid molecules encoding a plurality of target polypeptides;
  b) preparing a plurality of differentially mass modified target polypeptides from the plurality of nucleic acid molecules;
  c) determining the molecular mass of each differentially mass modified target polypeptide in the plurality by mass spectrometry; and d) determining the identity of each target polypeptide in the plurality by comparing the molecular mass of each differentially mass modified target polypeptide in the plurality with the molecular mass of a corresponding known polypeptide, thereby obtaining information on nucleotide sequences in the plurality of nucleic acid molecules encoding the target polypeptides; wherein each encoded polypeptide is immobilized to the solid support through a cleavable linker.

58. The process of claim 57, wherein the encoded polypeptides are obtained by in vitro translation, or by in vitro transcription, followed by translation, of a nucleic acid encoding the encoded polypeptide.

59. The process of claim 57, wherein, prior to determining the molecular mass of each differentially mass modified encoded polypeptide by mass spectrometry, each encoded polypeptide is immobilized on a solid support.

60. A process for identifying a target nucleic acid molecule by determining the identity of a polypeptide encoded by the nucleic acid molecule, comprising the steps of:
   a) preparing the encoded polypeptide by in vitro translation, or by in vitro transcription followed by translation, of a target nucleic acid molecule encoding the polypeptide;
   b) contacting the encoded polypeptide with at least one agent that cleaves at least one peptide bond in the encoded polypeptide to produce peptide fragments of the encoded polypeptide;
   c) determining the molecular mass of at least one of the peptide fragments of the encoded polypeptide by mass spectrometry; and
   d) comparing the molecular mass of the peptide fragments of the encoded polypeptide with the molecular mass of peptide fragments of a corresponding known polypeptide, thereby determining the identity of the encoded polypeptide and the target nucleic acid molecule.

61. The process of claim 60, wherein the encoded polypeptide is immobilized to a solid support prior to contacting the encoded polypeptide with the agent.

62. The process of claim 60, wherein the encoded polypeptide is immobilized to the solid support through a cleavable linker.

63. The process of claim 62, wherein the encoded polypeptide is immobilized to the solid support through a chemically cleavable linker at one terminus of the polypeptide and through a photocleavable linker at the other terminus of the polypeptide.

64. The process of claim 60, wherein the encoded polypeptide is conditioned prior to step c), or the peptide fragments of the encoded polypeptide are conditioned prior to step d).

65. The process of claim 60, wherein the agent that cleaves at least one peptide bond in the encoded polypeptide is an endopeptidase.

66. A process for obtaining information on sequences of a plurality of nucleic acid molecules by determining the identity of a plurality of encoded polypeptides encoded by the nucleic acid molecules, comprising the steps of:
   a) obtaining a plurality of nucleic acid molecules encoding a plurality of encoded polypeptides;
   b) preparing a plurality of encoded polypeptides from the plurality of nucleic acid molecules;
   c) contacting each encoded polypeptide with at least one agent that cleaves at least one peptide bond in each encoded polypeptide to produce peptide fragments of each encoded polypeptide;
   d) determining the molecular mass of at least one of the peptide fragments of each encoded polypeptide in the plurality by mass spectrometry; and
   e) determining the identity of each encoded polypeptide in the plurality by comparing the molecular mass of the peptide fragments of each encoded polypeptide with the molecular mass of peptide fragments of a corresponding known polypeptide, thereby obtaining information on nucleotide sequences in the plurality of nucleic acid molecules encoding the encoded polypeptides.

67. The process of claim 66, wherein each encoded polypeptide is mass modified prior to step b), or the at least one peptide fragment of each encoded polypeptide is mass modified prior to step c).

68. The process of claim 66, wherein each encoded polypeptide in the plurality is immobilized to a solid support prior to contacting each encoded polypeptide with the agent.

69. The process of claim 66, wherein each encoded polypeptide is immobilized to the solid support through a cleavable linker.

70. The process of claim 66, wherein each encoded polypeptide is conditioned prior to step c), or the at least one peptide fragment of each encoded polypeptide is conditioned prior to step d).

71. (Amended) The process of claim 68, wherein the plurality of encoded polypeptides are immobilized in an array.

72. The process of claim 66, wherein the agent that cleaves at least one peptide bond in each encoded polypeptide is an endopeptidase.

73. The process of claim 66, wherein each encoded polypeptide is immobilized to the solid support through an chemically cleavable linker at one terminus of the polypeptide and through a photocleavable linker at the other terminus of the polypeptide.

74. The process of claim 33, wherein the solid support is selected from the group consisting of beads, beads in an array of pits, capillaries, flat supports, plastic materials, wafers, combs, pins, arrays of pins, needles, arrays of needles, wells and nanoliter wells.

75. The process of claim 74, wherein the beads are selected from the group consisting of silica gel beads, controlled pore glass beads, magnetic beads, 4-(hydroxymethyl)phenoxymethylcopoly(styrene-1% divinylbenzene) resin, chloromethylated copolystyrene-divinylbenzene resin, cellulose beads, agarose beads and dextran beads.

76. The process of claim 74, wherein the flat supports are selected from the group consisting of glass fiber filters, glass surfaces, and metal surfaces.

77. The process of claim 76, wherein the metal surfaces are selected from the group consisting of steel, gold, silver, aluminum, silicon, and copper.

78. The process of claim 74, wherein the plastic materials are selected from the group consisting of polyethylene, polypropylene, polyamide, and polyvinylidene difluoride.

79. The process of claim 74, wherein the wafers are selected from the group consisting of silicon wafers, wafers with pits, wafers with filter bottoms, and wafers without filter bottoms.

80. The process of claim 33, wherein the target polypeptide is linked to the solid support by an interaction selected from the group consisting of hydrophobic interaction, hydrophilic interaction, and ionic interaction.

81. The process of claim 33, wherein the N-terminal amino acid of the target polypeptide is linked to the solid support.

82. The process of claim 33, wherein the C-terminal amino acid of the target polypeptide is linked to the solid support.

83. The process of claim 33, wherein the target polypeptide is covalently conjugated to the solid support.

84. The process of claim 83, wherein the target polypeptide is covalently conjugated to the solid support by reaction with a thiol-reactive functionality.

85. The process of claim 57, wherein each target polypeptide is conditioned prior to step c).

86. The process of claim 85, wherein the target polypeptide is immobilized to a solid support prior to conditioning.

87. The process of claim 85, wherein the conditioning is selected from the group consisting of anion exchange, cation exchange, treatment with an alkylating agent, treatment with trialkylsilylchloride, and incorporation of modified amino acids.

88. The process of claim 64, wherein the target polypeptide is immobilized to a solid support prior to conditioning.

89. The process of claim 64, wherein the conditioning is selected from the group consisting of anion exchange, cation exchange, treatment with an alkylating agent, treatment with trialkylsilylchloride, and incorporation of modified amino acids.

90. The process of claim 70, wherein the target polypeptide is immobilized to a solid support prior to conditioning.

91. The process of claim 64, wherein the conditioning is selected from the group consisting of anion exchange, cation exchange, treatment with an alkylating agent, treatment with trialkylsilylchloride, and incorporation of modified amino acids.

92. The process of claim 59, wherein the cleavable linker is selected from the group consisting of an acid cleavable linker, acid-labile linker, heat sensitive linker, and a photo-cleavable linker.

93. The process of claim 59, wherein the solid support is selected from the group consisting of a support having a flat surface and a support having a surface with a structure.

94. The process of claim 59, wherein each target polypeptide is immobilized in an array to the solid support.

95. The process of claim 59, wherein each target polypeptide is immobilized due to its interacting specifically with a polypeptide of interest, wherein the polypeptide of interest is conjugated in an array to the solid support.

* * * * *

UNITED STATES PATENT AND TRADEMARK OFFICE
CERTIFICATE OF CORRECTION

PATENT NO.    : 6,322,970 B1                                        Page 1 of 1
DATED         : November 27, 2001
INVENTOR(S)   : Little et al.

It is certified that error appears in the above-identified patent and that said Letters Patent is hereby corrected as shown below:

Title page,
Please add to Item [*] Notice: -- This patent is subject to a terminal disclaimer. --
Item [56], References Cited, replace patent number "4,681,394" with -- 4,683,194 --.
Add the following:
-- Sinha et al., Polymer support oligonucleotide synthesis XVIII: Use of beta-cyanoethyl-N,N-dialkylamino-/N-morpholino phosphoramidite of deoxynucleosides for the synthesis of DNA fragments simplifying deprotection and isolation of final products, Nucleic Acid Res. 12:4539 (1984). --

Column 77,
Lines 24 and 25, claim 28 should read as follows:
-- 28. The process of claim 27, wherein the encoded polypeptide is isolated by reaction with an antibody. --

Signed and Sealed this

Second Day of July, 2002

Attest:

Attesting Officer

JAMES E. ROGAN
Director of the United States Patent and Trademark Office